US007335492B2

(12) United States Patent
Penttilä et al.

(10) Patent No.: US 7,335,492 B2
(45) Date of Patent: Feb. 26, 2008

(54) PROCESS FOR PARTITIONING OF PROTEINS

(75) Inventors: Merja Penttilä, Helsinki (FI); Tiina Nakari-Setälä, Espoo (FI); Richard Fagerström, Espoo (FI); Klaus Selber, Aachen (DE); Maria-Regina Kula, Niederzier (DE); Markus Linder, Helsinki (FI); Folke Tjerneld, Limhamn (SE)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 0 days.

(21) Appl. No.: 11/252,753

(22) Filed: Oct. 19, 2005

(65) Prior Publication Data

US 2006/0084164 A1    Apr. 20, 2006

Related U.S. Application Data

(62) Division of application No. 09/936,823, filed as application No. PCT/FI00/00249 on Mar. 24, 2000, now Pat. No. 7,060,669.

(30) Foreign Application Priority Data

Mar. 25, 1999 (FI) ..................................... 990667
Aug. 20, 1999 (FI) ................................. 19991782

(51) Int. Cl.
*C12N 1/00* (2006.01)
*A61K 38/00* (2006.01)

(52) U.S. Cl. .................... 435/69.1; 435/69.2; 435/41; 435/70.21; 435/68.1

(58) Field of Classification Search ................ 530/300, 530/350, 412, 387.2; 514/2; 435/70.1, 71, 435/9.7, 440, 7.1, 69.1, 69.2, 41, 68.1, 70.21
See application file for complete search history.

(56) References Cited

U.S. PATENT DOCUMENTS

| | | | |
|---|---|---|---|
| 5,139,943 | A | 8/1992 | Heinsohn et al. |
| 5,304,310 | A | 4/1994 | Lang et al. |
| 5,882,520 | A | 3/1999 | Richards et al. |

FOREIGN PATENT DOCUMENTS

| | | |
|---|---|---|
| EP | 0574050 A1 | 12/1993 |
| WO | WO-9207868 | 5/1992 |
| WO | WO-9401567 | 1/1994 |
| WO | WO-9404673 | 3/1994 |
| WO | WO-9418330 | 8/1994 |

OTHER PUBLICATIONS

Kershaw et al. (2005) Four conserved intramolecular disulphide linkages are required for secretion and cell wall localization of a hydrophobin during fungal morphogenesis. Mol. Microbiol. vol. 56, No. 1, pp. 117-125.*
Tagu et al. (2001) Immunolocalization of hydrophobin HYDPt-1 from the ectomycorrhizal basidiomycete *Pisolithus tinctorius* during colonization of *Eucalyptus globulus* roots, New Phytol. vol. 149, pp. 127-135.*
Nakari-Setala et al. (1996) Genetic and biochemical characterization of the *Trichoderma reesei* hydrophobin HFBI. Eur. J. Biochem. vol. 235, Nos. -12, pp. 248-255.*
Asgeirsdottir et al. (1999) A sandwiched-culture technique for evaluation of heterologous protein production in a filamentous fungus. Appl. Environ. Microbiol. vol. 65, No. 5, pp. 2250-2252.*
Gordon et al. (2000) Glucoamylase::green fluorescent protein fusions to monitor protein secretion in *Aspergillus niger*. Microbiology. vol. 146, Part 2, pp. 415-426.*
Kershaw et al. (1998) Complementation of the mpg1 mutant phenotype in Magnaporthe grisea reveals functional relationships between fungal hydrophobins. EMBO J. vol. 17, No. 14 pp. 3838-3849.*
Nakari-Setala et al. (2002) Expression of a fungal hydrophobin in the *Saccharomyces cerevisiae* cell wall: effect on cell surface properties and immobilization. Appl. Environ. Microbiol. vol. 68, No. 7, pp. 3385-3391.*
Linder et al. (2004) Efficient purification of recombinant proteins using hydrophobins as tags in surfactant-based two-phase systems. Biochemistry. vol. 43, No. 37, pp. 11873-11882.*
Linder et al. (2006) Surface adhesion of fusion proteins containing the hydrophobins HFBI and HFBII from *Trichoderma reesei*. Protein Sci. vol. 11, No. 9, pp. 2257-2266.*
Thomas et al. (1996) Protein misfolding and inclusion body formation in recombinant *Escherichia coli* cells overexpressing Heat-shock proteins. J. Biol. Chem. vol. 271, No. 19, pp. 11141-11147.*
Sokolove et al. (1996) A mitochondrial signal peptide from *Neurospora crassa* increases the permeability of isolated rat liver mitochondria, Arch. Biochem. Biophys., vol. 336, No. 1, pp. 69-76.*
Wikipedia (2007, updated) Microorganism, http://en.wikipedia.org/wiki/Microorganism, p. 1 (attachment 1).*
Han et al., *Colloids and Surfaces B: Biointerfaces*, vol. 9, 1997, pp. 109-116.
Hachem et al., *Enzyme and Microbial Technology*, vol. 19, 1996, pp. 507-517.
Franco et al., *Biotechnology and Bioengineering*, vol. 49, 1996, pp. 290-299.
Kuboi et al., *Journal of Chemical Engineering of Japan*, vol. 28, No. 1, 1995, pp. 97-102.
Kuboi et al., *Solvent Extractions Res. Dev. Japan*, vol. 1, 1994, pp. 42-52.
Nakari-Setala et al., *European Journal of Biochemistry*, vol. 248, No. 2, Sep. 1, 1997, pp. 415-423 (abstract only).

(Continued)

*Primary Examiner*—Karen Cochrane Carlson
*Assistant Examiner*—Samuel Wei Liu
(74) *Attorney, Agent, or Firm*—Birch, Stewart, Kolasch & Birch, LLP

(57) ABSTRACT

The present invention relates to isolation and purification of protein in aqueous two-phase systems (ATPS). Specifically, the invention provides processes for partitioning of proteins of interest in ATPS by fusing said proteins to targeting proteins which have the ability of carrying said protein into one of the phases.

18 Claims, 28 Drawing Sheets

OTHER PUBLICATIONS

Nakari-Setala et al., *European Journal of Biochemistry*, vol. 235, No. 1-2, Jan. 15, 1996, pp. 248-255 (abstract only).

Bodhankar et al., *J. Chem. Technol. Biotechnol.*, vol. 73, 1998, pp. 251-258.

Svensson et al., *Journal of Chromatography A*, vol. 839, 1999, pp. 71-83.

Carlsson et al., *Journal of Chromatography A*, 1996, pp. 107-117.

Stahl et al., Elsevier Science Ltd., Tibtech, vol. 15, May 1997, pp. 185-192.

Schreuder et al., Elsevier Science Ltd., Tibtech, vol. 14, Apr. 1996, pp. 115-120.

Kohler et al., Bio/Technology, vol. 9, 1991, pp. 642-646.

Berggren et al., Biotechnology and Bioengineering, vol. 62, No. 2, Jan. 20, 1999; pp. 135-144.

Hassinen et al., Journal of Chromatography A, vol. 668, 1994, pp. 121-128.

Huddleston et al., Biotechnology and Bioengineering, vol. 44, 1994, pp. 626-635.

Liu, C.-L. et al., J Chromatogr B. Biomed Sci Appl., vol. 711, 1998, pp. 127-138.

Tagu, D. et al., Gene, vol. 168, 1996, pp. 93-97.

Reference 1: "Detergents and Surfactants", pp. 1-6.

* cited by examiner

SEQUENCE LISTING

```
<160> NUMBER OF SEQ ID NOS: 46

<210> SEQ ID NO 1
<211> LENGTH: 428
<212> TYPE: DNA
<213> ORGANISM: Trichoderma reesei
<220> FEATURE:
<221> NAME/KEY: intron
<222> LOCATION: (167)..(236)
<220> FEATURE:
<221> NAME/KEY: intron
<222> LOCATION: (323)..(386)
<220> FEATURE:
<221> NAME/KEY: misc_feature
<223> OTHER INFORMATION: Coding sequence of hfb1

<400> SEQUENCE: 1
atgaagttct tcgccatcgc cgctctcttt gccgccgctg ccgttgccca gcctctcgag      60
gaccgcagca acggcaacgg caatgtttgc cctcccggcc tcttcagcaa cccccagtgc     120
```

```
tgtgccaccc aagtccttgg cctcatcggc cttgactgca aagtccgtaa gttgagccat    180
aacataagaa tcctcttgac ggaaatatgc cttctcactc ctttacccct gaacagcctc    240
ccagaacgtt tacgacggca ccgacttccg caacgtctgc gccaaaaccg gcgcccagcc    300
tctctgctgc gtggcccccg ttgtaagttg atgccccagc tcaagctcca gtctttggca    360
aacccattct gacacccaga ctgcaggccg gccaggctct tctgtgccag accgccgtcg    420
gtgcttga                                                              428

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 2
tcgggcacta cgtgccagta tagcaacgac tactactcgc aatgccttgt tccgcgtggc    60
tctagttctg gaaccgca                                                   78

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: PCR
      3' primer

<400> SEQUENCE: 3
tcgtacggat cctcaagcac cgacggcggt                                      30

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 4
actacacgga ggagctcgac gacttcgagc agcccgagct gcacgcagag caacggcaac    60
ggc                                                                   63

<210> SEQ ID NO 5
<211> LENGTH: 2211
<212> TYPE: DNA
<213> ORGANISM: Trichoderma reesei
<220> FEATURE:
<221> NAME/KEY: promoter
<222> LOCATION: (1)..(2211)
<223> OTHER INFORMATION: cbh1 promoter sequence

<400> SEQUENCE: 5
gaattctcac ggtgaatgta ggcctttttgt agggtaggaa ttgtcactca agcaccccca    60
acctccatta cgcctccccc atagagttcc caatcagtga gtcatggcac tgttctcaaa    120
tagattgggg agaagttgac ttccgcccag agctgaaggt cgcacaaccg catgatatag    180
ggtcggcaac ggcaaaaaag cacgtggctc accgaaaagc aagatgtttg cgatctaaca    240
tccaggaacc tggatacatc catcatcacg cacgaccact ttgatctgct ggtaaactcg    300
tattcgccct aaaccgaagt gcgtggtaaa tctacacgtg ggcccctttc ggtatactgc    360
```

-continued

```
gtgtgtcttc tctaggtgca ttctttcctt cctctagtgt tgaattgttt gtgttgggag      420
tccgagctgt aactacctct gaatctctgg agaatggtgg actaacgact accgtgcacc      480
tgcatcatgt atataatagt gatcctgaga agggggtttt ggagcaatgt gggactttga      540
tggtcatcaa acaaagaacg aagacgcctc ttttgcaaag ttttgtttcg gctacggtga      600
agaactggat acttgttgtg tcttctgtgt attttgtgg caacaagagg ccagagacaa       660
tctattcaaa caccaagctt gctcttttga gctacaagaa cctgtggggt atatatctag      720
agttgtgaag tcggtaatcc cgctgtatag taatacgagt cgcatctaaa tactccgaag      780
ctgctgcgaa cccggagaat cgagatgtgc tggaaagctt ctagcgagcg gctaaattag      840
catgaaaggc tatgagaaat tctggagacg gcttgttgaa tcatggcgtt ccattcttcg      900
acaagcaaag cgttccgtcg cagtagcagg cactcattcc cgaaaaaact cggagattcc      960
taagtagcga tggaaccgga ataatataat aggcaataca ttgagttgcc tcgacggttg     1020
caatgcaggg gtactgagct tggacataac tgttccgtac cccacctctt ctcaacctt     1080 ggcgttccc tgattcagcg tacccgtaca agtcgtaatc actattaacc cagactgacc      1140
ggacgtgttt tgcccttcat ttggagaaat aatgtcattg cgatgtgtaa tttgcctgct     1200
tgaccgactg gggctgttcg aagcccgaat gtaggattgt tatccgaact ctgctcgtag     1260
aggcatgttg tgaatctgtg tcgggcagga cacgcctcga aggttcacgg caagggaaac     1320
caccgatagc agtgtctagt agcaacctgt aaagccgcaa tgcagcatca ctggaaaata     1380
caaaccaatg gctaaaagta cataagttaa tgcctaaaga agtcatatac cagcggctaa     1440
taattgtaca atcaagtggc taaacgtacc gtaatttgcc aacgcgttgt ggggttgcag     1500
aagcaacggc aaagcccact tcccacgttt gtttcttcac tcagtccaat ctcagctggt     1560
gatcccccaa ttgggtcgct tgtttgttcc ggtgaagtga agaagacag aggtaagaat      1620 gtctgactcg gagcgttttg catacaacca agggcagtga tggaagacag tgaaatgttg     1680
acattcaagg agtatttagc cagggatgct tgagtgtatc gtgtaaggag gtttgtctgc     1740
cgatacgacg aatactgtat agtcacttct gatgaagtgg tccatattga aatgtaagtc     1800
ggcactgaac aggcaaaaga ttgagttgaa actgcctaag atctcgggcc ctcgggcttc     1860
ggctttgggt gtacatgttt gtgctccggg caaatgcaaa gtgtggtagg atcgacacac     1920
tgctgccttt accaagcagc tgagggtatg tgataggcaa atgttcaggg gccactgcat     1980
ggtttcgaat agaaagagaa gcttagccaa gaacaatagc cgataaagat agcctcatta     2040
aacgaaatga gctagtaggc aaagtcagcg aatgtgtata tataaaggtt cgaggtccgt     2100
gcctccctca tgctctcccc atctactcat caactcagat cctccaggag acttgtacac     2160
catcttttga ggcacagaaa cccaatagtc aaccgcggac tgcgcatcat g             2211
```

<210> SEQ ID NO 6
<211> LENGTH: 1588
<212> TYPE: DNA
<213> ORGANISM: Trichoderma reesei
<220> FEATURE:
<221> NAME/KEY: misc_feature
<223> OTHER INFORMATION: T. reesei egl1 cDNA

<400> SEQUENCE: 6

```
cccccctatc ttagtccttc ttgttgtccc aaaatggcgc cctcagttac actgccgttg       60
accacggcca tcctggccat tgcccggctc gtcgccgccc agcaaccggg taccagcacc      120
cccgaggtcc atcccaagtt gacaacctac aagtgtacaa agtccggggg gtgcgtggcc      180
```

| | |
|---|---|
| caggacacct cggtggtcct tgactggaac taccgctgga tgcacgacgc aaactacaac | 240 |
| tcgtgcaccg tcaacggcgg cgtcaacacc acgctctgcc ctgacgaggc gacctgtggc | 300 |
| aagaactgct tcatcgaggg cgtcgactac gccgcctcgg gcgtcacgac ctcgggcagc | 360 |
| agcctcacca tgaaccagta catgcccagc agctctggcg gctacagcag cgtctctcct | 420 |
| cggctgtatc tcctggactc tgacggtgag tacgtgatgc tgaagctcaa cggccaggag | 480 |
| ctgagcttcg acgtcgacct ctctgctctg ccgtgtggag agaacggctc gctctacctg | 540 |
| tctcagatgg acgagaacgg gggcgccaac cagtataaca cggccggtgc caactacggg | 600 |
| agcggctact gcgatgctca gtgccccgtc cagacatgga ggaacggcac cctcaacact | 660 |
| agccaccagg gcttctgctg caacgagatg gatatcctgg agggcaactc gagggcgaat | 720 |
| gccttgaccc ctcactcttg cacggccacg gcctgcgact ctgccggttg cggcttcaac | 780 |
| ccctatggca gcggctacaa aagctactac ggccccggag ataccgttga cacctccaag | 840 |
| accttcacca tcatcaccca gttcaacacg gacaacggct cgccctcggg caaccttgtg | 900 |
| agcatcaccc gcaagtacca gcaaaacggc gtcgacatcc ccagcgccca gcccggcggc | 960 |
| gacaccatct cgtcctgccc gtccgcctca gcctacggcg gcctcgccac catgggcaag | 1020 |
| gccctgagca gcggcatggt gctcgtgttc agcatttgga acgacaacag ccagtacatg | 1080 |
| aactggctcg acagcggcaa cgccggcccc tgcagcagca ccgagggcaa cccatccaac | 1140 |
| atcctggcca caaccccaa cacgcacgtc gtcttctcca acatccgctg gggagacatt | 1200 |
| gggtctacta cgaactcgac tgcgcccccg ccccgcctg cgtccagcac gacgttttcg | 1260 |
| actacacgga ggagctcgac gacttcgagc agcccgagct gcacgcagac tcactggggg | 1320 |
| cagtgcggtg gcattgggta cagcgggtgc aagacgtgca cgtcgggcac tacgtgccag | 1380 |
| tatagcaacg actactactc gcaatgcctt tagagcgttg acttgcctct ggtctgtcca | 1440 |
| gacggggca cgatagaatg cgggcacgca gggagctcgt agacatttggg cttaatatat | 1500 |
| aagacatgct atgttgtatc tacattagca aatgacaaac aaatgaaaaa gaacttatca | 1560 |
| agcaaaaaaa aaaaaaaaaa aaaaaaaa | 1588 |

<210> SEQ ID NO 7
<211> LENGTH: 745
<212> TYPE: DNA
<213> ORGANISM: Trichoderma reesei
<220> FEATURE:
<221> NAME/KEY: terminator
<222> LOCATION: (1)..(745)
<223> OTHER INFORMATION: T. reesei cbh1 terminator

<400> SEQUENCE: 7

| | |
|---|---|
| ggacctaccc agtctcacta cggccagtgc ggcggtattg gctacagcgg ccccacggtc | 60 |
| tgcgccagcg gcacaacttg ccaggtcctg aacccttact actctcagtg cctgtaaagc | 120 |
| tccgtgcgaa agcctgacgc accggtagat tcttggtgag cccgtatcat gacggcggcg | 180 |
| ggagctacat ggccccgggt gatttatttt ttttgtatct acttctgacc ctttttcaaat | 240 |
| atacggtcaa ctcatctttc actggagatg cggcctgctt ggtattgcga tgttgtcagc | 300 |
| ttggcaaatt gtggctttcg aaaacacaaa acgattcctt agtagccatg catttttaaga | 360 |
| taacggaata gaagaaagag gaaattaaaa aaaaaaaaaa aacaaacatc ccgttcataa | 420 |
| cccgtagaat cgccgctctt cgtgtatccc agtaccacgt caaaggtatt catgatcgtt | 480 |
| caatgttgat attgttccgc cagtatggct ccacccccat ctccgcgaat ctcctcttct | 540 |

```
cgaacgcggt agtggctgct gccaattggt aatgaccata gggagacaaa cagcataata      600
gcaacagtgg aaattagtgg cgcaataatt gagaacacag tgagaccata gctggcggcc      660
tggaaagcac tgttggagac caacttgtcc gttgcgaggc caacttgcat tgctgtcaag      720
acgatgacaa cgtagccgag gaccc                                            745
```

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: annealed
      primer

<400> SEQUENCE: 8

```
taaccgcggt                                                              10
```

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: annealed
      primer

<400> SEQUENCE: 9

```
ctagaccgcg gttaat                                                       16
```

<210> SEQ ID NO 10
<211> LENGTH: 1232
<212> TYPE: DNA
<213> ORGANISM: Trichoderma reesei
<220> FEATURE:
<221> NAME/KEY: promoter
<222> LOCATION: (1)..(1232)
<223> OTHER INFORMATION: T. reesei gpd1 promotor

<400> SEQUENCE: 10

```
gtcgacacga tatacaggcg cggctgatga taatgatgat cgagcatgac ttgatgctgt       60
atgtgacaat attgactgcg aggaaccatc aggtgtgtat ggatggaatc attctgtaac      120
caccaaggtg catgcatcat aaggattctc ctcagctcac caacaacgaa cgatggccat      180
gttagtgaag gcaccgtgat ggcaagatag aaccactatt gcatctgcgc ttcccacgca      240
cagtacgtca agtaacgtca aagccgccct cccgtaacct cgcccgttgt tgctccccc      300 gattgcctca atcacatagt acctacctat gcattatggg cggcctcaac ccacccccc      360 agattgagag ctaccttaca tcaatatggc cagcacctct tcggcgatac atactcgcca      420
ccccagccgg cgcgattgtg tgtactaggt aggctcgtac tataccagca ggagaggtgc      480
tgcttggcaa tcgtgctcag ctgttaggtt gtacttgtat ggtacttgta aggtggtcat      540
gcagttgcta aggtacctag ggagggattc aacgagccct gcttccaatg tccatctgga      600
taggatggcg gctggcgggg ccgaagctgg gaactcgcca acagtcatat gtaatagctc      660
aagttgatga taccgttttg ccagattaga tgcgagaagc agcatgaatg tcgctcatcc      720
gatgccgcat caccgttgtg tcagaaacga ccaagctaag caactaaggt accttaccgt      780
ccactatctc aggtaaccag gtactaccag ctacctaccc tgccgtgcct acctgcttta      840
gtgttaatct ttccacctcc ctcctcaatc ttcttttccc tcctctcctc ttttttttt      900 cttcctcctc ttcttctcca taaccattcc taacaacatc gacattctct cctaatcacc      960
agcctcgcaa atcctcagtt tgtatgtacg tacgtactac aatcatcacc acgatcgtcc     1020
```

```
gcccgacgat gcggcttctg ttcgcctgcc cctcctctca ctcgtgccct tgacgagcta    1080
gccccgccag gactctcctg cgtcaccaat tttttccct atttaccct cctccctctc     1140 tccctctcgt ttcttcctaa caaacaacca ccaccaaaat ctctttggaa gctcacgact   1200
cacgcagctc aattcgcaga tacaaatcta ga                                 1232
```

<210> SEQ ID NO 11
<211> LENGTH: 1129
<212> TYPE: DNA
<213> ORGANISM: Trichoderma reesei
<220> FEATURE:
<221> NAME/KEY: terminator
<222> LOCATION: (1)..(1129)
<223> OTHER INFORMATION: T. reesei gpd1 terminator

<400> SEQUENCE: 11

```
ggatcccgag cattgtctat gaatgcaaac aaaaatagta aataaatagt aattctggcc     60
atgacgaata gagccaatct gctccacttg actatcttgt gactgtatcg tatgtcgaac    120
ccttgactgc ccattcaaac aattgtaaag gaatatagct acaagttatg tctcacgttt    180
gcgtgcgagc ccgtttgtac gttattttga gaaagcgttg ccatcacatg ctcacagtca    240
cttggcttac gatcatgttt gcgatcttcg gtaagaatac acagagtaac gattatctcc    300
atcgcttcta tgattaggta ctcagacaac acatgggaaa caagataacc atcgcatgca    360
aggtcgattc caatcatgat ctggactggg gtattccatc taagccatag taccctcgag    420
agaaggaatg gtaggacctc tcaggcgtcc accatctgtg ctgcaaatcc aagaaacccc    480
ccaaaagcac ctacctatct acctagagta actgcacgag aaaagaaaag gagcagaaga    540
agaatgatct caagaggccg tgaacgcaga acacactcc tcccaacttt tcaagttttg     600
aacaaaaaaa gaaagatgag gactagaaga tggagtattt ccttcttaga gagctctcgg    660
tgaggtgacc tgtcagggtt taccgcaaac cgtcggtggt tctatccaat taatcaagtc    720
ccgcgcctcg cctcttctct cctgtccttt catagaatcc cgtctccttg ttgcttgatc    780
gaagcggggt tatcgacgcc accaaagatc ttgtcttggt gacttatcaa tccttttggtg   840 atcaaacagc ccccgagtga tcagatccgt aaaagaagaa gaagagtacg atttaaccag    900
accgaggaac aataaagcga gtaaataaca tcaaaataag agtctcgttg aaaattactt    960
gttcctcaat caatcccaac cccctaaaa gcccttcccc ccatggtata tcccggcagt    1020
aggagagaga tatttccact accgctcacc accaagtgag gcttgccgag agaagaggat   1080
gaatcagaag tgacaacaac gggttgagca catgggatat cggcgcgcc              1129
```

<210> SEQ ID NO 12
<211> LENGTH: 5733
<212> TYPE: DNA
<213> ORGANISM: Aspergillus nidulans
<220> FEATURE:
<221> NAME/KEY: misc_feature
<223> OTHER INFORMATION: (1-5733) Sequence of plasmid pAN52-1
<220> FEATURE:
<221> NAME/KEY: promoter
<222> LOCATION: (1)..(2129)
<223> OTHER INFORMATION: A. nidulans gpdA promoter
<220> FEATURE:
<221> NAME/KEY: gene
<222> LOCATION: (2130)..(2304)
<223> OTHER INFORMATION: A. nidulans gpdA gene
<220> FEATURE:
<221> NAME/KEY: terminator
<222> LOCATION: (2305)..(3071)
<223> OTHER INFORMATION: A. nidulans trpC terminator
<220> FEATURE:
<221> NAME/KEY: misc_feature
<222> LOCATION: (3072)..(5726)
<223> OTHER INFORMATION: pUC18 from SalI to EcoRI

<400> SEQUENCE: 12

```
caattccctt gtatctctac acacaggctc aaatcaataa gaagaacggt tcgtcttttt       60
cgtttatatc ttgcatcgtc ccaaagctat tggcgggata ttctgtttgc agttggctga      120
cttgaagtaa tctctgcaga tctttcgaca ctgaaatacg tcgagcctgc tccgcttgga      180
agcggcgagg agcctcgtcc tgtcacaact accaacatgg agtacgataa gggccagttc      240
cgccagctca ttaagagcca gttcatgggc gttggcatga tggccgtcat gcatctgtac      300
ttcaagtaca ccaacgctct tctgatccag tcgatcatcc gctgaaggcg ctttcgaatc      360
tggttaagat ccacgtcttc gggaagccag cgactggtga cctccagcgt cccttttaagg     420
ctgccaacag ctttctcagc cagggccagc ccaagaccga caaggcctcc ctccagaacg      480
ccgagaagaa ctggaggggt ggtgtcaagg aggagtaagc tccttattga agtcggagga      540
cggagcggtg tcaagaggat attcttcgac tctgtattat agataagatg atgaggaatt      600
ggaggtagca tagcttcatt tggatttgct ttccaggctg agactctagc ttggagcata      660
gagggtcctt tggcttttcaa tattctcaag tatctcgagt ttgaacttat tccctgtgaa     720
cctttattc accaatgagc attggaatga acatgaatct gaggactgca atcgccatga       780
ggttttcgaa atacatccgg atgtcgaagg cttggggcac ctgcgttggt tgaatttaga      840
acgtggcact attgatcatc cgatagctct gcaaagggcg ttgcacaatg caagtcaaac      900
gttgctagca gttccaggtg gaatgttatg atgagcattg tattaaatca ggagatatag      960
catgatctct agttagctca ccacaaaagt cagacgcgcg aaccaaaagt cacacaacac     1020
aagctgtaag gatttcggca cggctacgga agacggagaa gccaccttca gtggactcga     1080
gtaccatttta attctatttg tgtttgatcg agacctaata cagcccctac aacgaccatc     1140
aaagtcgtat agctaccagt gaggaagtgg actcaaatcg acttcagcaa catctcctgg     1200
ataaacttta agcctaaact atacagaata agataggtgg agagcttata ccgagctccc     1260
aaatctgtcc agatcatggt tgaccggtgc ctggatcttc ctatagaatc atccttattc     1320
gttgacctag ctgattctgg agtgacccag agggtcatga cttgagccta aaatccgccg     1380
cctccaccat ttgtagaaaa atgtgacgaa ctcgtgagct ctgtacagtg accggtgact     1440
ctttctggca tgcggagaga cggacggacg cagagagaag ggctgagtaa taagccactg     1500
gccagacagc tctggcggct ctgaggtgca gtggatgatt attaatccgg gaccggccgc     1560
ccctccgccc cgaagtggaa aggctggtgt gcccctcgtt gaccaagaat ctattgcatc     1620
atcggagaat atggagcttc atcgaatcac cggcagtaag cgaaggagaa tgtgaagcca     1680
ggggtgtata gccgtcggcg aaatagcatg ccattaacct aggtacagaa gtccaattgc     1740
ttccgatctg gtaaaagatt cacgagatag taccttctcc gaagtaggta gagcgagtac     1800
ccggcgcgta agctccctaa ttggcccatc cggcatctgt agggcgtcca aatatcgtgc     1860
ctctcctgct ttgcccggtg tatgaaaccg gaaaggccgc tcaggagctg gccagcggcg     1920
cagaccggga acacaagctg gcagtcgacc catccggtgc tctgcactcg acctgctgag     1980
gtccctcagt ccctggtagg cagctttgcc ccgtctgtcc gcccggtgtg tcggcgggt      2040
tgacaaggtc gttgcgtcag tccaacattt gttgccatat ttcctgctc tccccaccag      2100
ctgctctttt cttttctctt tcttttccca tcttcagtat attcatcttc ccatccaaga     2160
```

```
accctttatttt cccctaagta agtactttgc tacatccata ctccatcctt cccatccctt    2220
attcctttga acctttcagt tcgagctttc ccacttcatc gcagcttgac taacagctac    2280
cccgcttgag cagacatcac catggatcca cttaacgtta ctgaaatcat caaacagctt    2340
gacgaatctg gatataagat cgttggtgtc gatgtcagct ccggagttga gacaaatggt    2400
gttcaggatc tcgataagat acgttcattt gtccaagcag caaagagtgc cttctagtga    2460
tttaatagct ccatgtcaac aagaataaaa cgcgttttcg ggtttacctc ttccagatac    2520
agctcatctg caatgcatta atgcattgac tgcaacctag taacgccttn caggctccgg    2580
cgaagagaag aatagcttag cagagctatt ttcattttcg ggagacgaga tcaagcagat    2640
caacggtcgt caagagacct acgagactga ggaatccgct cttggctcca cgcgactata    2700
tatttgtctc taattgtact ttgacatgct cctcttcttt actctgatag cttgactatg    2760
aaaattccgt caccagcncc tgggttcgca aagataattg catgtttctt ccttgaactc    2820
tcaagcctac aggacacaca ttcatcgtag gtataaacct cgaaatcant tcctactaag    2880
atggtataca atagtaacca tgcatggttg cctagtgaat gctccgtaac acccaatacg    2940
ccggccgaaa cttttttaca actctcctat gagtcgttta cccagaatgc acaggtacac    3000
ttgtttagag gtaatccttc tttctagaag tcctcgtgta ctgtgtaagc gcccactcca    3060
catctccact cgacctgcag gcatgcaagc ttggcactgg ccgtcgtttt acaacgtcgt    3120
gactgggaaa accctggcgt tacccaactt aatcgccttg cagcacatcc ccctttcgcc    3180
agctggcgta atagcgaaga ggcccgcacc gatcgccctt cccaacagtt gcgcagcctg    3240
aatggcgaat ggcgcctgat gcggtatttt ctccttacgc atctgtgcgg tatttcacac    3300
cgcatatggt gcactctcag tacaatctgc tctgatgccg catagttaag ccagccccga    3360
cacccgccaa cacccgctga cgcgccctga cgggcttgtc tgctcccggc atccgcttac    3420
agacaagctg tgaccgtctc cgggagctgc atgtgtcaga ggttttcacc gtcatcaccg    3480
aaacgcgcga gacgaaaggg cctcgtgata cgcctatttt tataggttaa tgtcatgata    3540
ataatggttt cttagacgtc aggtggcact ttttcgggga atgtgcgcgg aaccccctatt    3600 tgtttatttt tctaaataca ttcaaatatg tatccgctca tgagacaata accctgataa    3660
atgcttcaat aatattgaaa aaggaagagt atgagtattc aacatttccg tgtcgccctt    3720
attccctttt ttgcggcatt ttgccttcct gttttttgctc acccagaaac gctggtgaaa    3780
gtaaaagatg ctgaagatca gttgggtgca cgagtgggtt acatcgaact ggatctcaac    3840
agcggtaaga tccttgagag ttttcgcccc gaagaacgtt ttccaatgat gagcactttt    3900
aaagttctgc tatgtggcgc ggtattatcc cgtattgacg ccgggcaaga gcaactcggt    3960
cgccgcatac actattctca gaatgacttg gttgagtact caccagtcac agaaaagcat    4020
cttacggatg gcatgacagt aagagaatta tgcagtgctg ccataaccat gagtgataac    4080
actgcggcca acttacttct gacaacgatc ggaggaccga aggagctaac cgcttttttg    4140
cacaacatgg gggatcatgt aactcgcctt gatcgttggg aaccggagct gaatgaagcc    4200
ataccaaacg acgagcgtga caccacgatg cctgtagcaa tggcaacaac gttgcgcaaa    4260
ctattaactg gcgaactact tactctagct tcccggcaac aattaataga ctggatggag    4320
gcggataaag ttgcaggacc acttctgcgc tcggcccttc cggctggctg gtttattgct    4380
gataaatctg gagccggtga gcgtgggtct cgcggtatca ttgcagcact ggggccagat    4440
ggtaagccct cccgtatcgt agttatctac acgacgggga gtcaggcaac tatggatgaa    4500
cgaaatagac agatcgctga gataggtgcc tcactgatta agcattggta actgtcagac    4560
```

-continued

```
caagtttact catatatact ttagattgat ttaaaacttc attttttaatt taaaaggatc    4620 taggtgaaga tccttttttga taatctcatg accaaaatcc cttaacgtga gttttcgttc    4680
cactgagcgt cagaccccgt agaaaagatc aaaggatctt cttgagatcc ttttttttctg   4740 cgcgtaatct gctgcttgca aacaaaaaaa ccaccgctac cagcggtggt ttgtttgccg    4800
gatcaagagc taccaactct ttttccgaag gtaactggct tcagcagagc gcagatacca    4860
aatactgtcc ttctagtgta gccgtagtta ggccaccact tcaagaactc tgtagcaccg    4920
cctacatacc tcgctctgct aatcctgtta ccagtggctg ctgccagtgg cgataagtcg    4980
tgtcttaccg ggttggactc aagacgatag ttaccggata aggcgcagcg gtcgggctga    5040
acggggggtt cgtgcacaca gcccagcttg gagcgaacga cctacaccga actgagatac    5100
ctacagcgtg agctatgaga aagcgccacg cttcccgaag ggagaaaggc ggacaggtat    5160
ccggtaagcg gcagggtcgg aacaggagag cgcacgaggg agcttccagg gggaaacgcc    5220
tggtatcttt atagtcctgt cgggtttcgc cacctctgac ttgagcgtcg attttttgtga   5280 tgctcgtcag gggggcggag cctatggaaa aacgccagca acgcggcctt tttacggttc    5340 ctggccttttt gctggccttt tgctcacatg ttctttcctg cgttatcccc tgattctgtg    5400
gataaccgta ttaccgcctt tgagtgagct gataccgctc gccgcagccg aacgaccgag    5460
cgcagcgagt cagtgagcga ggaagcggaa gagcgcccaa tacgcaaacc gcctctcccc    5520
gcgcgttggc cgattcatta atgcagctgg cacgacaggt ttcccgactg gaaagcgggc    5580
agtgagcgca acgcaattaa tgtgagttag ctcactcatt aggcaccccca ggctttacac   5640 tttatgcttc cggctcgtat gttgtgtgga attgtgagcg gataacaatt tcacacagga    5700
aacagctatg accatgatta cgaattgcgg ccg                                  5733
```

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: PCR
    5' primer

<400> SEQUENCE: 13

```
gtcaaccgcg gactgcgcat catgaagttc ttcgccatc                              39
```

<210> SEQ ID NO 14
<211> LENGTH: 66
<212> TYPE: DNA
<213> ORGANISM: Artificial Sequence
<220> FEATURE:
<223> OTHER INFORMATION: Description of Artificial Sequence: PCR
    5' primer

<400> SEQUENCE: 14

```
tctagcaagc ttggctctag ttctggaacc gcaccaggcg gcagcaacgg caacggcaat     60
gtttgc                                                                 66
```

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: PCR
    3' primer

<400> SEQUENCE: 15

```
tcgtacaagc tttcaagcac cgacggcggt                                    30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 16
tctagctcta gaagcaacgg caacggcaat gtt                                33

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: PCR
      3' primer

<400> SEQUENCE: 17
tgctagtcga cctgctagca gcaccgacgg cggtctg                            37

<210> SEQ ID NO 18
<211> LENGTH: 4614
<212> TYPE: DNA
<213> ORGANISM: Saccharomyces cerevisiae
<220> FEATURE:
<223> OTHER INFORMATION: S. cerevisiae FLO1 coding sequence

<400> SEQUENCE: 18
atgacaatgc ctcatcgcta tatgtttttg gcagtcttta cacttctggc actaactagt    60
gtggcctcag gagccacaga ggcgtgctta ccagcaggcc agaggaaaag tgggatgaat   120
ataaattttt accagtattc attgaaagat tcctccacat attcgaatgc agcatatatg   180
gcttatggat atgcctcaaa aaccaaacta ggttctgtcg gaggacaaac tgatatctcg   240
attgattata atattccctg tgttagttca tcaggcacat ttccttgtcc tcaagaagat   300
tcctatggaa actggggatg caaaggaatg ggtgcttgtt ctaatagtca aggaattgca   360
tactggagta ctgatttatt tggtttctat actaccccaa caaacgtaac cctagaaatg   420
acaggttatt ttttaccacc acagacgggt tcttacacat tcaagtttgc tacagttgac   480
gactctgcaa ttctatcagt aggtggtgca accgcgttca actgttgtgc tcaacagcaa   540
ccgccgatca catcaacgaa ctttaccatt gacggtatca agccatgggg tggaagtttg   600
ccacctaata tcgaaggaac cgtctatatg tacgctggct actattatcc aatgaaggtt   660
gtttactcga acgctgtttc ttggggtaca cttccaatta gtgtgacact tccagatggt   720
accactgtaa gtgatgactt cgaagggtac gtctattcct ttgacgatga cctaagtcaa   780
tctaactgta ctgtccctga ccttcaaat tatgctgtca gtaccactac aactacaacg   840
gaaccatgga ccggtacttt cacttctaca tctactgaaa tgaccaccgt caccggtacc   900
aacggcgttc caactgacga aaccgtcatt gtcatcagaa ctccaacaac tgctagcacc   960
atcataacta caactgagcc atggaacagc acttttacct ctacttctac cgaattgacc  1020
acagtcactg gcaccaatgg tgtacgaact gacgaaacca tcattgtaat cagaacacca  1080
acaacagcca ctactgccat aactacaact gagccatgga acagcacttt tacctctact  1140
tctaccgaat tgaccacagt caccggtacc aatggtttgc aactgatga gaccatcatt  1200
```

```
gtcatcagaa caccaacaac agccactact gccatgacta caactcagcc atggaacgac   1260
acttttacct ctacatccac tgaaatgacc accgtcaccg gtaccaacgg tttgccaact   1320
gatgaaacca tcattgtcat cagaacacca acaacagcca ctactgctat gactacaact   1380
cagccatgga acgacacttt tacctctaca tccactgaaa tgaccaccgt caccggtacc   1440
aacggtttgc caactgatga accatcatt gtcatcagaa caccaacaac agccactact    1500
gccatgacta caactcagcc atggaacgac acttttacct ctacatccac tgaaatgacc   1560
accgtcaccg gtaccaatgg tttgccaact gatgagacca tcattgtcat cagaacacca   1620
acaacagcca ctactgccat gactacaact cagccatgga acgacacttt tacctctaca   1680
tccactgaaa tgaccaccgt caccggtacc aacggtttgc caactgatga accatcatt   1740 gtcatcagaa caccaacaac agccactact gccataacta caactgagcc atggaacagc   1800
acttttacct ctacttctac cgaattgacc acagtcaccg gtaccaatgg tttgccaact   1860
gatgagacca tcattgtcat cagaacacca acaacagcca ctactgccat gactacaact   1920
cagccatgga acgacacttt tacctctaca tccactgaaa tgaccaccgt caccggtacc   1980
aacggtttgc caactgatga accatcatt gtcatcagaa caccaacaac agccactact    2040
gccatgacta caactcagcc atggaacgac acttttacct ctacatccac tgaaatgacc   2100
accgtcaccg gtaccaacgg tttgccaact gatgagacca tcattgtcat cagaacacca   2160
acaacagcca ctactgccat gactacaact cagccatgga acgacacttt tacctctaca   2220
tccactgaaa tgaccaccgt caccggtacc aacggcgttc caactgacga aaccgtcatt   2280
gtcatcagaa ctccaactag tgaaggtcta atcagcacca ccactgaacc atggactggt   2340
actttcacct ctacatccac tgagatgacc accgtcaccg gtactaacgg tcaaccaact   2400
gacgaaaccg tgattgttat cagaactcca accagtgaag gtttggttac aaccaccact   2460
gaaccatgga ctggtacttt tacttctaca tctactgaaa tgaccaccat tactggaacc   2520
aacggcgttc caactgacga aaccgtcatt gtcatcagaa ctccaaccag tgaaggtcta   2580
atcagcacca ccactgaacc atggactggt actttacttt ctacatctac tgaaatgacc   2640
accattactg gaaccaatgg tcaaccaact gacgaaaccg ttattgttat cagaactcca   2700
actagtgaag gtctaatcag caccaccact gaaccatgga ctggtacttt cacttctaca   2760
tctactgaaa tgaccaccgt caccggtacc aacggcgttc caactgacga aaccgtcatt   2820
gtcatcagaa ctccaaccag tgaaggtcta atcagcacca ccactgaacc atggactggc   2880
actttcactt cgacttccac tgaggttacc accatcactg gaaccaacgg tcaaccaact   2940
gacgaaactg tgattgttat cagaactcca accagtgaag gtctaatcag caccaccact   3000
gaaccatgga ctggtacttt cacttctaca tctgctgaaa tgaccaccgt caccggtact   3060
aacggtcaac caactgacga aaccgtgatt gttatcagaa ctccaaccag tgaaggtttg   3120
gttacaacca ccactgaacc atggactggt actttactt cgacttccac tgaaatgtct    3180
actgtcactg gaaccaatgg cttgccaact gatgaaactg tcattgttgt caaaactcca   3240
actactgcca tctcatccag tttgtcatca tcatcttcag acaaatcac cagctctatc    3300 acgtcttcgc gtccaattat taccccattc tatcctagca atggaacttc tgtgatttct   3360
tcctcagtaa tttcttcctc agtcacttct tctctattca cttcttctcc agtcatttct   3420
tcctcagtca tttcttcttc tacaacaacc tccacttcta tttttctga atcatctaaa    3480 tcatccgtca ttccaaccag tagttccacc tctggttctt ctgagagcga aacgagttca   3540
gctggttctg tctcttcttc ctctttttat ctcttctgaat catcaaaatc tcctacatat   3600
```
tcttcttcat cattaccact tgttaccagt gcgacaacaa gccaggaaac tgcttcttca     3660
ttaccacctg ctaccactac aaaaacgagc gaacaaacca ctttggttac cgtgacatcc     3720
tgcgagtctc atgtgtgcac tgaatccatc tcccctgcga ttgtttccac agctactgtt     3780
actgttagcg gcgtcacaac agagtatacc acatggtgcc ctatttctac tacagagaca     3840
acaaagcaaa ccaaagggac aacagagcaa accacagaaa caacaaaaca aaccacggta     3900
gttacaattt cttcttgtga atctgacgta tgctctaaga ctgcttctcc agccattgta     3960
tctacaagca ctgctactat taacggcgtt actacagaat acacaacatg gtgtcctatt     4020
tccaccacag aatcgaggca acaaacaacg ctagttactg ttacttcctg cgaatctggt     4080
gtgtgttccg aaactgcttc acctgccatt gtttcgacgg ccacggctac tgtgaatgat     4140
gttgttacgg tctatcctac atggaggcca cagactgcga atgaagagtc tgtcagctct     4200
aaaatgaaca gtgctaccgg tgagacaaca accaatactt tagctgctga acgactacc      4260 aatactgtag ctgctgagac gattaccaat actggagctg ctgagacgaa acagtagtc      4320 acctcttcgc tttcaagatc taatcacgct gaaacacaga cggcttccgc gaccgatgtg     4380
attggtcaca gcagtagtgt tgtttctgta tccgaaactg gcaacaccaa gagtctaaca     4440
agttccgggt tgagtactat gtcgcaacag cctcgtagca caccagcaag cagcatggta     4500
ggatatagta cagcttcttt agaaatttca acgtatgctg gcagtgccaa cagcttactg     4560
gccggtagtg gtttaagtgt cttcattgcg tccttattgc tggcaattat ttaa           4614

<210> SEQ ID NO 19
<211> LENGTH: 5857
<212> TYPE: DNA
<213> ORGANISM: Saccharomyces cerevisiae and E. coli
<220> FEATURE:
<221> NAME/KEY: promoter
<222> LOCATION: (1)..(452)
<223> OTHER INFORMATION: S. cerevisiae GAL1 promoter
<220> FEATURE:
<221> NAME/KEY: misc_feature
<223> OTHER INFORMATION: (476-495) E. coli T7 promoter/priming site
<220> FEATURE:
<221> NAME/KEY: misc_feature
<223> OTHER INFORMATION: (502-601) E. coli multiple cloning site
<220> FEATURE:
<221> NAME/KEY: misc_feature
<223> OTHER INFORMATION: (609-857) S. cerevisiae CYC1 transcription
      terminator
<220> FEATURE:
<221> NAME/KEY: misc_feature
<223> OTHER INFORMATION: (1039-1712) E. coli pMB1 (pUC-derived) origin
<220> FEATURE:
<221> NAME/KEY: gene
<222> LOCATION: (1857)..(2717)
<223> OTHER INFORMATION: E. coli ampicillin resistance gene
<220> FEATURE:
<221> NAME/KEY: gene
<222> LOCATION: (2735)..(3842)
<223> OTHER INFORMATION: S. cerevisiae URA3 gene
<220> FEATURE:
<221> NAME/KEY: misc_feature
<223> OTHER INFORMATION: (3846-5317) S. cerevisiae 2 micron origin
<220> FEATURE:
<221> NAME/KEY: misc_feature
<223> OTHER INFORMATION: (5385-5840) E. coli f1 origin
<220> FEATURE:
<221> NAME/KEY: misc_feature
<223> OTHER INFORMATION: (1-5857) Sequence of pYES2

<400> SEQUENCE: 19
acggattaga agccgccgag cgggtgacag ccctccgaag gaagactctc ctccgtgcgt       60

-continued

```
cctcgtcctc accggtcgcg ttcctgaaac gcagatgtgc ctcgcgccgc actgctccga      120
acaataaaga ttctacaata ctagctttta tggttatgaa gaggaaaaat tggcagtaac      180
ctggccccac aaaccttcaa atgaacgaat caaattaaca accataggat gataatgcga      240
ttagtttttt agccttattt ctggggtaat taatcagcga agcgatgatt tttgatctat      300
taacagatat ataaatgcaa aaactgcatt aaccacttta actaatactt tcaacatttt      360
cggtttgtat tacttcttat tcaaatgtaa taaaagtatc aacaaaaaat tgttaatata      420
cctctatact ttaacgtcaa ggagaaaaaa ccccggatcg gactactagc agctgtaata      480
cgactcacta tagggaatat taagcttggt accgagctcg gatccactag taacggccgc      540
cagtgtgctg gaattctgca gatatccatc acactggcgg ccgctcgagc atgcatctag      600
agggccgcat catgtaatta gttatgtcac gcttacattc acgccctccc cccacatccg      660
ctctaaccga aaaggaagga gttagacaac ctgaagtcta ggtccctatt tatttttta      720 tagttatgtt agtattaaga acgttattta tatttcaaat ttttcttttt tttctgtaca      780
gacgcgtgta cgcatgtaac attatactga aaaccttgct tgagaaggtt ttgggacgct      840
cgaaggcttt aatttgcggc cctgcattaa tgaatcggcc aacgcgcggg gagaggcggt      900
ttgcgtattg ggcgctcttc cgcttcctcg ctcactgact cgctgcgctc ggtcgttcgg      960
ctgcggcgag cggtatcagc tcactcaaag gcggtaatac ggttatccac agaatcaggg     1020
gataacgcag gaaagaacat gtgagcaaaa ggccagcaaa agcccaggaa ccgtaaaaag     1080
gccgcgttgc tggcgttttt ccataggctc cgcccccctg acgagcatca caaaaatcga     1140
cgctcaagtc agaggtggcg aaacccgaca ggactataaa gataccaggc gtttccccct     1200
ggaagctccc tcgtgcgctc tcctgttccg accctgccgc ttaccggata cctgtccgcc     1260
tttctccctt cgggaagcgt ggcgctttct catagctcac gctgtaggta tctcagttcg     1320
gtgtaggtcg ttcgctccaa gctgggctgt gtgcacgaac cccccgttca gcccgaccgc     1380
tgcgccttat ccggtaacta tcgtcttgag tccaacccgg taagacacga cttatcgcca     1440
ctggcagcag ccactggtaa caggattagc agagcgaggt atgtaggcgg tgctacagag     1500
ttcttgaagt ggtggcctaa ctacggctac actagaagga cagtatttgg tatctgcgct     1560
ctgctgaagc cagttacctt cggaaaaaga gttggtagct cttgatccgg caaacaaacc     1620
accgctggta gcggtggttt ttttgtttgc aagcagcaga ttacgcgcag aaaaaaagga     1680
tctcaagaag atcctttgat cttttctacg gggtctgacg ctcagtggaa cgaaaactca     1740
cgttaaggga ttttggtcat gagattatca aaaaggatct tcacctagat ccttttaaat     1800
taaaaatgaa gttttaaatc aatctaaagt atatatgagt aaacttggtc tgacagttac     1860
caatgcttaa tcagtgaggc acctatctca gcgatctgtc tatttcgttc atccatagtt     1920
gcctgactcc ccgtcgtgta gataactacg atacgggagc gcttaccatc tggccccagt     1980
gctgcaatga taccgcgaga cccacgctca ccggctccag atttatcagc aataaaccag     2040
ccagccggaa gggccgagcg cagaagtggt cctgcaactt tatccgcctc cattcagtct     2100
attaattgtt gccgggaagc tagagtaagt agttcgccag ttaatagttt gcgcaacgtt     2160
gttggcattg ctacaggcat cgtggtgtca ctctcgtcgt ttggtatggc ttcattcagc     2220
tccggttccc aacgatcaag gcgagttaca tgatccccca tgttgtgcaa aaaagcggtt     2280
agctccttcg gtcctccgat cgttgtcaga agtaagttgg ccgcagtgtt atcactcatg     2340
gttatggcag cactgcataa ttctcttact gtcatgccat ccgtaagatg cttttctgtg     2400
actggtgagt actcaaccaa gtcattctga gaatagtgta tgcggcgacc gagttgctct     2460
```

```
tgcccggcgt caatacggga taatagtgta tcacatagca gaactttaaa agtgctcatc    2520
attggaaaac gttcttcggg gcgaaaactc tcaaggatct taccgctgtt gagatccagt    2580
tcgatgtaac ccactcgtgc acccaactga tcttcagcat cttttacttt caccagcgtt    2640
tctgggtgag caaaaacagg aaggcaaaat gccgcaaaaa agggaataag ggcgacacgg    2700
aaatgttgaa tactcatact cttccttttt caatgggtaa taactgatat aattaaattg    2760
aagctctaat ttgtgagttt agtatacatg catttactta taatacagtt ttttagtttt    2820
gctggccgca tcttctcaaa tatgcttccc agcctgcttt tctgtaacgt tcaccctcta    2880
ccttagcatc ccttcccttt gcaaatagtc ctcttccaac aataataatg tcagatcctg    2940
tagagaccac atcatccacg gttctatact gttgacccaa tgcgtctccc ttgtcatcta    3000
aacccacacc gggtgtcata atcaaccaat cgtaaccttc atctcttcca cccatgtctc    3060
tttgagcaat aaagccgata acaaaatctt tgtcgctctt cgcaatgtca acagtaccct    3120
tagtatattc tccagtagat agggagccct tgcatgacaa ttctgctaac atcaaaaggc    3180
ctctaggttc ctttgttact tcttctgccg cctgcttcaa accgctaaca atacctgggc    3240
ccaccacacc gtgtgcattc gtaatgtctg cccattctgc tattctgtat acacccgcag    3300
agtactgcaa tttgactgta ttaccaatgt cagcaaattt tctgtcttcg aagagtaaaa    3360
aattgtactt ggcggataat gcctttagcg gcttaactgt gccctccatg gaaaaatcag    3420
tcaagatatc cacatgtgtt tttagtaaac aaattttggg acctaatgct tcaactaact    3480
ccagtaattc cttggtggta cgaacatcca atgaagcaca caagtttgtt tgcttttcgt    3540
gcatgatatt aaatagcttg gcagcaacag gactaggatg agtagcagca cgttccttat    3600
atgtagcttt cgacatgatt tatcttcgtt tcctgcaggt ttttgttctg tgcagttggg    3660
ttaagaatac tgggcaattt catgtttctt caacactaca tatgcgtata tataccaatc    3720
taagtctgtg ctccttcctt cgttcttcct tctgttcgga gattaccgaa tcaaaaaaat    3780
ttcaaagaaa ccgaaatcaa aaaaagaat aaaaaaaaaa tgatgaattg aattgaaaag    3840
ctagcttatc gatgataagc tgtcaaagat gagaattaat tccacggact atagactata    3900
ctagatactc cgtctactgt acgatacact tccgctcagg tccttgtcct taacgaggc     3960 cttaccactc ttttgttact ctattgatcc agctcagcaa aggcagtgtg atctaagatt    4020
ctatcttcgc gatgtagtaa aactagctag accgagaaag agactagaaa tgcaaaaggc    4080
acttctacaa tggctgccat cattattatc cgatgtgacg ctgcagcttc tcaatgatat    4140
tcgaatacgc tttgaggaga tacagcctaa tatccgacaa actgttttac agatttacga    4200
tcgtacttgt tacccatcat tgaattttga acatccgaac ctgggagttt ccctgaaac     4260 agatagtata tttgaacctg tataataata tatagtctag cgctttacgg aagacaatgt    4320
atgtatttcg gttcctggag aaactattgc atcattgca taggtaatct tgcacgtcgc     4380
atccccggtt catttctgc gtttccatct tgcacttcaa tagcatatct ttgttaacga     4440
agcatctgtg cttcattttg tagaacaaaa atgcaacgcg agagcgctaa ttttccaaac    4500
aaagaatctg agctgcattt ttacagaaca gaaatgcaac gcgaaagcgc tattttacca    4560
acgaagaatc tgtgcttcat ttttgtaaaa caaaaatgca acgcgacgag agcgctaatt    4620
tttcaaacaa gaatctgag ctgcattttt acagaacaga atgcaacgc gagagcgcta     4680 ttttaccaac aaagaatcta tacttctttt tgttctaca aaaatgcatc ccgagagcgc    4740 tattttttcta acaaagcatc ttagattact tttttctccc tttgtgcgct ctataatgca    4800
```

```
gtctcttgat aacttttgc actgtaggtc cgttaaggtt agaagaaggc tactttggtg    4860 tctatttct cttccataaa aaaagcctga ctccacttcc cgcgtttact gattactagc    4920
gaagctgcgg gtgcattttt tcaagataaa ggcatccccg attatattct ataccgatgt    4980
ggattgcgca tactttgtga acagaaagtg atagcgttga tgattcttca ttggtcagaa    5040
aattatgaac ggtttcttct attttgtctc tatatactac gtataggaaa tgtttacatt    5100
ttcgtattgt tttcgattca ctctatgaat agttcttact acaatttttt tgtctaaaga    5160
gtaatactag agataaacat aaaaaatgta gaggtcgagt ttagatgcaa gttcaaggag    5220
cgaaaggtgg atgggtaggt tatataggga tatagcacag agatatatag caaagagata    5280
cttttgagca atgtttgtgg aagcggtatt cgcaatggga agctccaccc cggttgataa    5340
tcagaaaagc cccaaaaaca ggaagattgt ataagcaaat atttaaattg taaacgttaa    5400
tattttgtta aaattcgcgt taaatttttg ttaaatcagc tcattttta acgaatagcc    5460 cgaaatcggc aaaatccctt ataaatcaaa agaatagacc gagataggat tgagtgttgt    5520
tccagtttcc aacaagagtc cactattaaa gaacgtggac tccaacgtca aagggcgaaa    5580
aagggtctat cagggcgatg gcccactacg tgaaccatca ccctaatcaa gttttttggg    5640
gtcgaggtgc cgtaaagcag taaatcggaa gggtaaacgg atgcccccat ttagagcttg    5700
acggggaaag ccggcgaacg tggcgagaaa ggaagggaag aaagcgaaag gagcgggggc    5760
tagggcggtg ggaagtgtag gggtcacgct gggcgtaacc accacacccg ccgcgcttaa    5820
tggggcgcta cagggcgcgt ggggatgatc cactagt                            5857

<210> SEQ ID NO 20
<211> LENGTH: 403
<212> TYPE: DNA
<213> ORGANISM: Trichoderma reesei
<220> FEATURE:
<221> NAME/KEY: misc_feature
<223> OTHER INFORMATION: (1-403) T. reesei hfb2 coding sequence
<220> FEATURE:
<221> NAME/KEY: intron
<222> LOCATION: (131)..(200)
<220> FEATURE:
<221> NAME/KEY: intron
<222> LOCATION: (287)..(358)

<400> SEQUENCE: 20
atgcagttct tcgccgtcgc cctcttcgcc accagcgccc tggctgctgt ctgccctacc      60
ggcctcttct ccaaccctct gtgctgtgcc accaacgtcc tcgacctcat ggcgttgac     120 tgcaagaccc gtatgttgaa ttccaatctc tgggcatcct gacattggac gatacagttg     180
acttacacga tgctttacag ctaccatcgc cgtcgacact ggcgccatct tccaggctca     240
ctgtgccagc aagggctcca agcctctttg ctgcgttgct cccgtggtaa gtagtgctcg     300
caatggcaaa gaagtaaaaa gacatttggg cctgggatcg ctaactcttg atatcaaggc     360
cgaccaggct ctcctgtgcc agaaggccat cggcaccttc taa                       403

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: PCR
    5' primer

<400> SEQUENCE: 21
cggaggagct cgacgacttc gagcagcccg agctgcacgc aggctgtctg ccctaccgg       59
```

```
<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: PCR
      3' primer

<400> SEQUENCE: 22
tcattggatc cttagaaggt gccgatggc                                        29

<210> SEQ ID NO 23
<211> LENGTH: 679
<212> TYPE: DNA
<213> ORGANISM: Schizophyllum commune
<220> FEATURE:
<221> NAME/KEY: misc_feature
<223> OTHER INFORMATION: (1-679) SC3 coding sequence
<220> FEATURE:
<221> NAME/KEY: misc_feature
<223> OTHER INFORMATION: (1-92) 1st cDNA
<220> FEATURE:
<221> NAME/KEY: misc_feature
<223> OTHER INFORMATION: (146-183) 2nd cDNA
<220> FEATURE:
<221> NAME/KEY: misc_feature
<223> OTHER INFORMATION: (240-317) 3rd cDNA
<220> FEATURE:
<221> NAME/KEY: misc_feature
<223> OTHER INFORMATION: (374-469) 4th cDNA
<220> FEATURE:
<221> NAME/KEY: misc_feature
<223> OTHER INFORMATION: (524-586) 5th cDNA
<220> FEATURE:
<221> NAME/KEY: misc_feature
<223> OTHER INFORMATION: (635-679) 6th cDNA

<400> SEQUENCE: 23
atgttcgccc gtctccccgt cgtgttcctc tacgccttcg tcgcgttcgg cgccctcgtc      60
gctgccctcc caggtggcca cccgggcacg acgtacgtcg acctctcacc gtcctctaat     120
gtcttgctga tgaagcccg tatagcacgc cgccggttac gacgacggtg acggtgacca     180
cggtgagtag cttttctcgcc gtcgacgact cgaacgcatt ggctaatttt tgctcatagc     240
cgccctcgac gacgaccatc gccgccggtg gcacgtgtac tacggggtcg ctctcttgct     300
gcaaccaggt tcaatcggta cgtacatcaa agcggcacga ccaggcatct cagctgacgg     360
ccacatcgta caggcgagca gcagcccgt taccgccctc ctcggcctgc tcggcattgt     420
cctcagcgac ctcaacgttc tcgttggcat cagctgctct cccctcactg tgagatcttt     480
ttgttcactg tcccaattac tgcgcactga cagactttgc caggtcatcg gtgtcggagg     540
cagcggctgt tcggcgcaga ccgtctgctg cgaaaacacc caattcgtat gtatactttc     600
catgcgtgtc cctttctccg ctaatcatct gtagaacggg ctgatcaaca tcggttgcac     660
ccccatcaac atcctctga                                                  679

<210> SEQ ID NO 24
<211> LENGTH: 63
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 24
actacacgga ggagctcgac gacttcgagc agcccgagct gcacgcaggg tggccacccg      60
```

```
<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: PCR
      3' primer

<400> SEQUENCE: 25
tcgtacggat cctcagagga tgttgatggg                                      30

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 26
ggaattccgc ggactgcgca tcatgaagtt cttcgccatc gcc                       43

<210> SEQ ID NO 27
<211> LENGTH: 80
<212> TYPE: DNA
<213> ORGANISM: Artificial Sequence
<220> FEATURE:
<223> OTHER INFORMATION: Description of Artificial Sequence: PCR
      3' primer

<400> SEQUENCE: 27
tgaattccat atgttaggta ccaccggggc ccatgccggt agaagtagaa gccccgggag     60
caccgacggc ggtctggcac                                                 80

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 28
tgaattcggt acccaggctt gctcaagcgt c                                    31

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: PCR
      3' primer

<400> SEQUENCE: 29
tgaattccat atgtcacagg cactgagagt agta                                 34

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: PCR
      5' primer
``` ggc                                                                   63

```
<400> SEQUENCE: 30
gaattcggta ccctcgtccc tcgcggtccc gccgaagtga acctggtg                  48

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: PCR
      3' primer

<400> SEQUENCE: 31
tgaattccat atgctaaccc cgtttcatct ccag                                 34

<210> SEQ ID NO 32
<211> LENGTH: 918
<212> TYPE: DNA
<213> ORGANISM: Trichoderma reesei
<220> FEATURE:
<221> NAME/KEY: terminator
<222> LOCATION: (1)..(918)
<223> OTHER INFORMATION: T. reesei hfb1 terminator

<400> SEQUENCE: 32
gatgcccgcc cggggtcaag gtgtgcccgt gagaaagccc acaaagtgtt gatgaggacc     60
atttccggta ctgggaaagt tggctccacg tgtttgggca ggtttgggca agttgtgtag    120
atattccatt cgtacgccat tcttattctc caatatttca gtacactttt cttcataaat    180
caaaaagact gctattctct ttgtgacatg ccggaaggga acaattgctc ttggtctctg    240
ttatttgcaa gtaggagtgg gagattcgcc ttagagaaag tagagaagct gtgcttgacc    300
gtggtgtgac tcgacgagga tggactgaga gtgttaggat taggtcgaac gttgaagtgt    360
atacaggatc gtctggcaac ccacggatcc tatgacttga tgcaatggtg aagatgaatg    420
acagtgtaag aggaaaagga aatgtccgcc ttcagctgat atccacgcca atgatacagc    480
gatataccct caatatctgt gggaacgaga catgacatat ttgtgggaac aacttcaaac    540
agcgagccaa gacctcaata tgcacatcca agccaaaca ttggcaagac gagagacagt    600
cacattgtcg tcgaaagatg gcatcgtacc caaatcatca gctctcatta tcgcctaaac    660
cacagattgt ttgccgtccc ccaactccaa aacgttacta caaaagacat gggcgaatgc    720
aaagacctga aagcaaaccc tttttgcgac tcaattccct cctttgtcct cggaatgatg    780
atccttcacc aagtaaaaga aaagaagat tgagataata catgaaaagc acaacggaaa    840
cgaaagaacc aggaaaagaa taaatctatc acgcacctttg tccccacact aaaagcaaca    900
gggggggtaa aatgaaat                                                  918

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 33
gacctcgatg cccgcccggg gtcaag                                          26

<210> SEQ ID NO 34
<211> LENGTH: 26
<212> TYPE: DNA
<213> ORGANISM: Artificial Sequence
```

```
<220> FEATURE:
<223> OTHER INFORMATION: Description of Artificial Sequence: PCR
      3' primer

<400> SEQUENCE: 34
gtcgacattt cattttaccc ccctcg                                          26

<210> SEQ ID NO 35
<211> LENGTH: 1190
<212> TYPE: DNA
<213> ORGANISM: Trichoderma reesei
<220> FEATURE:
<221> NAME/KEY: promoter
<222> LOCATION: (1)..(1190)
<223> OTHER INFORMATION: T. reesei hfb2 promoter

<400> SEQUENCE: 35
ctcgagcagc tgaagcttgc atgcctgcat cctttgtgag cgactgcatc cattttgcac      60
acactgccgt cgacgtctct cttccgacct tggccagctg acaagcaac acaccaatga     120 cgctttgtat tattagagta tatgcaagtc tcaggactat cgactcaact ctacccaccg    180
aggacgatcg cggcacgata cgccctcgtt ctcattggcc caagcagacc aactgccct    240 ggagcaagat tcagcccaag ggagatggac ggcagggcac gccaggcccc caccaccaag    300
ccactccctt tggccaaatc agcttgcatg tcaagagaca tcgagctgtg ccttgaaatt    360
actaacaacc agggatggga acgaagcct gcttttggaa agacaacaat gagagagaga    420
gagagaggga gagagacaat gagtgccaca aacctggtag tgctccgcca atgcgtctga    480
aatgtcacat ccgagtcttg gggcctctgt gagaatgtcc agagtaatac gtgttttgcg    540
aatagtcctc tttcttgagg actggatacc tacgataccc tttttgagtt gatgcggtgc    600
tttcgaagta ttatctggag gatagaagac gtctaggtaa ctacacaaaa ggcctatact    660
ttggggagta gcccaacgaa aggtaactcc tacggcctct tagagccgtc atagatccta    720
cagcctcttg gagccgtcat agatcacatc tgtgtagacc gacattctat gaataatcat    780
ctcatcatgg ccacatacta ctacatacgt gtctctgcct acctgacatg tagcagtggc    840
caagacacca aggcccagc atcaagcctc cctacctatc ccttccattg tacagcggca    900
gagagattgc gatgagccct ctccctacct acagacggct gacaatgtcc gtataccacc    960
agccaacgtg atgaaaacaa ggacatgagg aacagcctgc gagagctgga agatgaagag   1020
ggccagaaaa aaaagtataa agaagacctc gattcccgcc atccaacaat cttttccatc   1080
ctcatcagca cactcatcta caaccatcac cacattcact caactcctct ttctcaactc   1140
tccaaacaca acattctttt gttgaatacc aaccatcacc acctttcaag              1190

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: PCR
      5' primer

<400> SEQUENCE: 36
aagcttgcat gcctgcatcc                                                 20

<210> SEQ ID NO 37
<211> LENGTH: 26
<212> TYPE: DNA
<213> ORGANISM: Artificial Sequence
<220> FEATURE:
```

<223> OTHER INFORMATION: Description of Artificial Sequence: PCR
      3' primer

<400> SEQUENCE: 37
ccatggtgaa aggtggtgat ggttgg                                              26

<210> SEQ ID NO 38
<211> LENGTH: 13
<212> TYPE: PRT
<213> ORGANISM: Trichoderma reesei
<220> FEATURE:
<221> NAME/KEY: misc_feature
<223> OTHER INFORMATION: vild type T. reesei EGI peptide linker

<400> SEQUENCE: 38

Val Pro Arg Gly Ser Ser Ser Gly Thr Ala Pro Gly Gly
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: modified
      CBHII linker

<400> SEQUENCE: 39

Gly Ser Ser Ser Gly Thr Ala Pro Gly Gly
 1               5                  10

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence:
      Met/Thrombin linker

<400> SEQUENCE: 40

Pro Gly Arg Pro Val Leu Thr Gly Pro Gly Met Gly Thr Ser Thr Ser
 1               5                  10                  15

Ala Gly Pro

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence:
      Met-containing linker

<400> SEQUENCE: 41

Pro Gly Ala Ser Thr Ser Thr Gly Met Gly Pro Gly Gly
 1               5                  10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: linker
      containing the thrombin cleavage site

```
<400> SEQUENCE: 42

Gly Thr Leu Val Pro Arg Gly Pro Ala Gly Val Asn Leu Val
 1               5                  10

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide NheIBgIIINheI of the pTNS15 plasmid

<400> SEQUENCE: 43
gctagagatc tctagc                                                   16

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: synthetic
      peptide AocIXbaIAocI of the pTNS15 plasmid

<400> SEQUENCE: 44

Ala Ser Gly Ala Ser Arg Ala Ser Gly
 1               5

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide AocIXbaIAocI of the pTNS15 plasmid

<400> SEQUENCE: 45
gcctcaggag cctctagagc ttcagga                                       27

<210> SEQ ID NO 46
<211> LENGTH: 20
<212> TYPE: PRT
<213> ORGANISM: Trichoderma reesei

<400> SEQUENCE: 46

Ala Asn Ala Phe Cys Pro Glu Gly Leu Leu Tyr Thr Asn Pro Leu Cys
 1               5                  10                  15

Cys Asp Leu Leu
            20
```

PROCESS FOR PARTITIONING OF PROTEINS

This application is a Divisional of application Ser. No. 09/936,823 (now U.S. Pat. No. 7,060,669, which issued Jun. 13, 2006) filed on Oct. 24, 2001, for which priority is claimed under 35 U.S.C. § 120. Application Ser. No. 09/936,823 is the national phase of PCT International Application No. PCT/FI00/00249 filed on Mar. 24, 2000 under 35 U.S.C. § 371. The entire contents of both above-identified applications are hereby incorporated by reference. This application also claims priority of Application Nos. 990667 and 19991782 filed in Finland on Mar. 25, 1999 and Aug. 20, 1999, respectively, under 35 U.S.C. § 119.

FIELD OF THE INVENTION

The present invention relates to isolation and purification of proteins in aqueous two-phase systems (ATPS). Specifically the invention provides processes for partitioning of molecules of interest in ATPS by fusing said molecules to targeting proteins which have the ability of carrying said molecule into one of the phases.

BACKGROUND OF THE INVENTION

Liquid-liquid extraction in an aqueous two-phase system (ATPS) can offer a powerful technique for isolation and purification of proteins. The separation of macromolecules and particles by means of liquid-liquid extraction is well known (Albertsson, 1986; Walter et al., 1985; Kula, 1990). Mainly polyethylene glycol (PEG)-salt, PEG-dextran and PEG-starch systems have been in use. More recently detergents and detergents with reversed solubility were discovered as suitable methods for separation of macromolecules, and especially for the separation of proteins.

An advantage of aqueous two-phase systems (ATPS) is that they are especially suited for large scale processing of microbial proteins not only from culture supernatants but also from crude extracts containing cells and cell debris (Kula, 1979; Kula, 1985). Characteristic features of biological fluids as well as suspensions are rather small particle sizes, low density differences between fluid and suspended solids, high viscosities of the extracts and high compressibility of the solids (Hustedt et al., 1985; Bender and Koglin, 1986). These attributes decrease the performance of conventional methods for solid-liquid separation like centrifugation and filtration at the beginning of a protein recovery process. Using an aqueous two-phase system removal of solids can be integrated into a liquid-liquid separation step, clarification is thus combined with an initial purification (Kula, 1979; Kula, 1985).

After the extraction process phase separation can be accomplished by settling under gravity as well as by centrifugation (Kula, 1985). ATPS can be applied in various scales from very small laboratory scale to large industrial scale thus suiting for various proteins, purposes and needs. With regard to industrial purposes commercially available centrifugal separators can be used to shorten separation time. Several authors have investigated the potential of centrifugal separators of various design for processing of large volumes of aqueous two phase systems (hula, 1979; Kula et al., 1981; Kula et al., 1982; Kula, 1985). In these studies the authors have used polymer/polymer or polymer/salt systems and the results of these investigations demonstrate the feasibility of continuous separation of aqueous two-phase systems in centrifugal separators.

Extraction systems based on nonionic surfactants have been described as an alternative to standard polymer/polymer or polymer/salt systems. Phase forming surfactants are e.g. polyoxyethylene type nonionic detergents. The basis of this type of aqueous two-phase system is the temperature-dependent reversible hydration of the polar ethylene oxide head groups. The temperature at which the phase separation occurs is referred to as the cloud-point (cloud-point extraction). This kind of aqueous two-phase system is especially suited for the extraction of amphiphilic biomolecules. The potential of this type of two-phase system for separating membrane bound proteins from cytosolic and peripheral membrane proteins was first demonstrated by Bordier (1981). Heusch and Kopp (1988) have been able to demonstrate that lamellar structures formed in the miscibility gaps of polyglycol ether/water systems are responsible for the selective extraction of hydrophobic substances.

Recently, the successful application of a surfactant-based aqueous two-phase system for the extraction of a membrane bound protein (cholesterol oxidase) from the unclarified culture medium of the gram-positive microorganism *Nocardia rhodochrous* on a bench scale has been reported (Minuth et al., 1995). By addition of only one chemical compound a product release through solubilization was possible in homogeneous phase and in a second step a clarification as well as an initial purification was achieved by an extraction process at elevated temperatures separating the detergent rich phase. A closed concept was further developed for the production of the membrane bound enzyme by surfactant-based extraction, organic solvent extraction and anion-exchange chromatography, which gave a product suitable for analytical applications (Minuth et al., 1996).

In aqueous two phase systems the desired target e.g. a protein should partition selectively into one phase (preferentially the lighter phase) while the other substances should partition into the other phase (preferentially the heavier phase). In PEG/salt and PEG/dextran and similar systems there are several driving forces for a substance like charges, hydrophobic, hydrophilic forces or the dependence on conformation or ligand interaction (Albertsson, 1986). The forces leading to separation in detergent based aqueous two phase systems are suggested to be primarily hydrophobic (Terstappen et al., 1993). Even if a lot of work has been carried out in the field of prediction in ATPS, none of the designed models provides a physical picture of the phase behaviour and prediction is hardly possible (Johansson et al., 1998).

In ATPS the partitioning coefficient is defined as the concentration (activity in case of an enzyme) of the target in the top phase divided by the concentration (enzyme:activity) of the target protein in the bottom phase. Partitioning coefficients in ATPS systems are usually in the range from less than 1 up to less than 100 (Terstappen et al., 1992; Terstappen et al., 1993).

$$K = \frac{c_{i,T}}{c_{i,B}}$$

Yield: is defined as the amount of target in the top phase divided by the sum of the amount of target in top and bottom. This leads to the following equation $$Y_T = \frac{1}{1 + \left[\frac{V_B}{V_T} \cdot \frac{1}{K}\right]}$$

If the desired substance is directed to the heavier phase (as it can be the case using Triton) the yield is defined by $$Y_B = \frac{1}{1 + \left[\frac{V_T}{V_B} \cdot K\right]}$$

The volume ratio of the two coexisting phases are defined by the volumes of the lighter over the heavier phase, respectively.

$$R = \frac{V_T}{V_B}$$

An example of useful proteins facing problems in purification in a cost-effective way are the commonly used industrial enzymes used as biocatalysts, the glycosyl hydrolases, proteases and lipases produced by fungi and bacteria. These are used in e.g. laundry, textile, paper and pulp, food and feed industry. The fact that microbes produce many different enzymes during their growth and the fact that some of these may be undesired in certain applications leads to a need to enrich the active component(s). This enrichment can be performed by choosing appropriate growth conditions, by genetic engineering and/or by down-stream processing (e.g. purification of the active component(s)).

Purification of proteins are generally performed by chromatography. Usually gel-chromatographic methods are used based on ion-exchange, hydrophobic interaction, affinity chromatography and molecular sieving. Methods like electrophoresis and crystallisation can also be used. These methods are well known in the art and suitable for proteins of fairly high market value. In case of bulky enzyme production these methods, however, are too expensive in order to keep the final product on a compatible price level. Due to similar properties of these enzymes several purification steps are usually needed to separate the proteins from each other. This often causes low final yields and therefore a high loss of product.

Many extracellular hydrolases produced by the filamentous fungus *Trichoderma* are currently used in different industrial applications in large scale. These hydrolases are e.g. hemicellulases (such as xylanases and mannanases), cellulases (such as endoglucanases and cellobiohydrolases) and proteases. Purification of these is well known in the art (Bhikhabhai et al., 1984; Pere et al., 1995), but for large industrial applications the purification methods are too expensive. Alternative methods to enrich these hydrolases have been used, including deletion of undesired genes by genetic engineering (Suominen et al., 1992). However, even after extensive genetic engineering some minor undesired activities may still be present in the final product.

ATPS have been studied in purification of cellulases of *T. reesei* and the purification of an endoglucanase III showed some promising results, enriching the yield of the protein in the upper phase (U.S. Pat. No. 5,139,943). ATPS have also been studied in purification of lipases, endoxylanase and natamycin (EP 0 574 050 A1). No K and Y values are, however, mentioned.

As in other protein purification methods, similar properties of proteins produced by an organism impair also in ATPS, e.g. selective separation of one protein is not achieved optimally. To obtain selectivity in purification affinity chromatographic methods are used especially for analytic purposes and in purification of high-value products. These include immunoaffinity chromatography and various fusion protein strategies well described in the art such as fusing the protein of interest to an other protein (e.g. glutathione-S-transferase), protein domain (e.g. protein A-ZZ domain) or small peptide (e.g. His-tag), which selectively bind to the solid carrier and thus the recovery of the fusion partner is obtained as well. The fusion protein can be suitable for the particular purpose as such or cleavage of the product from the added fusion partner may be desired. There are well-known methods in the art on cleavage of fusion proteins from their partners by proteases, e.g. by factor X, thrombin or papain or by genetically introducing a protease cleavage site (e.g. Kex2 site) or autoprocessing domains (e.g. Intein, New England Biolabs) or by chemical cleavage (e.g. CNBr).

ATPS offer advantages mainly with respect to technology compared with the solid state based separation systems e.g. affinity column-based techniques. The scale-up of extractive enzymes is relatively simple utilising commercially available equipment and machinery common in the chemical industry. In addition, it can be used in a continuous process and it can be relatively cost extensive. It can be used as a single step for clarification, concentration and purification. ATPS can be used as a first capture-step, but for bulk products often no further purification is needed.

To aid selective separation in two-phase systems, recent publications have described the fusion of small peptide tags of 12 amino acids to the protein to be purified. The most successful of these soluble peptides are containing tryptophans. So far they have mainly been applied for very small molecules like the staphylococcal protein A derivative ZZT0 (Berggren et al., 1999; Hassinen et al., 1994; Köhler et al., 1991).

Use of ATPS has so far been limited to certain targets. Due to the advantages of ATPS in protein separation, purification and localisation, highly selective and powerful methods should be developed. This is especially important for large scale processes where ATPS in general is very inexpensive as a first capture step or as the only step for purification, clarification and concentration. The system should be universal so that the technique would be strong enough to mediate separation of in principle any component to the desired phase irrespective of its size or biochemical properties.

DESCRIPTION OF THE INVENTION

In this invention we describe selective separation and partitioning of molecules and particles fusing them with targeting proteins having the capability to carry the molecule or particle of interest to the desired phase in ATPS, and to keep it in this phase if wanted. This invention is directed to make ATPS usable for every biotechnological product. By addition of the targeting protein to selective products, either by genetic tagging of proteins, by chemical binding, glueing or by use of any other technique, the product molecule can be turned more suitable for separation in ATPS. Using ATPS the product or certain component is therefore driven to one phase while the other components or by-products are directed to the other phase(s).

We also describe that efficient separation in ATPS can be obtained using targeting proteins which are/can be larger than the described small soluble synthetic peptide tags of 12 amino acids or less. These targeting molecules can aid in separating of small molecules but even large proteins and particles. Unlike the small peptide tags, it is not necessary that they contain tryptophan residues, although they may do so. They can be hydrophobic or moderately hydrophobic and/or amphipathic in nature, either in monomeric form or when forming aggregates. Such proteins can be found in nature or they can be designed, or obtained through for instance methods known in art for mutant generation, gene shuffling or directed evolution. Suitable targeting molecules can be screened for instance by fusion the product of interest to a library of natural or mutant sequences, and screening the ability of the fusion molecules to separate in ATPS. Furthermore, any molecule capable of separating in ATPS is a suitable targeting molecule.

Several techniques exploiting purified protein for isolation of the corresponding gene may be used to find genes encoding suitable targeting molecules for ATPS. Suitable proteins or polypeptides may be purified on the basis of their properties. They can be obtained by applying the cells, cell extracts or culture media to ATPS and recovering the proteins or peptides separated into the phase containing the hydrophobic phase material. Suitable targeting molecules may also be recovered for example from the culture medium foam formed either during the cultivation of a microorganism or caused by bubbling gas through the medium. Proteins and peptides suitable as targeting molecules may further be recovered from aggregates caused by freezing of culture media. After the targeting molecules have been purified, the corresponding genes are isolated using techniques known to a person skilled in the art. Such techniques include for example screening of expression libraries using antibodies raised against purified polypeptide or peptide, and PCR cloning and screening of genomic and/or cDNA libraries with oligonucleotides designed on the basis of N-terminal or internal protein sequences.

Examples of molecules suited as targeting proteins in ATPS found in nature are hydrophobin-like small proteins. Hydrophobins are secreted proteins with interesting physico-chemical properties that have recently been discovered from filamentous fingi (Wessels, 1994; Wösten and Wessels, 1997; Kershaw and Talbot, 1998). They are usually small proteins, approximately 70 to 160 amino acids, containing eight cysteine residues in conserved pattern, and do usually not contain tryptophans. However, also multimodular proteins with one or several hydrophobin domains and e.g. proline-rich or asparagine/glycine repeats, or hydrophobins containing less than eight cysteine residues have been characterized (Lora et al., 1994; Lora et al., 1995; Arntz and Tudzynski, 1997). Hydrophobins have been divided into two classes based on their hydropathy profiles (Wessels, 1994).

Today most protein data exists for the hydrophobins Sc3p of *Schizophyllum commune* (class I), and cerato-ulmin of *Ophiostoma ulmi* and cryparin of *Cryponectria parasitica* (class II), although more than 30 gene sequences for hydrophobins have been published (Wösten and Wessels, 1997). HFB genes are often naturally highly expressed but due to special requirements in cultivation conditions and the biochemical properties of the proteins, purification of HFBs in large amounts have been difficult. For instance only relatively moderate production levels of a few mg per liter of Sc3 hydrophobin in static cultures are obtained (Han Wösten, personal communication). Published purification procedures include e.g. multi-step extraction from fungal cell walls using organic solvents and bubbling or freezing of culture filtrates (Wessels, 1994). No reports of successful production of hydrophobins are available; levels of ceratoulmin were no higher than those obtained with other naturally occurring fungal isolates (Temple et al., 1997).

Upon shaking hydrophobin-containing solutions, the protein monomers form rodlet-like aggregates. These structures are similar to the ones found on surfaces of aerial structures. The self-assembly of purified Sc3 hydrophobin into a 10 nm thick amphipatic layer on hydrophilic and hydrophobic surfaces has been demonstrated (Wösten et al., 1994a; Wösten et al., 1994b). This film is very strongly attached to the surface and not broken, for instance, by hot detergent. The hydrophobic side of the layer on hydrophilic surfaces shows properties similar to teflon (Wessels, 1994). The Sc3 assemblages, as well as those of cerato-ulmin and cryparin, also form on gas-liquid or gas-air interphases thus stabilizing air bubbles or oil droplets in water.

Surface activity of proteins is generally low but hydrophobins belong to surface-active molecules, their surfactant capacity being at least similar to traditional biosurfactants such as glycolipids, lipopeptides/lipoproteins, phospholipids, neutral lipids and fatty acids (Wösten and Wessels, 1997). In fact Sc3 hydrophobin is the most potent biosurfactant known. It lowers the water surface tension to 24 mJm$^2$ at a concentration of 50 µg/ml due to a conformational change during self-assembly of monomers into an amphipathic film (Wösten and Wessels, 1997).

Hydrophobin-like molecules vary in their properties. For instance, rodlet-forming capacity has not been assigned for all hydrophobins (such as some class II), or they might have a weaker tendency to form stable aggregates Russo et al., 1992; Carpenter et al., 1992). Another group of fungal amphiphatic proteins are repellents (Wösten et al., 1996 (Ustilago), for review, see Kershaw and Talbot, 1998). Consequently, other type of proteins suited as targeting proteins for ATPS, may have only some of the features assigned to hydrophobins. Other suitable proteins are hydrophobic ones such as e.g. lipases, cholesterol oxidase, membrane proteins, small peptide drugs like nisin, aggregating cell wall proteins, lipopeptides or any parts of these or combinations of these, and other molecules like glycolipids, phospholipids, neutral lipids, fatty acids in combination with proteins or peptides.

In this invention the targeting protein, such as a hydrophobin-like protein or parts of it, is bound to the product molecule or the component to be separated. First, phase forming materials and eventually possibly also additional salts are added to a watery solution containing the fusion molecule or component, and optionally also the contaminating materials. The added agents are mixed to facilitate their solubilization. As soon as they are solubilized the two phase are formed either by gravity settling or centrifugation. In the separation the targeting protein drives the product to for instance the detergent-rich phase which could either be the top or the bottom phase. The method is not only useful for purification of products of interest but also for keeping the product or the component of interest, such as a biocatalyst, in a particular phase which enables certain useful biotechnical reactions.

Several ATPS systems are suitable for performing this invention. These include PEG containing systems, detergent based systems and novel thermoseparating polymers. Detergent based systems can be nonionic, zwitterionic, anionic or kationic. The system can be based on amphiphilic polymeric detergents, micelle forming polymers. Novel polymers can be based on polyethylene-polypropylene copolymers such as pluronic block copolymers, Brij, polyoxyethylene derivatives of partial ethers of fatty acids made by adding polyoxyethylene chains to the nonesterified body and polyoxyethylene derivatives. The well known PEG/salt, PEG/dextran and PEG/starch (or derivatives such as Reppal, hydroxypropyl starch) systems where PEG and water are forming the top phase and dextran/starch/salt and water are forming the bottom phase. As salts are used phosphate, citrate, sulfate or others. In the present process the target is partitioning mainly to the top phase, while most of the contaminants are separating mainly to the bottom phase. Some hydrophobic contaminants might partition to the top phase as well. Using detergent based systems only one phase forming detergent has to be added. Optionally, salts and other chemicals can be used in addition. The mentioned chemicals are added, and the solution is mixed. After mixing the separation can take place either by centrifugation or gravity settling. In order to separate into two phases the temperature of the solution has to be over the cloud-point of the detergent. The solution has to be heated if the cloud-point is not reached otherwise. If wanted, a second separation step can follow after a first extraction step and the product rich phase can be further purified. Also the remaining product in the product poor and by-product rich phase can be re-extracted. Very good K values can be obtained and the yields and concentration factors are high.

The process of the present invention can advantageously be used in laboratory scale but is especially suitable for large scale separations. It can successfully be used in the separation of proteins and components from large fermentations. Using genetic modifications, the method can be used to purify any protein of interest including extracellular enzymes and proteins such as cellulases and hemicellulases from mixtures containing large amounts of protein such as several grams per liter. Furthermore, this separation can be obtained from various culture media including industrial media containing particular materials such as cellulose and spent grain. The method can be used to purify the product from culture media of strains modified not to produce endogenous hydrophobins. The separation can be done directly from the fermentation broth which can additionally contain cells, even viscous filamentous fungi. High biomass levels are acceptable for the process as explained in example 9. An example is the extracellular endoglucanase I from the fungus Trichoderma reesei which can be tagged for instance with the class 2 hydrophobin I (HFBI) and can for example be separated with the nonionic polyoxyethylene C12-C18EO5. In this example the detergent rich phase is the lighter phase and contains most of the tagged endoglucanase while most of the other cellulases, proteases and other enzymes remain in the heavier phase. The mycelium separates to the bottom phase, too. The separation can be achieved using separation temperatures higher than 25° C. The temperature can be decreased if certain salts like NaCl or $K_2SO_4$ are added.

The invention describes separation of molecules produced in various different organisms such as bacteria, yeast and filamentous fungi. The invention is suitable for purification of product molecules from extra- or intracellular locations, including cell wall bound molecules. It provides examples how the fusion molecule can be secreted by these different organisms but also provide an example how the fusion can be produced intracellularly.

The invention further describes how fusion molecules consisting of several domains can be constructed and successfully expressed and produced. The invention describes fusions of the targeting molecule to a small protein (CBD), to a moderately sized protein (EGI) and to a huge highly glycosylated protein (FloI), and different domain variations of these. These molecules can be ready as such for biotechnical use. Alternatively, the product can be cleaved from the targeting protein by any method known in the art such as with proteases e.g. thrombin, factor X, papain or by chemical cleavage. Furthermore, ATPS is a preferential means to be used to separate the product from the targeting protein after cleavage, or these can be separated with other methods known in the art.

A surprising feature is that the targeting protein can also be used to carry large particles to the desired phase in ATPS. This can be obtained if the particles already contain proteins suited for targeting such as spores/conidia do in case of fungi. The targeting protein can also be attached to the particles or compounds in vitro. If cells are separated, the targeting protein can alternatively be expressed in the recombinant cells in such a way that it is exposed at the cell surface whereby it mediates the separation of the cells in ATPS. A teaching how this can be done is provided in example 22. Other types of molecules which direct the targeting molecule to the cell surface can be found e.g. in the literature including bacterial outer membrane proteins and lipoproteins (Ståhl and Uhlén, 1997), and yeast proteins α-agglutinin and flocculin (Schreuder et al., 1996; Klis et al. (1994) WO 94/01567; Frenken (1994) WO 94/18330).

A further advantage of the system is that the invention combined with ATPS provides a means to separate the product or desired component not only from other unnecessary or unwanted proteins but also from harmful proteins such as proteases as described in example 6. Thus, the invention is particularly suited for production and purification of heterologous proteins, e.g. sensitive mammalian proteins usually produced in limited amounts in heterologous hosts. Such proteins are for instance antibodies or fragments thereof, interferon, interleukin, oxidative enzymes and any foreign protein which can otherwise be produced in a host. It is possible that separation of the product from e.g. culture medium can also be obtained on-line or semi-continuously, thus minimising the effect of proteases or other harmful components present in the culture. When produced intracellularly, the invention also provides means to separate the heterologous product, for instance the inclusion bodies it may form, from the cellular extracts.

This invention describes for the first time that fusion proteins containing hydrophobin-like molecules can be made and produced in significant amounts despite the very particular properties of hydrophobin-like molecules. Importantly, this invention also describes how recombinant strains producing increased amounts of hydrophobin-like proteins as such can be made. This provides means to produce the targeting protein for uses in which it is wanted that the targeting protein is bound to the product or particle in vitro, to enable further separation of such molecules or particles in ATPS.

Importantly, this invention also describes how hydrophobin-like molecules can be purified in ATPS very efficiently with high K-values. The molecules can be separated in the same way as the above mentioned fusions, for instance by PEG systems of by detergent-based systems. Separation can be done from the culture medium or from cells. This provides a significant improvement in making pure preparates containing hydrophobin-like molecules since due to their properties their purification is very complicated and results in losses with the previously reported techniques as described above.

The invention is further illustrated by the following Examples which describe construction of the fusion molecules of the invention, and partitioning of the molecules of interest using the process according to the invention.

EXAMPLES

Example 1

Construction of Vectors for Expression of EGI and EGIcore HFBI Fusion Proteins Under the cbh1 and gpd1 Promoters of *Trichoderma* and gpdA Promoter of *Asperigillus*

For construction of an EGI-HFBI fusion protein, hfb1 (SEQ ID NO: 1) coding region (from Ser-23 to the STOP codon) and a peptide linker (Val Pro Arg Gly Ser Ser Ser Gly Thr Ala Pro Gly Gly) (SEQ ID NO: 38) preceding it was amplified with PCR using pTNS9 as a template and as a 5' primer TCG GG <u>CACTACGTG</u> C CAG TAT AGC AAC GAC TAC TAC TCG CAA TGC CTT GTT CCG CGT GGC TCT AGT TCT OGA ACC GCA (SEQ ID NO:2) and as a 3' primer TCG TAC <u>GGATCC</u> TCA AGC ACC GAC GGC GGT (SEQ ID NO:3). pTNS9 has been described in detail in Example 19. The sequence in bold in the 5' primer encodes 16 C-terminal residues of EGI. The sequence in italics is a thrombin cleavage site and the underlined CAC-TACGTG is a DraIII site. The underlined GGATCC in the 3' primer is a BamHI site. The 280 bp PCR fragment was purified from agarose gel and ligated to pGEM-T T/A vector (Promega) resulting in pMQ102.

For construction of an EGIcore-HFBI fusion protein, the hfb1 coding region (as above) was amplified with PCR using pTNS9 as a template and as a 5' primer ACT ACA CGG AG <u>GAGCTC</u> G ACG ACT TCG AGC AGC CCG AGC TGC ACG CAG AGC AAC GGC AAC GGC (SEQ ID NO:4) and as a 3' primer SEQ ID NO:3. The sequence in bold in the 5' primer encodes amino acids 410-425 in EGI and the underlined GAGCTC is a SacI site. The 260 bp PCR fragment was purified from agarose gel and ligated to pPCRII T/A vector (Invitrogen) resulting in pMQ111.

Figure 1:
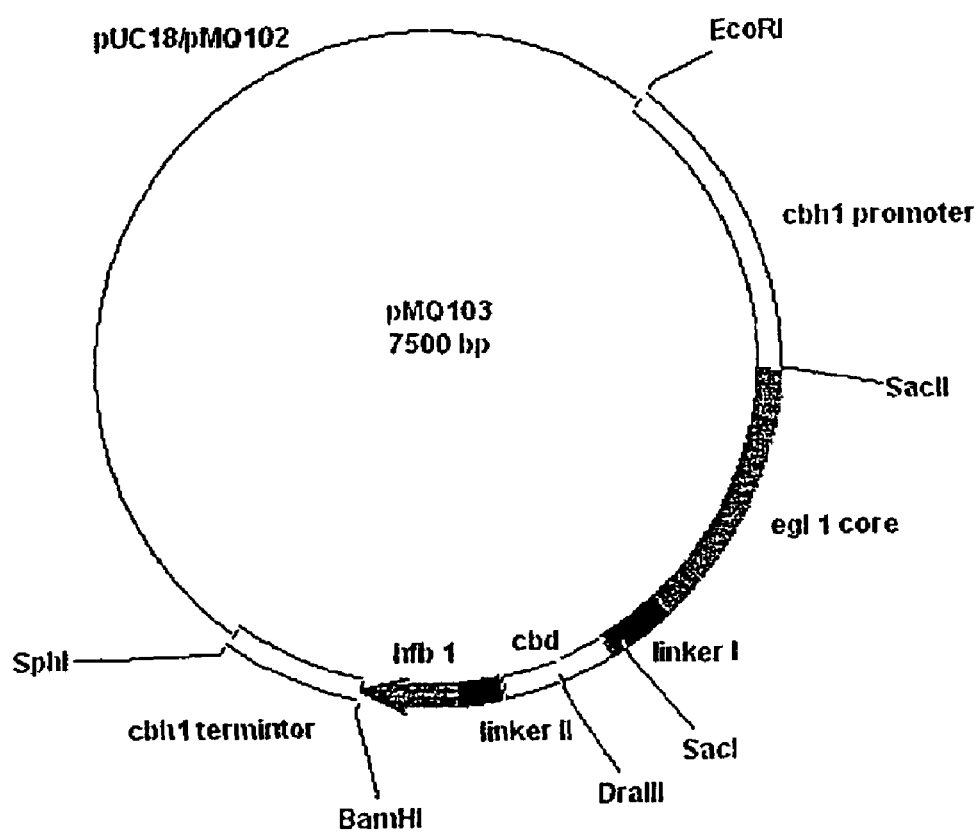
FIG. 1 shows the map of the plasmid pMQ103.
Figure 2:
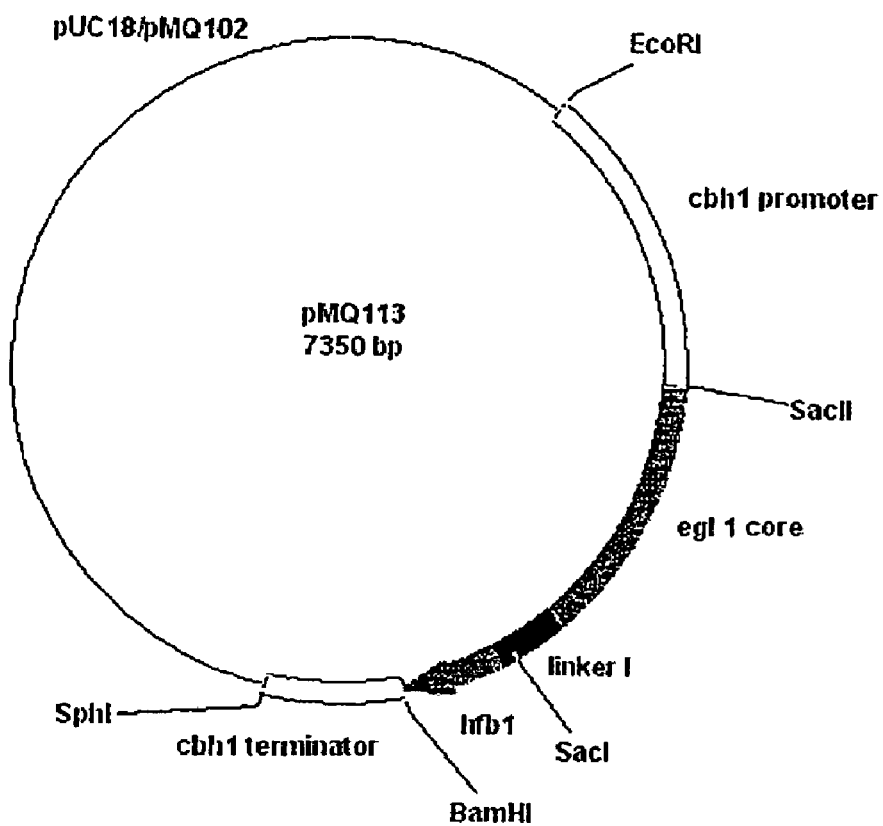
FIG. 2 shows the map of the plasmid pMQ113.

In the next step *Trichoderma* expression vectors for production of EGI-HFBI and EGIcore-HFBI fusion proteins under the control of cbh1 promoter and terminator sequences were constructed. The expression vector used as a backbone in the constructs is pPLE3 (Nakari et al. (1994) WO 94/04673) which contains a pUC18 backbone, and carries the cbh1 promoter (SEQ ID NO:5) inserted at the EcoRI site. The cbh1 promoter is operably linked to the full length egl1 cDNA (SEQ ID NO:6) coding sequence and to the cbh1 transcriptional terminator (SEQ ID NO:7). The plasmid pMQ102 was digested with DraIII and BamHI and the released 280 bp fragment containing hfb1 and linker sequences was purified from agarose gel and ligated to pPLE3 digested with DraIII and BamHI. The plasmid pMQ111 was digested with SacI and BamHI and the 260 bp fragment containing the hfb1 sequence was ligated to pPLE3 digested with SacI and BamHI. The resulting plasmids pMQ103 (FIG. 1) and pMQ113 (FIG. 2) carry the coding sequences for full-length EGI linked to BFBI via a peptide linker and for EGIcore linked to HFBI via its own linker region, respectively, under the control of cbh1 promoter and terminator sequences.

Figure 3:
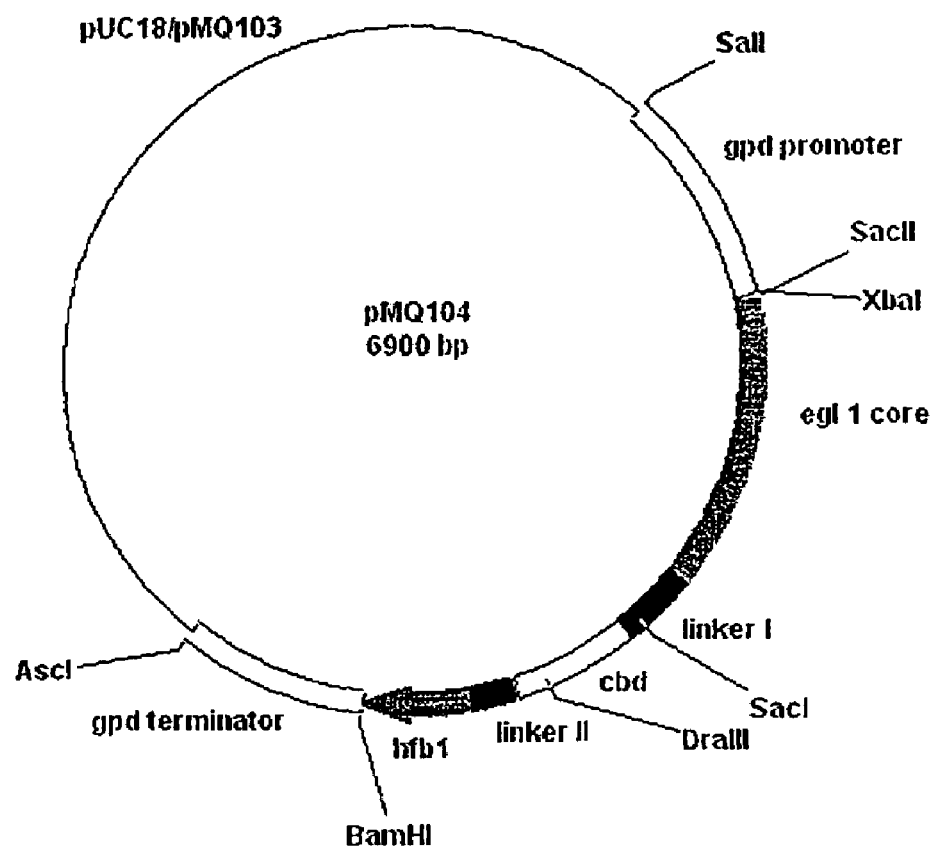
FIG. 3 shows the map of the plasmid pMQ104.
Figure 4:
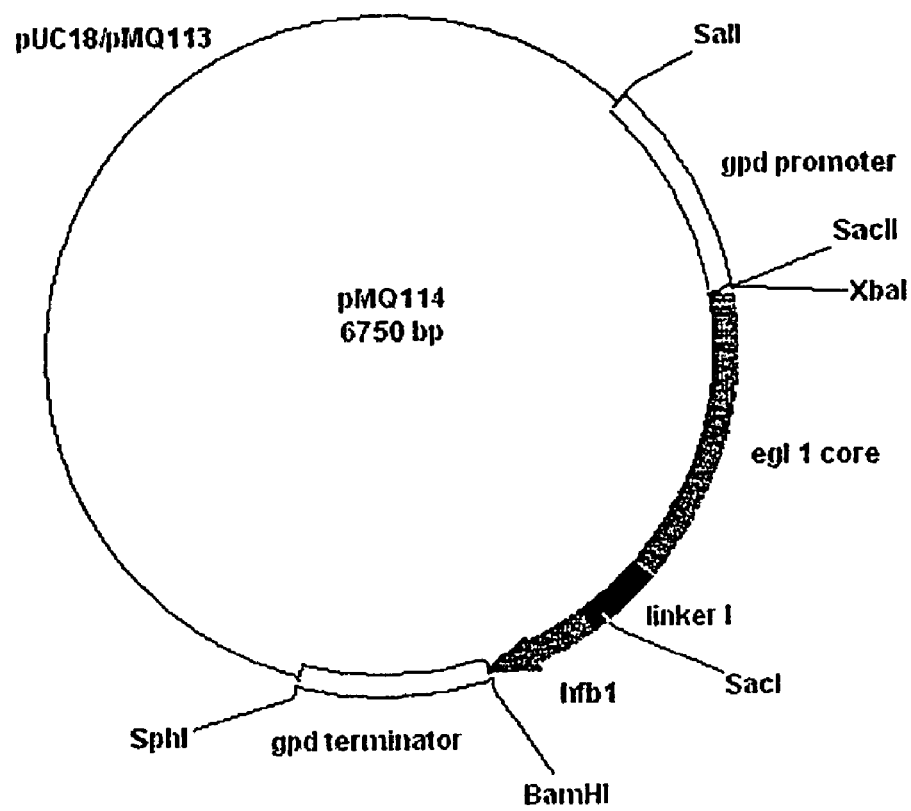
FIG. 4 shows the map of the plasmid pMQ114.
Figure 5:
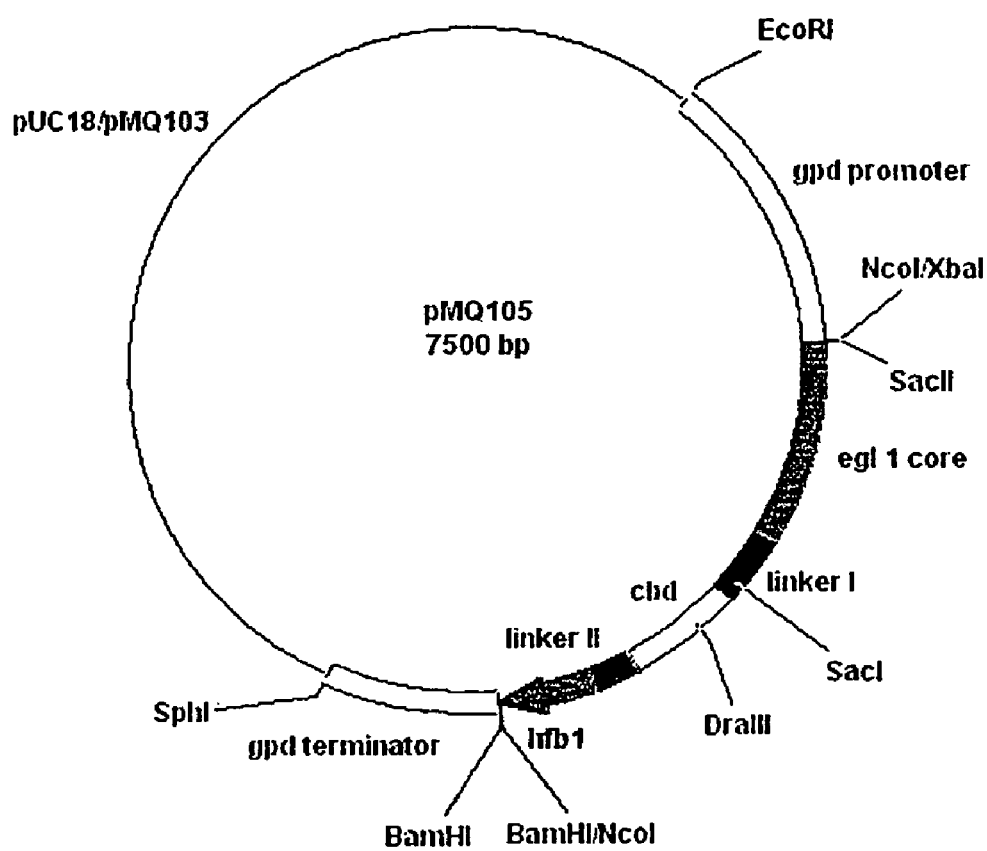
FIG. 5 shows the map of the plasmid pMQ105.
Figure 6:
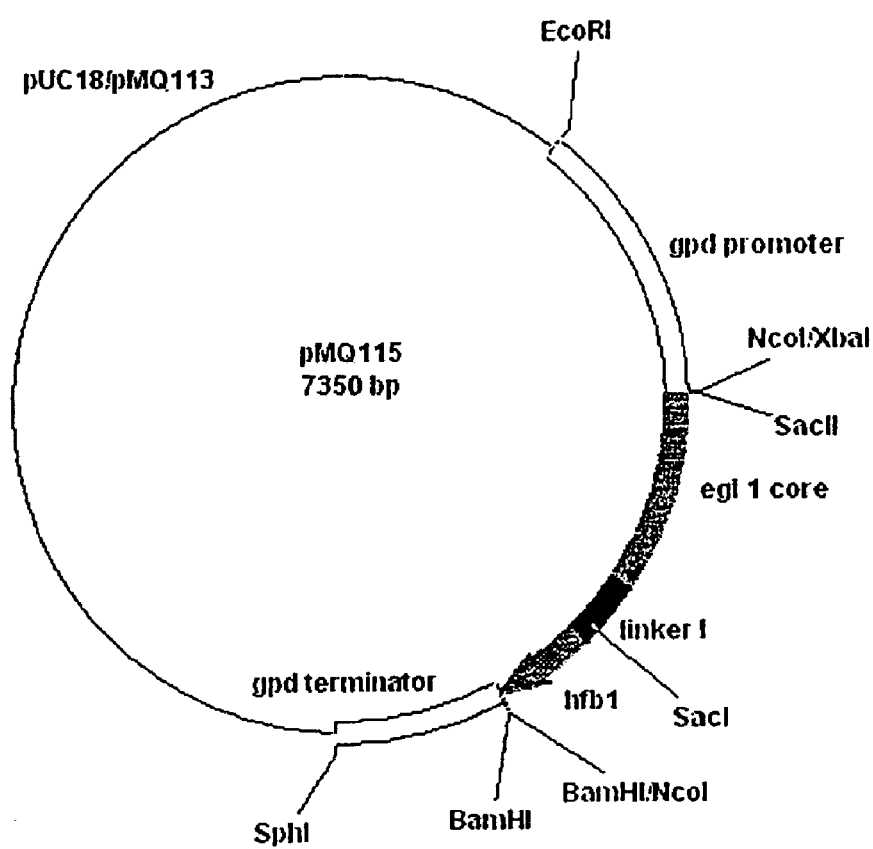
FIG. 6 shows the map of the plasmid pMQ115.

*Trichoderma* expression vectors for production of EGI-HFBI and EGIcore-HFBI fusion proteins under the control of gpd1 promoter and terminator sequences of *Trichoderma* and gpM4 promoter and trpC terminator sequences of *Aspergillus* were constructed as follows. A SacII site was inserted inbetween the XbaI and PacI sites of pMV4 using as an adapter annealed primers TAA CCG CGG T (SEQ ID NO:8) and CTA GAC CGC GGT TAA T (SEQ ID NO:9). The resulting plasmid is pMVQ. pMV4 contains a pNEB193 (New England Biolabs) backbone, and carries a 1.2 kb *Trichoderma* gpd1 promoter (SEQ ID NO:10) and a 1.1 kb gpd1 terminator (SEQ ID NO:11) inserted at SalI-XbaI and BamHI-AscI sites, respectively. The expression cassettes for EGI-HFBI and EGIcore-HFBI were released from pMQ103 and pMQ113 with SacII and BamHI, purified from agarose gel and ligated to pMVQ cut with SacII and BamHI. The resulting plasmids pMQ104 (FIG. 3) and pMQ114 (FIG. 4) carry the EGI-HFBI and EGIcore-HFBI cassettes, respectively, under the control of *Trichoderma* gpd1 transcriptional control sequences. Expression plasmids pMQ105 (FIG. 5) and pMQ115 (FIG. 6) containing EGI-HFBI and EGIcore-HFBI cassettes, respectively, operably linked to the gpdA promoter and trpC terminator of *Aspergillus* were constructed. EGI-HFBI and EGIcore-HFBI cassettes were released from plasmids pMQ104 and pMQ114 with XbaI and BamHI, blunted with T4 DNA polymerase and ligated to NcoI digested and T4 DNA polymerase treated pAN52-1 (SEQ ID NO: 12). pAN52-1 contains a pUC18 backbone, and carries a 2.3 kb gpdA promoter and a 0.7 kb trpC terminator sequences of *A. nidulans*.

Example 2

Figure 7:
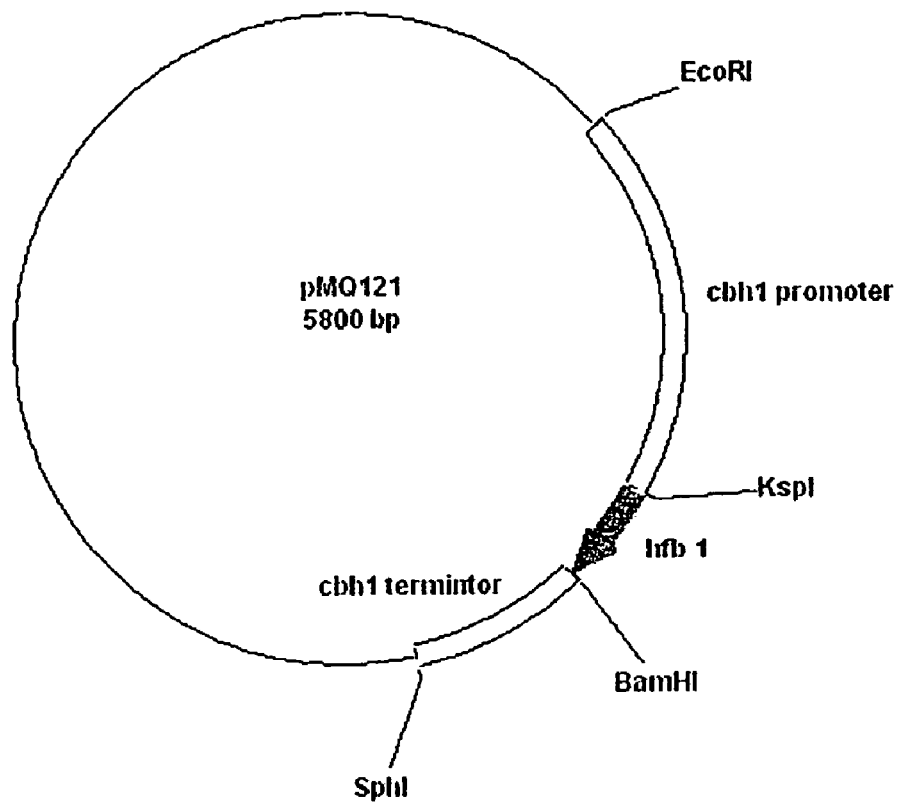
FIG. 7 shows the map of the plasmid pMQ121.

Construction of Vectors for Over-Production of HFBI on Cellulase-Inducing and -Repressing Media For over-expression of HFBI under cbh1 promoter the protein coding region of hfb1 was amplified with PCR using as a template pEA10 (Nakari-Setälä et al., 1996). pEA10 carries a 5.8 kb genomic SalI fragment containing hfb1 coding and flanking sequences. GTC AA CCGCGG A CTG CGC ATC ATGAAGTTC TTC GCC ATC (SEQ ID NO:13) was used as a 5' primer in the PCR and as a 3' primer SEQ ID NO:3. The sequence in bold in the 5' primer is 21 bp of cbh1 promoter adjacent to translational start site of the corresponding gene and the underlined CCGCGG is a KspI site. The obtained fragment of 430 bp was digested with KspI and BamHI and ligated to pMQ103 digested with KspI and BamHI. The resulting plasmid pMQ121 (FIG. 7) carries the coding sequence of hfb1 operably linked to cbh1 transcriptional control sequences. pEA10 plasmid is used for over-production of HFBI in cellulase-repressing conditions.

Example 3

Transformation of *Trichoderma* and Purification of the EGI-HFBI and EGIcore-HFBI Producing and HFBI Over-Producing Clones

*Trichoderma reesei* strains QM9414 (VTT-D-74075) and Rut-C30 (VTT-D-86271) were co-transformed essentially as described (Penttilä et al., 1987) using 3-13 μg of the plasmids pMQ103, pMQ113, pMQ104, pMQ114, pMQ105, pMQ115, pMQ121 and pEA10 and as the selection plasmids 1-3 μg pToC202, p3SR2 or pARO21. pToC202 (pUC19 backbone) and p3 SR2 (pBR322 backbone) plasmids carry 2.7 kb XbaI and 5 kb EcoRI-SalI genomic fragments of *A. nidulans*, respectively, containing the amdS gene (Hynes et al., 1983; Tilburn et al., 1983). pARO21 is essentially the same as pRLMex30 (Mach et al. 1994) and carries the *E. coli* hph gene operably linked to 730 bp of pki1 promoter and 1 kb of cbh2 terminator sequences of *T. reesei*. The Amd+ and Hyg+ transformants obtained were streaked three times onto plates containing acetamide and hygromycin, respectively (Penttilä et al., 1987). Thereafter spore suspensions were made from transformants grown on Potato Dextrose agar (Difco).

The production of the fusion proteins EGI-HFBI and EGIcore-HFBI and BFBI was tested by slot blotting or Western analysis with EGI and HFBI specific antibodies from she flask or microtiter plate cultivations carried out in minimal medium supplemented with either glucose, lactose or a mixture of Solka flock cellulose and/or spent grain and/or whey. The spore suspensions of the fusion protein producing clones were purified to single spore cultures on selection plates (containing either acetamide or hygromycin). To determine the best producers, production of the fusion proteins was analyzed again from these purified clones as described above.

*T. reesei* strains selected for further fermentor cultivations are VTT-D-98692 (pEA10), VTT-D-98492 (pMQ121), VTT-D-98693 (pMQ103), VTT-D-98691 (pMQ113), VTT-D-98681 (pMQ105) and VTT-D-98682 (pMQ115). These strains have QM9414 as the host strain. VTT-D-99702 (pMQ113) has Rut-C30 as the host strain.

Example 4

Cultivation of the EGI-HFBI and EGIcore-HFBI Protein Producing and HFBI Over-Producing *Trichoderma* Strains EGI-HFBI and EGIcore-HFBI fusions were produced under the cbh1 promoter in a 15-liter fermenter using *T. reesei* strains VTT-D-98693 (pMQ103) and VTT-D-98691 (pMQ113), respectively. Strains were grown 5 days on minimal medium (Penttilä et al., 1987) containing 4% Solka flock cellulose (James River Corporation, Berlin, N.H.) and 2% spent grain (Primalco, Koskenkorva, Finland). EGIcore-HFBI was also produced in fermenter (15 l) using the Rut-C30 strain VTT-D-99702 (pMQ113) with 4% lactose medium. To induce the production of EGI-HFBI and EGI-core-HFBI fusions under *Aspergillus* gpdA promoter, *T. reesei* strains VTT-D-98681 (pMQ105) and VTT-D-98682 (pMQ115) were cultivated in 15-liter fermenter. Strains were grown 3 to 5 days on minimal medium supplemented with 2% glucose, 0.2% Peptone, and 0.1% Yeast Extract, and with glucose feed to maintain the glucose concentration in the range of 1 to 3% throughout the cultivation. HFBI over-producing strain VTT-D-98692 (pEA10) was grown similarly in 15l on glucose medium and the strain VTT-D-98492 (pQM121) over-producing HFBI under cbh1 promoter was cultivated for 7 days in 15-liter fermentor on medium containing 4% Solka flock and 2% spent grain. The control cultivations with the host strains of the transformants, QM9414 (VTT-D-74075) and Rut-C30 (VTT-D-86271), were carried out on media containing i) Solka flock cellulose and either spent grain or whey, ii) lactose and iii) glucose similarly as described above.

When proper some *T. reesei* transformant strains and their host strains were also cultivated at 28° C. in shake flasks for 5 to 6 days in 50 to 150 ml volume of *Trichoderma* minimal medium (Penttilä et al., 1987) supplemented with either 3% Solka flock cellulose and 1% spent grain or 34% glucose with glucose feeding.

Example 5

Standard Separation Assays and Analysis

If not otherwise stated the standard AIPS and subsequent analyses and calculations were carried out as explained in this example.

In general whole fermentation broth, supernatant (biomass separated by centrifugation or filtration) or purified proteins in buffer were separated in 10 ml graduated tubes. First detergent was added into the tubes and the tubes were then filled to 10 ml with protein containing liquid. The amount of detergent in the tube was calculated in weight percent of detergents. After thorough mixing in an overhead shaker the separation took place by either gravity settling in a water bath at constant temperature or by centrifugation at constant temperature. The separation usually was performed at 30° C., the standard amount of detergent used was 2-5% (w/v). After separation the volume ratio was noted and samples were taken from the lighter and heavier phase for analysis.

Two-phase separations were analysed qualitatively by using SDS-PAGE gels followed by visualization of the fusion proteins with Coomassie brilliant blue R-250 (Sigma) or Western blotting. Polyclonal anti-HFBI antibody were used in Western analysis for detection of EGIcore-HFBI EGI-HFBI and dCBD-HFBI proteins together with alkaline phosphatase conjugated anti-rabbit IgG (Bio-Rad). Alkaline phosphatase activity was detected colorimetrically with BCIP (5-bromo-4-chloro-3-indolyl-phosphate) used in conjunction with NBT (nitro blue tetrazolium) (Promega).

Contaminating endogenous EGI, CBHI and EGIII in the top phase was tested with appropriate antibodies. Acidic protease activity in the top and bottom phase was also tested using the SAP method (Food Chemicals Codex, p. 496-497, 1981), which is based on the 30 min enzymatic hydrolysis of a hemoglobin substrate. All reactions were performed at pH 4.7 and 40° C. Unhydrolyzed substrate was precipitated with 14% TCA and removed by filtration. The released tyrosine and tryptophan was determined spectrophotometrically. Total protein concentrations were determined by Non-Interfering Protein Assay™ (Geno Technology, Inc).

EGI activity was detected using 4-methylumbelliferyl-β-D-cellobioside (MUC) (Sigma M 6018) as substrate (Van Tilbeurgh H. & Caeyssens M., 1985; Van Tilbeurgh et al., 1982). EGI hydrolyses the 3-glycosidic bond and fluorogenic 4-methylumbelliferone is released, which can be measured using a fluorometer equipped with a 360 excitation filter and a 455 nm emission filter. CBIE also hydrolyses the substrate and it was inhibited by addition of cellobiose (C-7252, Sigma). EGI containing liquid was added in an appropriate dilution to a buffer containing 50 mM sodium acetate buffer (pH 5), 0.6 mM MUC and 4.6 mM cellobiose. The mixture was heated to 50° C. The reaction was stopped after ten minutes using 2% $Na_2CO_3$, pH 10. Purified CBHI was detected using the same assay as for EGI without the addition of the inhibitor cellobiose.

The partition coefficient K was defined as the ratio of the measured concentrations or activities in the top and bottom phase, respectively.

The Yield Y was defined as follows:

$$Y_T = \frac{1}{1 + \left[\frac{V_B}{V_T} \cdot \frac{1}{K}\right]}$$

where $Y_T$ is the Yield of the top phase, $V_B$ and $V_T$ are the volumes of bottom and top phase, respectively. The Yield of the bottom phase can be described accordingly.

The mass balances, e.g. recovery of all added protein, were always checked for completeness to ensure no artificially high Yield (e.g. due to possible inactivation of the protein in the bottom phase). The values were usually calculated based on total enzyme activity (EGI wt plus the EGI-fusion) and thus the values are underestimated for the separation of the fusion as demonstrated in Example 16.

Example 6

Small Scale ATPS Separation Studies and Gel Analysis

EGI-HFBI and EGIcore-HFBI fusions produced under the cbh1 promoter in a 15-liter fermenter on Solka flock cellulose and spent grain medium as described in Example 4 using *T. reesei* strains VTT-D-98693 (pMQ103) and VTT-D-98691 (pMQ113), respectively, were separated in small scale ATPS as described above.

Figure 8:
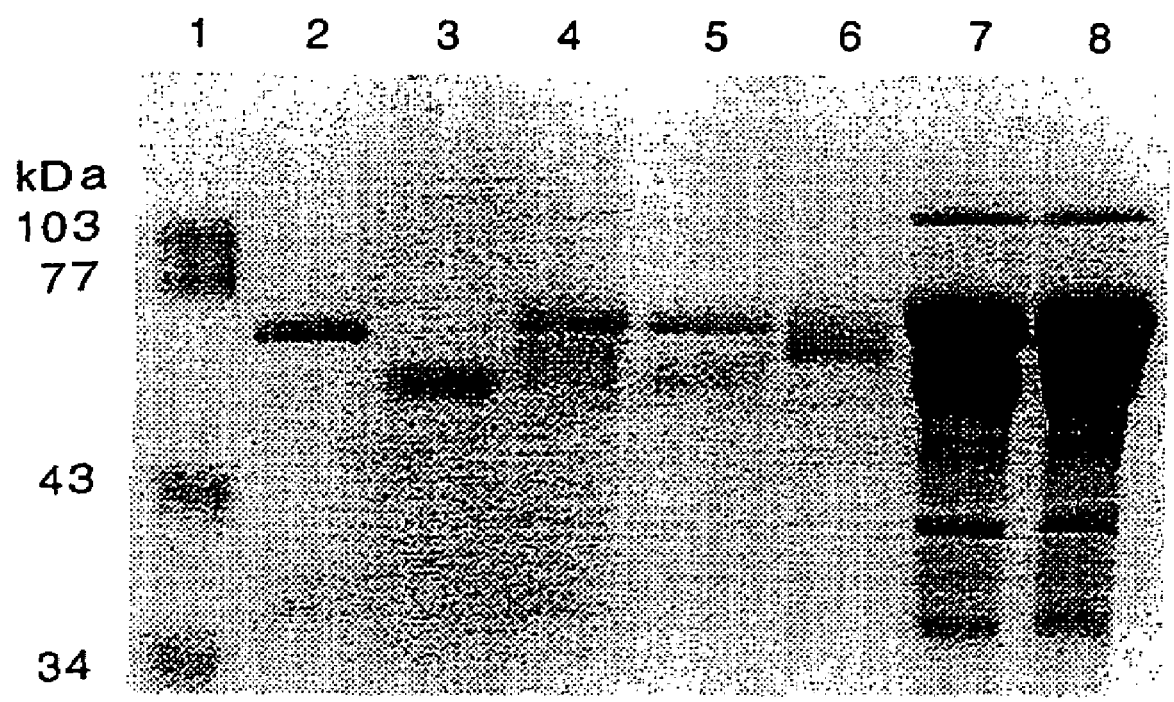
FIG. 8 Coomassie-stained 10% sodium dodecyl sulphate polyacrylamide gel electrophoresis (SDS-PAGE) of the partitioning of EGIcore-HFBI fusion protein in two-phase separation using 5% of the detergent C12-C18EO5. Lane 1, Molecular weight marker; Lane 2, Purified CBHI (4 µg); Lane 3, Purified EGI (4 µg); Lane 4, 1/10 diluted VTT-D-98691 cellulose-based culture filtrate; Lanes 5 and 6, 1/10 diluted bottom phase and detergent phase (top phase), respectively, after separation of VTT-D-98691 culture filtrate with 5% detergent; Lane 7, Non-diluted bottom phase; Lane 8, Non-diluted VTT-D-98691 cellulose culture filtrate.

The phases from the two phase separations were analysed qualitatively by using SDS-PAGE gels followed by visualization of the fusion proteins with Coomassie brilliant blue or Western blotting. Coomassie stained SDS-PAGE (10%) is shown in FIG. 8. In the lane containing the non-extracted culture filtrate three distinct closely migrating bands can be seen (the sample was diluted 1/10 with $H_2O$). The topmost band is CBHI, the band in the middle is EGIcore-HFBI fusion and the lower one endogenous EGI. In the samples separated in ATPS, only two bands (CBHI and EGI) are seen in the sample from bottom phase and one band representing EGIcore-HFBI in the sample obtained from the top phase.

Figure 9:
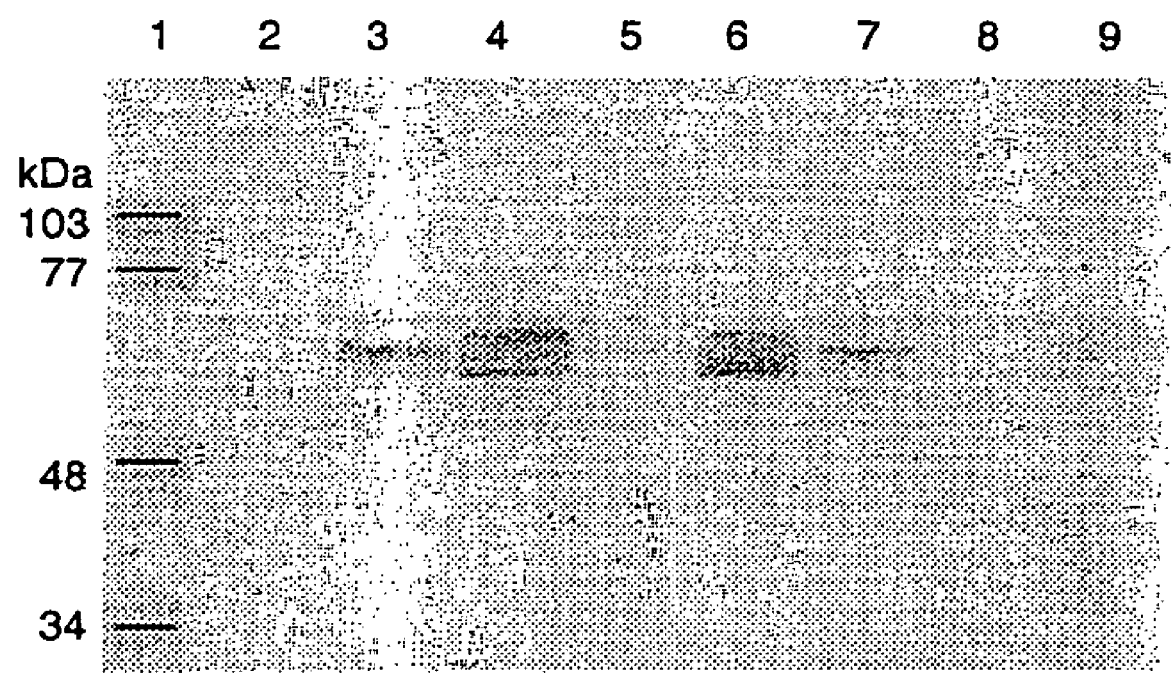
FIG. 9 Western analysis of the partitioning of EGIcore-HFBI fusion protein in two-phase separation by using different concentrations of the detergent C12-C18EO5. Fusion proteins were detected with anti-HFBI antibodies. Lane 1, Molecular weight marker; Lane 2, Purified EGI; Lane 3, VTT-D-98691 cellulose culture filtrate; Lanes 4 and 5, Detergent phase (top phase) and bottom phase, respectively, after separation of VTT-D-98691 culture filtrate with 5% detergent; Lane 6, Same as lane 3, except 2% detergent was used; Lane 7, Same as lane 4, except 2% detergent was used; Lane 8, Purified EGI; Lane 9: Purified CBHI.

Western blotting with HFBI antibody showed thick bands for the top phase, whereas for the bottom phase there was only faint band demonstrating that the fusion is separating strongly into the detergent top phase. FIG. 9 shows the separation of the EGIcore-HFBI fusion produced on cellulose media into the top phase. Contaminating endogenous EGI and EGIII in the top phase was tested with appropriate antibodies but no signal was detected.

Figure 10:
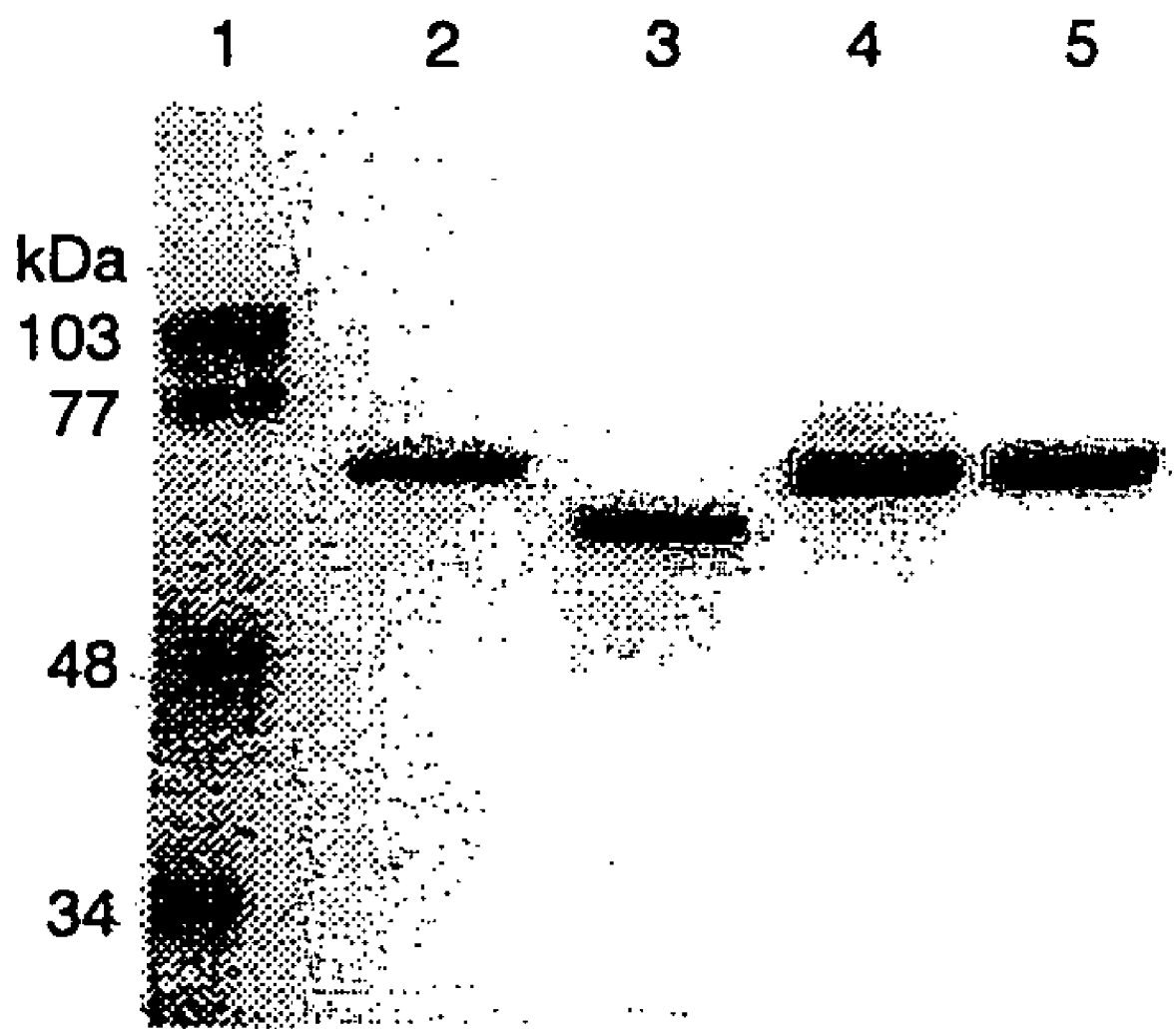
FIG. 10 Coomassie-stained 10% SDS-PAGE showing further purification of EGIcore-HFBI fusion protein from the endogenous CBHI when the top phase was re-extracted with 2% detergent. Lane 1, Molecular weight marker; Lane 2, Purified CBHI (4 µg); Lane 3, Purified EGI (4 µg); Lane 4, Detergent phase (top phase) after first extraction; Lane 5, Detergent phase (top phase) after second extraction.

Small amount of endogenous CBHI was found in the upper phase when CBHI antibody was used in Western blotting. EGI, EGIII and proteases were not found in the top phase. Further purification from the contaminating CBHI was observed when the top phase was re-extracted with 2% detergent. The FIG. 10 shows that the upper phase does not anymore contain CBHI and pure fusion protein is recovered.

EGIcore-HFBI was also produced in fermenter (15 l) using the Rut-C30 strain VTT-D-99702 (pMQ113) with 4% lactose medium. The separation in ATPS carried out in the standard manner gave essentially the same result as the separation from cellulose containing medium thus demonstrating that the purification can be carried out from several media relevant for large scale industrial use.

Acidic protease activity in the top was only 1/15 compared to the bottom phase (table below) demonstrating that acidic proteases remain in the bottom phase.

|  | A (275 nm) | HUT[3]/ml |
|---|---|---|
| Bottom phase[1] | 0.146 | 41.6 |
| Top phase[2] | 0.009 | 2.6 |

[1] 1/10 diluted bottom phase after separation of VTT-D-98691 culture filtrate with 2% detergent
[2] 1/100 diluted bottom phase after separation of VTT-D-98691 culture filtrate with 2% detergent
[3] 1 HUT = enzyme concentration, which in reaction conditions hydrolyses hemoglobin in 1 min so that the absorbance at 275 nm of the formed hydrolysate equals 1.10 µg tyrosine/ml 0.006 N HCl solution.

These results show that the fusion protein can be purified extremely efficiently and the resulting preparate is free of other proteins produced by the fungus including proteases.

Example 7

Recovery of the Native EGI in ATPS after Thrombin Cleavage

EGI-HFBI protein produced by the strain VTT-D-98693 has a thrombin cleavage site (LVPRGS) designed in the linker region between the EGI CBD and HFBI, which would enable the recovery of the native EGI after thrombin cleavage. EGI-HFBI fusion protein was purified from the culture filtrate (100 ml) of strain VTT-D-98693 grown on 4% Solka flock cellulose and 2% spent grain as described in Example 4 using the 2-phase separation system (5% detergent). After removal of the bottom phase the detergent phase was extracted by isobutanol. The resulting water phase (~19 ml) was divided in eppendorf tubes and the liquid was evaporated with speed vac. Remaining lyophilizate was diluted to 50 mM Tris-Cl (pH 8). To test the efficiency of thrombin cleavage, 9 units of thrombin (Sigma) was incubated >24 h with 1 mg EGI-BBI fusion protein in 36° C. at pH 8.0. Coomassie stained SDS-PAGE (10%) was used for detection.

Figure 11:
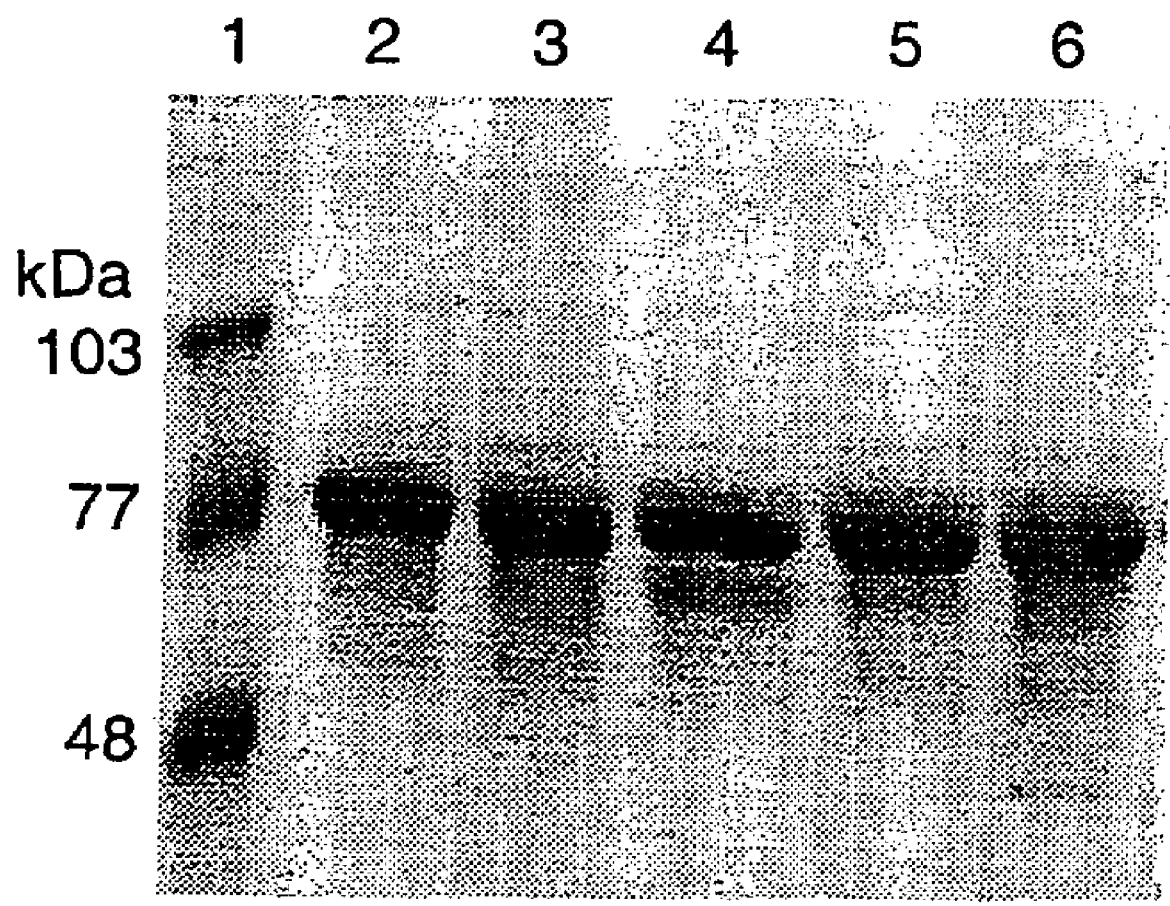
FIG. 11 Coomassie-stained 10% SDS-PAGE analysis of the EGI-HFBI protein when treated with thrombin. Lane 1, Molecular weight marker; Lane 2, EGI-HFBI (1 mg/ml) treated 72 h with 3 U of thrombin at 24° C.; Lane 3, Same as lane 2, except no thrombin was added; Lane 4, EGI-HFBI (1 mg/ml) treated 48 h with 9 U of thrombin at 36° C.; Lane 5, Same as lane 4, except no thrombin was added; Lane 6, Same as lane 5, except no incubation at 36° C.

Only minor cleavage was observed in 48 h under these conditions (FIG. 11), possibly due to steric hindrance by O-glycosylation in the linker.

Example 8

Separation of Low Concentrations of EGIcore-HFBI in ATPS

Detergent based aqueous two-phase systems were successfully applied using very low concentrations (diluted) of EGIcore-HFBI fusion protein produced with the cbh1 promoter in *T. reesei* VTT-D-98691 (pMQ113) from a 15 liter cultivation carried out on Solka flock cellulose with spent grain as described in Example 4.

The original protein concentration of the supernatant was 7.0 mg/ml. This supernatant was diluted with de-ionised water by a factor of 100 and 1000, respectively. The fusion protein could be separated using 2% (w/w) of the detergent C12-C18EO5 with partitioning coefficients higher than 5. This is shown in the table below together with the experiment with non-diluted supernatant. The partitioning coefficients were calculated based on activity measurements for total EGI (wild type and fusion protein together).

|  | EGIcore-HFBI non-diluted supernatant | dilution 1/100 | dilution 1/1000 |
|---|---|---|---|
| K | 4.1 | 5.3 | 5.6 |
| Y [%] | 38 | 31 | 32 |

Example 9

Separation of EGIcore-HFBI from Fungal Biomass Containing Culture Broths

EGIcore-HFBI from *T. reesei* strain VTT-D-98691 (pMQ 113-2) was cultivated (50 ml in 250 ml shake flasks) on Solka flock cellulose with spent grain as described in Example 4. Directly after the cultivation, part of the whole broth was centrifuged at 3000 rpm for 30 min, supernatant was spilled out and the centrifuged mycelium was added to the supernatant to obtain artificial whole broths containing different amounts of biomass.

Using 5% of C12-C18EO5 in a 10 g experiment consisting of up to 50% wet biomass (weight of wet biomass divided by the sum of wet biomass and supernatant) could still be separated without any difficulties. The Yield remained in between 61 and 64% and therefore it is not significantly different in comparison to the experiment carried out with supernatant only (without mycelium) (see table below). The total recovery of the fusion protein is even higher. This is most probably due to cell attached enzyme extracted in the ATPS increasing the total amount of EGI. The partitioning coefficient was calculated based on activity measurements for total EGI (wild type and fusion protein together).

|  | K | Y [%] |
|---|---|---|
| Supernatant | 5.5 | 62 |
| 25% of wet biomass in supernatant | 7.3 | 66 |
| 40% of wet biomass in supernatant | 6.4 | 61 |
| 50% of wet biomass in supernatant | 7.6 | 64 |

Example 10

Separation of EGI-HFBI in ATPS

EGI-HFBI from *Trichoderma reesei* strain VTT-D-98693 (pMQ 103) from a 15 liter cultivation carried out on Solka flock cellulose and spent grain as described in Example 4 was separated in a 10 g experiment using different amounts of C12-C18EO5. The partitioning coefficients are shown below. The partitioning coefficient was calculated based on activity measurements for total EGI (wild type and fusion protein together), and as in previous examples the endogenous EGI is included in the partitioning coefficients.

|   | Detergent [% w/w] | | | |
|---|---|---|---|---|
|   | 2 | 3 | 5 | 7 |
| K | 1.9 | 1.8 | 1.4 | 1.1 |

Example 11

Separation of EGIcore-HFBI in 50 ml

EGIcore-HFBI from *T. reesei* strain VTT-D-98691 (pMQ 113) cultivated in 15 liters using Solka flock cellulose and spent grain as described in Example 4 was separated in Falcon tubes in a 50 g experiment using 5% of C12-C18EO5. A partition coefficient of 2.52 and a yield of 51% could be obtained. The separation was performed at 30° C. at 3000 rpm for 30 minutes. The values are based on activity measurements for total EGI activity (wild type and fusion protein together) including endogenous EGI.

Example 12

Separation of EGIcore-HFBI in ATPS Using Different Detergents

EGIcore HFBI from *T. reesei* strain VTT-D-98691 (pMQ 113) cultivated in 15 liters using Solka flock cellulose with spent grain as described in Example 4 was separated in a 10 g experiment using 2% of detergent in each experiment. The detergents investigated in this example were C10 EO5, C12 EO5, C14 EO6 (each Nikko Chemicals, Japan), C12-C18 EO5 ("Agrimul NRE 1205", Henkel, Germany), C12/14 5EO, C12/14 6EO (Clariant, Germany), C9/11 EO5.5 ("Berrol 266", Akzo Nobel, Germany), Triton X-114 (Sigma, Germany). The partition coefficients and yields are listed below. The values are based on activity measurements for total EGI activity (wild type and fusion protein together) including endogenous EGI.

|   | K | Y (fusion) [%] |
|---|---|---|
| C10EO5 | 20 | 56 |
| C12EO5 | 15 | 57 |
| C12-C18EO5 | 14 | 66 |
| C12/14 5EO | 12 | 58 |
| C12/14 6EO | 14 | 62 |
| C14EO6 | 11 | 54 |
| C9/11 EO5.5 | 5 | 30 |
| Triton X-114 | 0.16 | 53 |

Example 13

Separation of EGIcore-HFBI in ATPS from Glucose Grown Cultures

EGIcore-HFBI was separated from cultivation of the *Trichoderma reesei* strain VTT-D-98682 (pMQ115) cultivated with glucose as described in Example 4. The supernatant was separated with 2% of the detergent C12-C18 EO5. The fusion protein could be partitioned with a K value of 2.4. In comparison, the K value for the native EGI is 0.3 when measured in a similar way for purified EGI.

Example 14

Separation of EGIcore-HFBI Using Different Concentrations of Detergent

EGIcore-HFBI from *T. reesei* VTT-D-98691 (pMQ 113) cultivated in 15 liters using Solka flock with spent grain as described in Example 4 was separated in detergent based ATPS applying different amounts of the detergent C12-C18 EO5 on the cell free supernatant. The partitioning coefficients are shown in the table below. The corresponding gel electrophoresis and Western antibody-blots are shown in FIG. 8 and FIG. 9, respectively.

The values are based on activity measurements of total EGI activity.

| Amount of detergent C12-C18 EO5 | K | Yield (%) |
|---|---|---|
| 1.0% | 6.1 | 9 |
| 2.0% | 4.1 | 38 |
| 3.5% | 3.6 | 50 |
| 5.0% | 2.9 | 55 |
| 7.5% | 1.7 | 53 |
| 10.0% | 1.1 | 58 |

Example 15

Re-Extraction of the Detergent Phase

Detergent based ATPS was applied on EGIcore-HFBI fusion protein containing supernatant produced by the strain VTT-D-98691 (pMQ 113) in a shake flask cultivation. The first extraction using C12-C18EO5 conducted under the standard conditions shows a partitioning coefficient of 16 and a yield of 72% (wild type EGI measured together with fusion protein). The top phase was re-extracted in 10 mM sodium acetate buffer (pH 5) with 2% of detergent. A partitioning coefficient of 52 and a yield of 89% could be obtained. In the re-extraction experiment of the bottom phase (2% of detergent), a small yield of 7.5% and a K of 0.8 of EGI activity were achieved. The partitioning coefficients were calculated based on activity measurements for total EGI (wild type and fusion protein together). Due to the wild type EGI present in the sample, the yield is at least 72% and the partitioning coefficient at least 16 in the first extraction. The SDS-PAGE results of both extractions are shown in FIG. 10.

| Separation step | K | Y [%] |
|---|---|---|
| 2% detergent | 16 | 72 |
| reextraction top phase | 52 | 89 |
| reextraction bottom phase | 0.8 | 7.5 |

Example 16

Separation of Pure Cellulases in ATPS

The effect of HFBI on partitioning and the final yield can further be demonstrated by comparing the extraction result of EGIcore-HFBI fusion with extraction results obtained with purified wild type EGI and EGIcore. The fusion protein is partitioning more than 100 times better to the detergent phase (see table below).

The improvement on the partitioning of the purified fusion protein from the first extraction obtained in the re-extraction (see Example 15) can be explained by the partitioning of the wild type EGI as demonstrated with purified wild type EGI in the table below. The wild type EGI lowers the partitioning coefficient in the first extraction (since EGI activity is measured from both top and bottom phase), but the absence of it in the retraction increases the partitioning coefficient of the EGIcore-HFBI fusion. The purity can in addition be demonstrated by analysing the partitioning of pure CBHI, which is the major contaminating protein corresponding to about 50% of all secreted *T. reesei* proteins. Pure CBHI has a partitioning coefficient of 0.5 and a yield of 3.6 and is therefore separated from the fusion protein.

| Separation step | K | Y [%] |
|---|---|---|
| re-extraction of top phase | 52 | 89 |
| extraction of pure wild type EGI | 0.3 | 2.2 |
| extraction of pure EGI-core | 0.3 | 2.3 |
| extraction of pure CBHI | 0.5 | 3.6 |

Using the definitions of K and Y and calculating mass balances, the ratio of the amount of EGI fusion protein to EGI wild type can be calculated. The "true" partition coefficients and Yields can be concluded from this. "True" means the values which would be detected if it would be possible to measure only the amount of EGI-fusion without measuring the amount for EGI wild type at the same time.

The fundament for the calculation is the re-extraction experiment. The re-extracted top phase is believed to be pure. An example of the measured values and the calculated "true" values based on this are shown in the table below for two cultivations of VTT-D-98691 (pMQ113) grown as described in Example 4.

| cultivation vessel | cultivation substrate | K "with EG1 wt" | Y [%] "with EG1 wt" |
|---|---|---|---|
| 15 liter fermenter | whey permeate | 4 | 16 |
| 250 ml shake flask | cellulose | 16 | 66 |

Example 17

HFBI and HFBII Purification in ATPS

HFBI was produced by cultivating the *T. reesei* strain VTT-D-98692 (pEA10-103B) using glucose as substrate as described in Example 4. HFBI could be separated using 2% of the detergent C12-C18 EO5 with a partition coefficient higher than 20 under the standard conditions described.

HFBII was produced by cultivating the *T. reesei* strain VTT-D-74075 (QM9414) on whey spent grain as described in Example 4. HFBII could be separated using 2% of the detergent C12-C18 EO5, exceeding a partition coefficient of 10 under the standard conditions.

Both HFBI and HFBII hydrophobins are thus partitioning well to the upper phase in ATPS.

Example 18

Detergent Based ATPS with Additional NaCl

EGIcore-HFBI from which cultivation of *T. reesei* was separated in a 10 g experiment using 5% of C12-C18EO5. The partitioning coefficient of the supernatant was 3.5 with a volume ratio of 0.2. Using 1.1% (w/v) NaCl the partitioning coefficient could be increased to 4.3 with a lower volume ratio of 0.14.

Example 19

Construction of an *E. coli* Strain Expressing a Fusion Protein HFBI-dCBD, Containing Hydrophobin I and Double Cellulose Binding (CBD) Domains A 280 bp DNA fragment containing a modified cbh2 linker region followed by the coding region of hfb1 from Ser-23 to the STOP codon was amplified by PCR using the plasmid pARO1 (Nakari-Setälä et al., 1996) as a template. The 5' primer was 5' TCT AGC AAGCTT GGC TCT AGT TCT GGA ACC GCA CCA GGC GGC AGC AAC GGC AAC GGC AAT GTT TGC (SEQ ID NO: 14) and the 3' primer was 5' TCG TAC AAGCTT TCAAGC ACC GAC GGC GGT (SEQ ID NO: 15). The sequences in bold in the 5' and 3' primers encode the modified CBHII linker (Gly Ser Ser Ser Gly Thr Ala Pro Gly Gly) (SEQ ID NO: 39) and a translational STOP, respectively, and the underlined AAGCTT in both primers is a HindIII site. The PCR fragment was purified from agarose gel, digested with HindIII and ligated to HindIII digested and SAP treated (Shrimp Alkaline Phosphatase, USB) pSP73 resulting in plasmid pTNS9.

Figure 12:
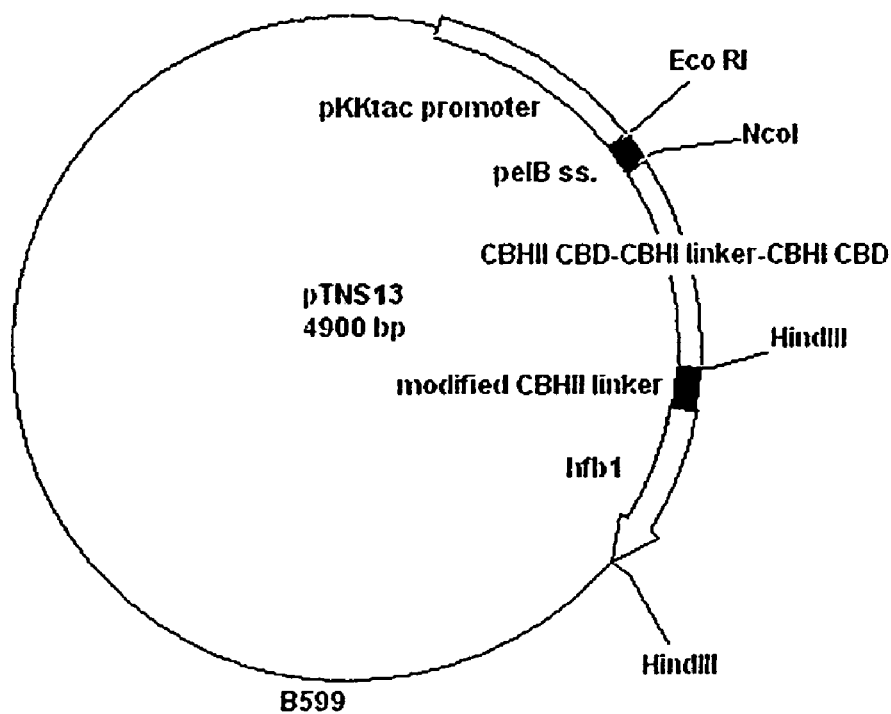
FIG. 12 shows the map of the plasmid pTNS13.

For subsequent cloning of the modified CBHII linker-HFBI fragment to an *E. coli* expression vector, pTNS9 was digested with HindIII and the proper fragment was purified from agarose gel. This HindIII fragment was cloned to HindIII digested and SAP treated (Shrimp Alkaline Phosphatase, USB) B599 resulting in pTNS13 (FIG. 12). The *E. coli* expression vector B599 is essentially the same as the one described by Linder et al. (1996) except that it is missing a STOP codon at the end of the protein coding sequence. It carries the coding sequence for a fusion protein containing CBHII CBD (41 N-terminal residues of CBHII) and CBHI CBD linked together via CBHI linker region (CBHI linker and CBD are the last 57 residues in CBHI). The expression and secretion of the fusion protein in B599 is under the control of tac promoter and pelB signal sequence (Takkinen et al., (1991). pTNS13 expression vector thus carries the coding region for a fusion protein of double CBD and HFBI linked in frame via the Gly-Ser-Ser-Ser-Gly-Thr-Ala-Pro-Gly-Gly (SEQ ID NO: 39) peptide. This vector also contains the amp gene for selection of *E. coli* transformants. pTNS13 plasmid was transformed into *E. coli* strain RV308 (su-, ΔlacX74, galISII::OP308, strA) and this strain was used for production of the fusion protein.

Example 20

Separation of HFBI-dCDB Molecules Expressed in *E. coli* in ATPS dCBD-HFBI was produced in *E. coli* strain RV 308 transformed with pTNS13 plasmid as described above. The inoculum of RV308/pTNS13 was grown to the exponential growth phase in LB medium containing ampicillin (0.1 g/l) and 1% glucose. Fermentation was carried out using mineral salt medium described by Pack et al. (1993) with glucose (feed) in 10 liter fermenter. During cultivation temperature was maintained at 28° C. and pH was controlled at 6.8 with $NH_4OH$. Cell growth was monitored by measuring $OD_{600}$ and dry weight of biomass. The culture was induced with 50 µM (final concentration) IPTG (isopropyl-β-D-thiogalacto-pyranoside) at late-exponential growth phase ($OD_{600}$=50-60) to promote fusion protein production.

Figure 13:
FIG. 13 Western analysis of the partitioning of dCBD-HFBI fusion protein in two-phase separation using 5% of the detergent C12-C18EO5. Fusion protein was detected with anti-HFBI antibody. Lane 1, Four times concentrated culture filtrate; Lane 2, Four times concentrated bottom phase; Lane 3, Top phase.

Two-phase separation analysis of dCBD-HFBI protein was performed using culture filtrate and 5% detergent in the total volume of 40 ml. Results from Western blotting showed that 2-phase separation with 5% detergent in the standard way was highly specific also for the dCBD-HFBI fusion. Strong signal was observed in the sample from the detergent phase compared to the sample from the bottom phase as shown in FIG. 13.

Example 21

Figure 14:
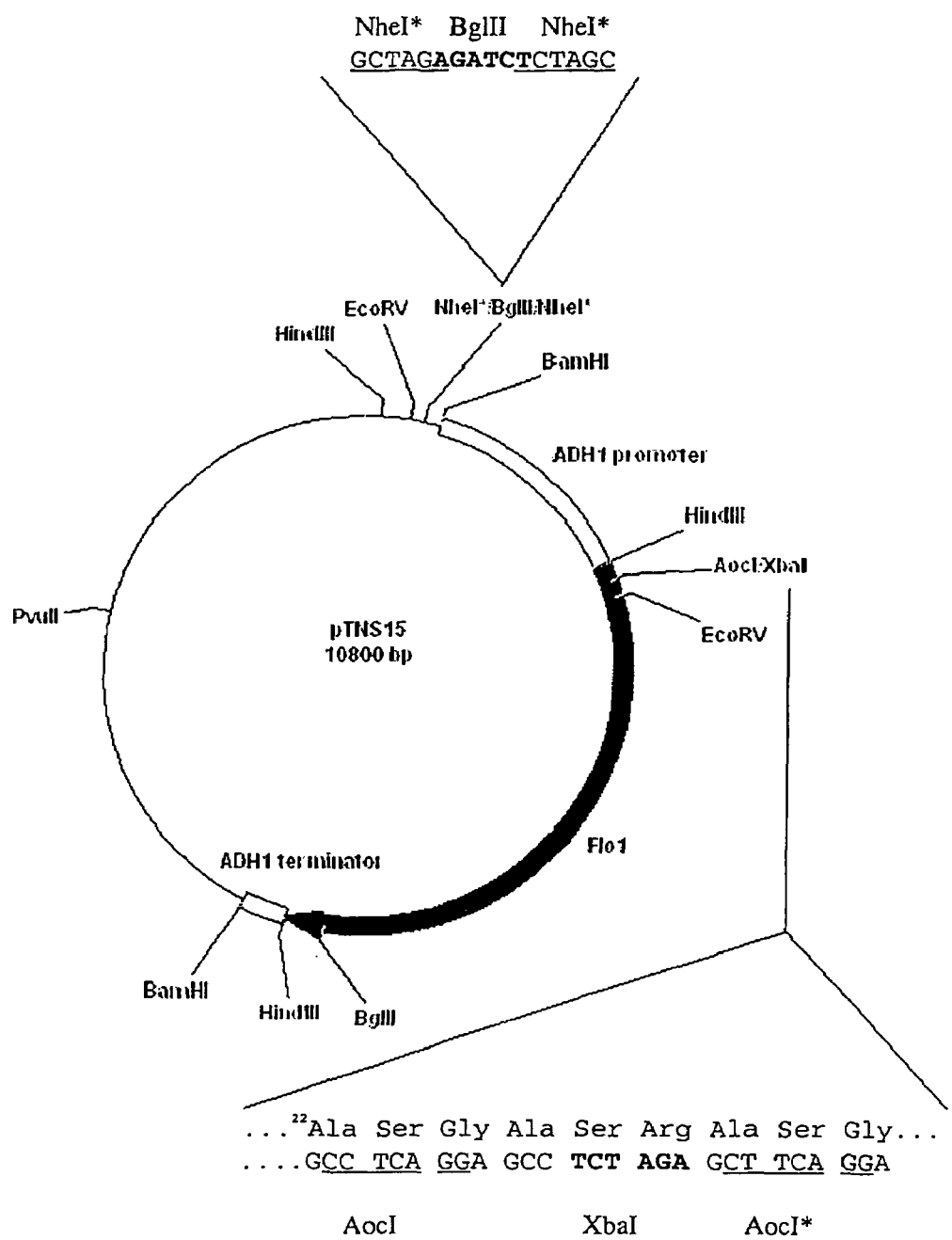
FIG. 14 shows the map of the plasmid pTNS15. A non-functional restriction site is indicated with an asterisk (SEQ ID NO: 43). The AocIXbaI sequences are SEQ ID NOS:44 and 45).
Figure 15:
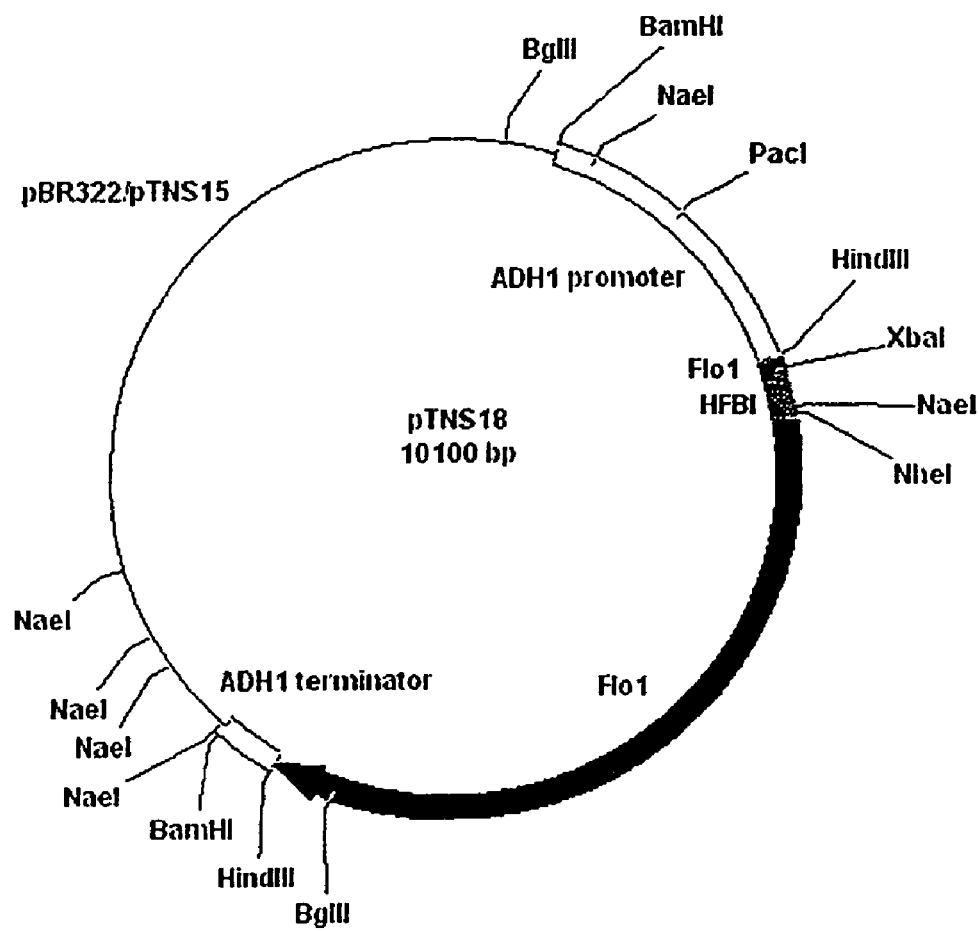
FIG. 15 shows the map of the plasmid pTNS18.

Construction of Yeast Strains Expressing HFBI-Flol Fusion Protein on the Cell Surface For construction of a HFBI-FLO1 fusion protein expression cassette, hfb1 (SEQ ID NO:1) coding region (from Ser-23 to the STOP codon) was amplified with PCR using pARO1 (Nakari-Setälä et al., 1996) as a template and as a 5' primer TCT AGC TCTAGA AGC AAC GGC AAC GGC AAT GTT (SEQ ID NO:16) and as a 3' primer TGC TAG TCG ACC TGC TAGCAG CAC CGA CGG CGG TCT G (SEQ ID NO: 17). The underlined sequences in the 5' and 3' primers are XbaI and NheI sites, respectively. The 0.225 bp PCR fragment was purified from agarose gel and ligated to pGEM-T vector (Promega) resulting in pTNS10. The hfb1 fragment was released from pTNS10 with XbaI and NheI and ligated to pTNS15 cut with the same restriction enzymes. Plasmid pTNS15 (FIG. 14) is essentially the same as plasmid pBR-ADH1-FLO1L by Watari et al. 1994 except that a NheI site in the pBR322 backbone has been replaced by a BglII site and a unique XbaI site is introduced by linker cloning in the unique AocI site preceding the putative signal sequence cleavage site. The resulting plasmid pTNS18 (FIG. 15) contains the complete expression cassette for BFBI-FLO1 fusion protein in which HFBI substitutes the putative lectin domain from Ser-26 to Ser-319 in the yeast flocculin FLO1 (SEQ ID NO:18).

Figure 16:
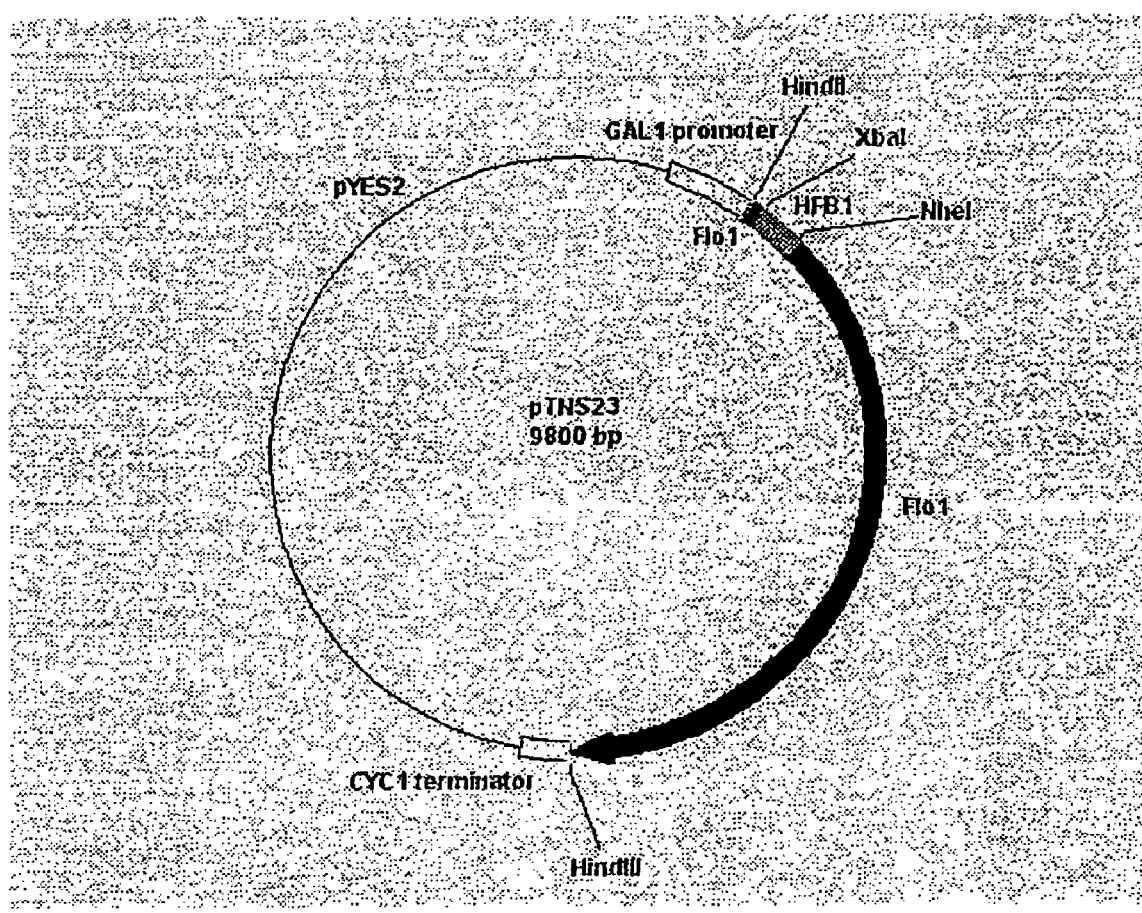
FIG. 16 shows the map of the plasmid pTNS23.

In the next step, yeast expression vector for production of HFBI-FLO1 fusion protein was constructed. The expression vector used as a backbone in the construct is pYES2 (Invitrogen) (SEQ ID NO:19) which is a high-copy episomal vector designed for inducible expression of recombinant proteins in *S. cerevisiae*. It carries GAL1 promoter and CYC1 terminator sequences which regulate transcription, and 211 origin of replication and URA3 gene for maintenance and selection in the host strain. The plasmid pTNS18 was digested with HindIII and the released 3.95 kb fragment containing the expression cassette for HFBI-FLO1 was purified from agarose gel and ligated to pYES2 digested with HindIII. This ligation mixture was concentrated by standard ethanol precipitation. The ligation mixture should contain besides unligated fragments and uncorrect ligation products also molecules where the vector and insert are correctly ligated with each other to result in plasmid pTNS23 (FIG. 16) which carries the expression cassette for HFBI-FLO1 operably linked to GAL1 and CYC1 terminator sequences.

The above ligation mixture was transformed using the LiAc method of Gietz et al. (1992) into a laboratory *S. cerevisiae* strain H452 (wild type W303-1A; Thomas and Rothstein, 1989). Transformant colonies able to grow on SC-URA plates were picked and streaked on selective plates. Nitrocellulose replicas were taken from the plates and treated for colony hybridization according to Sherman et al. (1983). To find those yeast colonies containing the pTNS23 plasmid, replicas were hybridized with digoxigenin labelled hfb1 coding fragment after which an immunological detection was performed all according to the manufacturer (Boehringer Mannheim). Plasmids were recovered from several yeast colonies giving positive hybridization signal by isolating total DNA and using this in electroporation of *E. coli*. Restriction mapping and sequencing were carried out to confirm that the pTNS23 plasmid in the yeast transformants was correct. One of the transformants carrying plasmid pTNS23 was chosen for further studies and was designated VTT-C-99315. The control strain for it is yeast strain H2155 which carries the plasmid pYES2 in H452 background.

Example 22

Separation of Yeast Cells Expressing HFBI-Flo1 Fusion Protein in ATPS

Figure 17:
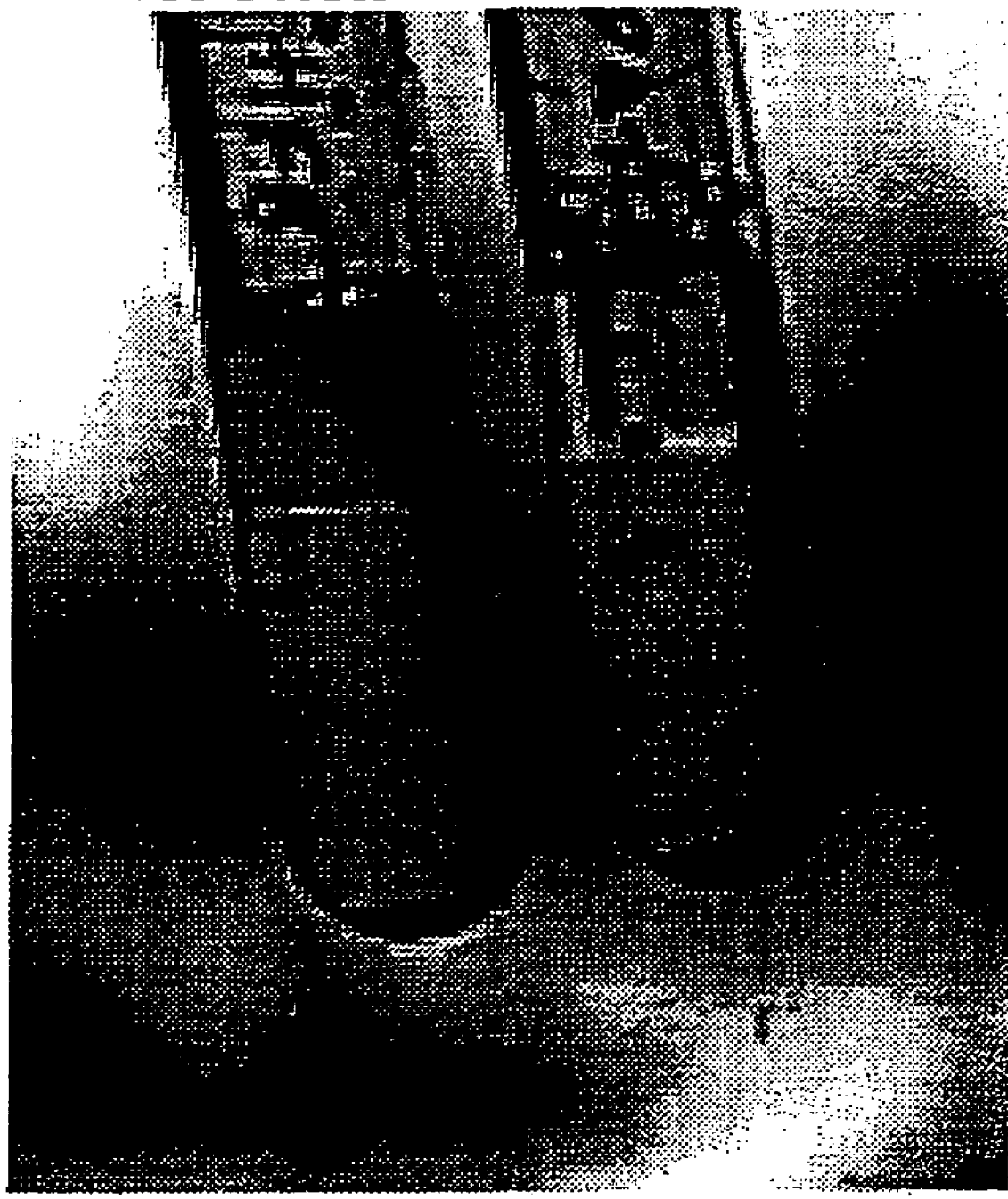
FIG. 17 shows that separation to the detergent phase of cells expressing a hydrophobin on cell surface occurs: the top detergent phase of S. cerevisiae VTT-C-99315 is turbid, whereas the top detergent phase of the control strain H2155 is clear.

The *Saccharomyces cerevisiae* strain VTT-C-99315 (vector pTNS23) and its control strain H2155 (vector pYES2) were cultivated on synthetic complete medium lacking uracil (SC-URA) (Sherman, 1991) with 2% galactose as the carbon source to give an $A_{600}$ of approximately 4. Approximately $6.3 \times 10^8$ cells in their culture medium were taken to ATPS using 7% (w/v) C12-18EO5 detergent (Agrimul NRE from Henkel) in a total volume of 5 ml. ATPS was carried out using standard protocol. After phase separation by gravity setting, the top detergent phase was clearly turbid in the case of the strain VTT-C-99315 in contrast to the control strain whose detergent phase was clear (FIG. 17). Samples were taken from the top phases and dilution series from $10^{-1}$ to $10^{-5}$ were prepared in 0.9% NaCl and plated on YPD plates. After incubation at 30° C. the amount of yeast colonies were calculated showing at least 70 times more yeast colonies of the strain VTT-C-99318 on YPD plates compared to the control strain. This clearly manifests that also in a system over-loaded with cells, separation to the detergent phase of cells expressing a hydrophobin on cell surface occurs.

Example 23

Partitioning of EGIcore-HFBI Fusion Protein in Hydrophobin-Containing and Non-Containing Pure Systems The effect of free HFBI and HFBII hydrophobins on the partitioning of EGIcore-HFBI was investigated by comparing how efficiently a sample of purified EGIcore-BFBI in 50 mM acetate buffer pH 5.0 was extracted to the detergent phase in the presence and absence of purified HFBI and HFBII. The extraction was followed by measuring the depletion of hydrolytic activity on a soluble substrate such as methylumbelliferyl cellobioside in the aqueous phase before and after extraction. When 0.7 g/l of either purified hydrophobin was present in the separation of 0.02 g/l of EGIcore-HFBI with 2% C12-18EO5 at 30° C. the extraction was affected in the following way: 93% of the protein was extracted when additional hydrophobin was not present, but with HFBII present 82% was extracted and with HFBI present 88% was extracted.

Example 24

Production of EGIcore-HFBI Fusion Proteins in *T. reesei* Δhfb2 Strain for Improved Partitioning of the Fusion Protein in ATPS

*Trichoderma reesei* strain QM9414 Δhfb2 (VTT-D-99726) was transformed essentially as described (Penttilä et al., 1987) using 10 μg of the plasmid pMQ113 (described in Example 1) together with 3 μg of the selection plasmid pTOC202 containing the amdS gene (Hynes et al., 1983; Tilburn et al., 1983) of *Aspergillus nidulans* encoding for acetamidase. pMQ113 contains an expression cassette for production of EGIcore-HFBI fusion protein under the control of cbh1 promoter and terminator sequences.

The Amd+ transformants obtained were streaked two times onto plates containing acetamide (Penttilä et al., 1987). Thereafter spore suspensions were made from transformants grown on Potato Dextrose agar (Difco). The production of the EGIcore-HFBI fusion protein was tested by slot blotting or Western analysis with EGI and HFBI specific antibodies from shake flask or microtiter plate cultivations carried out in minimal medium supplemented with Solka flock cellulose. The spore suspensions of the clones producing fusion protein were purified to single spore cultures on selection plates containing acetamide. To determine the best producers, production of the fusion protein was analyzed again from these purified clones as described above.

For partitioning experiments of the EGIcore-HFBI fusion protein in ATPS using the polyoxyethylene detergent C12-18EO5 the best production strain obtained in this study and as control strains VTT-D-98691 (QM9414 strain producing EGIcore-HFBI) and VTT-D-74075 (QM9414) were cultivated in shake flasks on medium containing Solka flock cellulose as described in Example 4.

Standard partitioning experiments as described in Example 5 are carried out with culture supernatants. After separation the volume ratio of the lighter and heavier phase is noted and the concentration factor for the fusion protein is calculated from it. Samples are also taken from the lighter and heavier phase and analysed with SDS-PAGE, Western blotting and activity measurements as described in Example 5. Partition coefficients (K) and yields (Y) are calculated as described in Example 5.

Example 25

Construction of Vectors for Expression of EGIcore-HFBII and EGIcore-SC3 Fusion Proteins Under the cbh1 Promoter of *T. reesei*

Figure 18:
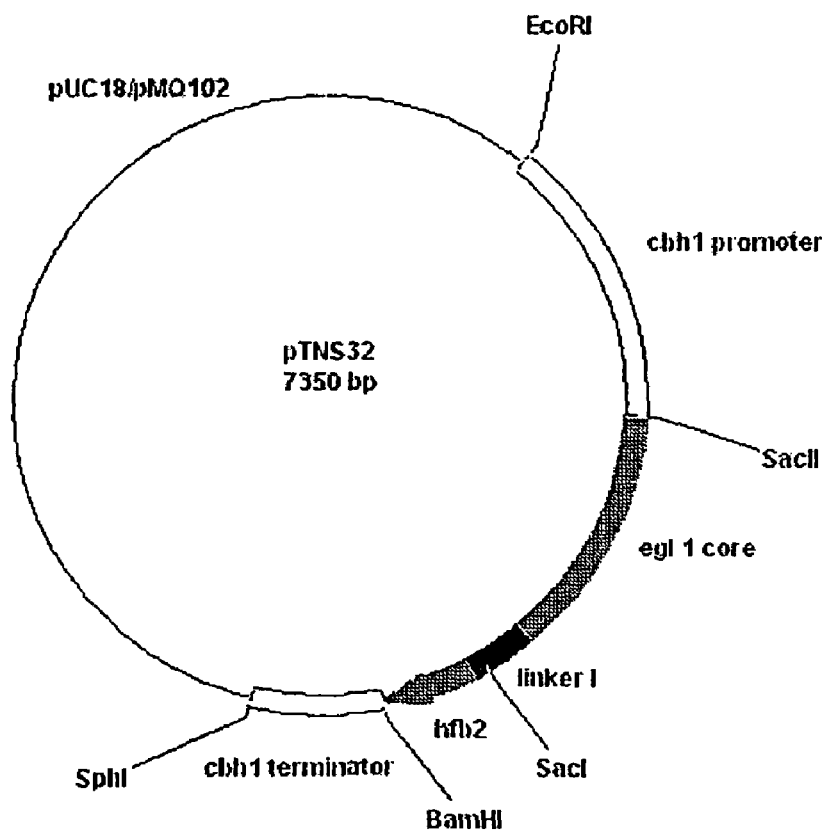
FIG. 18 shows the map of the plasmid pTNS32.

For construction of an expression vector for production of EGIcore-HFBII fusion protein, hfb2 (SEQ ID NO:20) coding region (from Ala-16 to the STOP codon) was amplified by PCR using phfb2 (Nakari-Setälä et al. 1997) as a template and as a 5' primer CGG AG<u>GAGCTCG</u> ACG ACT TCG AGC AGC CCG AGC TGC ACG CAG GCT GTC TGC CCT ACC GG (SEQ ID NO:21) and as a 3' primer TCA TTG GAT CCT TAG AAG GTG CCG ATG GC (SEQ ID NO:22). The sequence is bold in the 5' primer encodes for amino acids 413-425 of EGI and the underlined GAGCTC is a SacI site. The underlined GGATCC in the 3' primer is a BamHI site. The amplified fragment was digested with SacI and BamHI and ligated to pMQ113 cut with the same restriction enzymes. The resulting plasmid is pTNS32 (FIG. 18) and it carries the coding sequence for EGIcore-BFBII fusion protein under the control of cbh1 regulatory sequences (SEQ ID NO:5 and SEQ ID NO:7).

Figure 19:
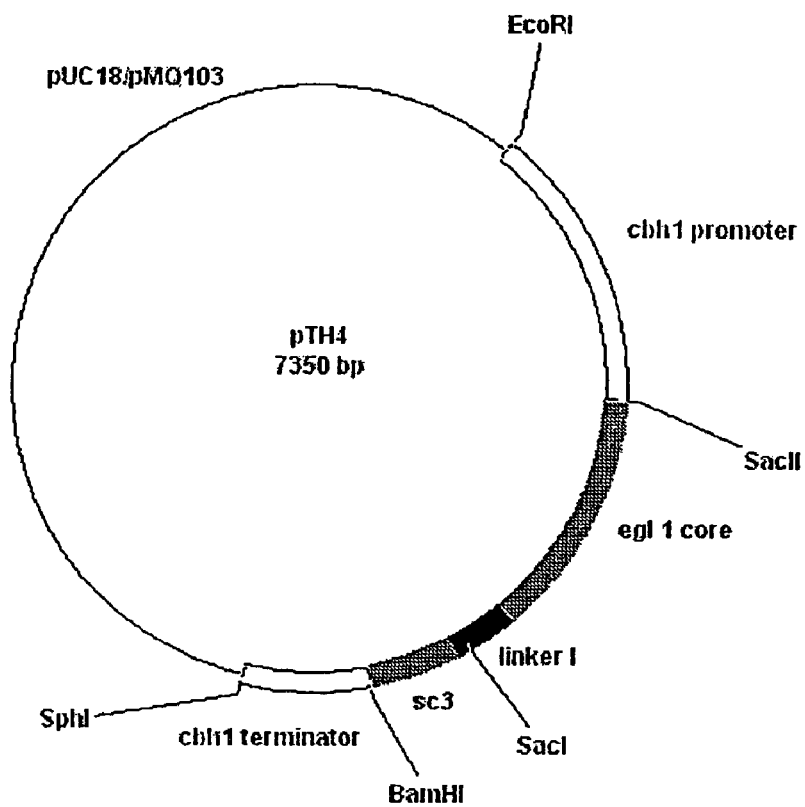
FIG. 19 shows the map of the plasmid pTH4.

For construction of an expression vector for production of EGIcore-SC3 fusion protein, SC3 cDNA (SEQ ID NO:23) was amplified with PCR using cSC3/pUC20 plasmid as a template and as a 5' primer ACT ACA CGG AG<u>GAGCTCG</u> ACG ACT TCG AGC AGC CCG AGC TGC ACG CAG GGT GGC CAC CCG GGC (SEQ ID NO:24) and as a 3' primer TCG TAC <u>GGATCC</u> TCA GAG GAT GTT GAT GGG (SEQ ID NO:25). The sequence is bold in the 5' primer encodes for amino acids 413-425 of EGI and the underlined GAGCTC is a SacI site. The underlined GGATCC in the 3' primer is a BamHI site. The amplified fragment was digested with SacI and BamIII and ligated to pMQ103 (described in Example 1) cut with the same restriction enzymes. The resulting plasmid is pTH4 (FIG. 19) and it carries the coding sequence for EGIcore-SC3 fusion protein under the control of cbh1 regulatory sequences (SEQ ID NO:5 and SEQ ID NO:7).

The cSC3/pUC20 plasmid contains the 411 bp SC3 cDNA from the translational start site to the STOP codon in a pUC20 vector. The translational start site has been constructed to a NcoI site and a BamHI site has been added after the translational STOP codon.

Example 26

Construction of a Vector for Expression of a HFBI-dCBD Fusion Protein Containing Hydrophobin I and Double Cellulose Binding Domains (CBD) Under the cbh1 Promoter of *T. reesei*

For construction of an expression cassette for production of HFBI-dCBD fusion protein under cbh1 promoter, the protein coding region of hfb1 was amplified with PCR using pEA10 (Nakari-Setälä et al. Eur. J. Biochem. (1996) 235: 248-255) as a template. GGA ATT CCGCGG ACT GCG CAT CAT GAA GTT CTT CGC CAT CGC C (SEQ ID NO:26) was used as a 5' primer in the PCR and TGA ATT CCATATGTT AGG TAC CAC CGG GGC CCA TGC CGG TAG AAG TAG AAG CCC CGG GAG CAC CGA CGG CGG TCT GGC AC (SEQ ID NO:27) as a 3' primer. The sequence in bold in the 5' primer is 16 bp of cbh1 promoter adjacent to translational start site of the corresponding gene and the underlined CCGCGG is a KspI site. The underlined and bold sequences in the 3' primer are NdeI and Asp718 sites, respectively. The sequence in Italics in the 3' primer encodes for a Methionine-containing linker (PGASTSTG-MGPGG) (SEQ ID NO: 41). The resulting fragment of 370 bp was digested with KspI and NdeI and ligated to pAMH110 (Nevalainen, K. M. H., Penttilä, M. E., Harkki, A., Teeri, T. T. and Knowles, J. (1991) In Molecular Industrial Mycology. Eds. Leong, S. A. and Berka, R. Marcel Dekker. New York) digested with same restriction enzymes. The resulting plasmid is pTNS29-2Asp.

For further cloning steps, an Asp718 site was removed from the pTNS29-2Asp polylinker. The vector was digested with SacI and BamHI and the cleaved vector ends were blunted with T4 DNA polymerase and ligated together. The resulting vector pTNS29 is missing the SacI, Asp718 and SmaI sites present in the pTNS29-2Asp polylinker.

Figure 20:
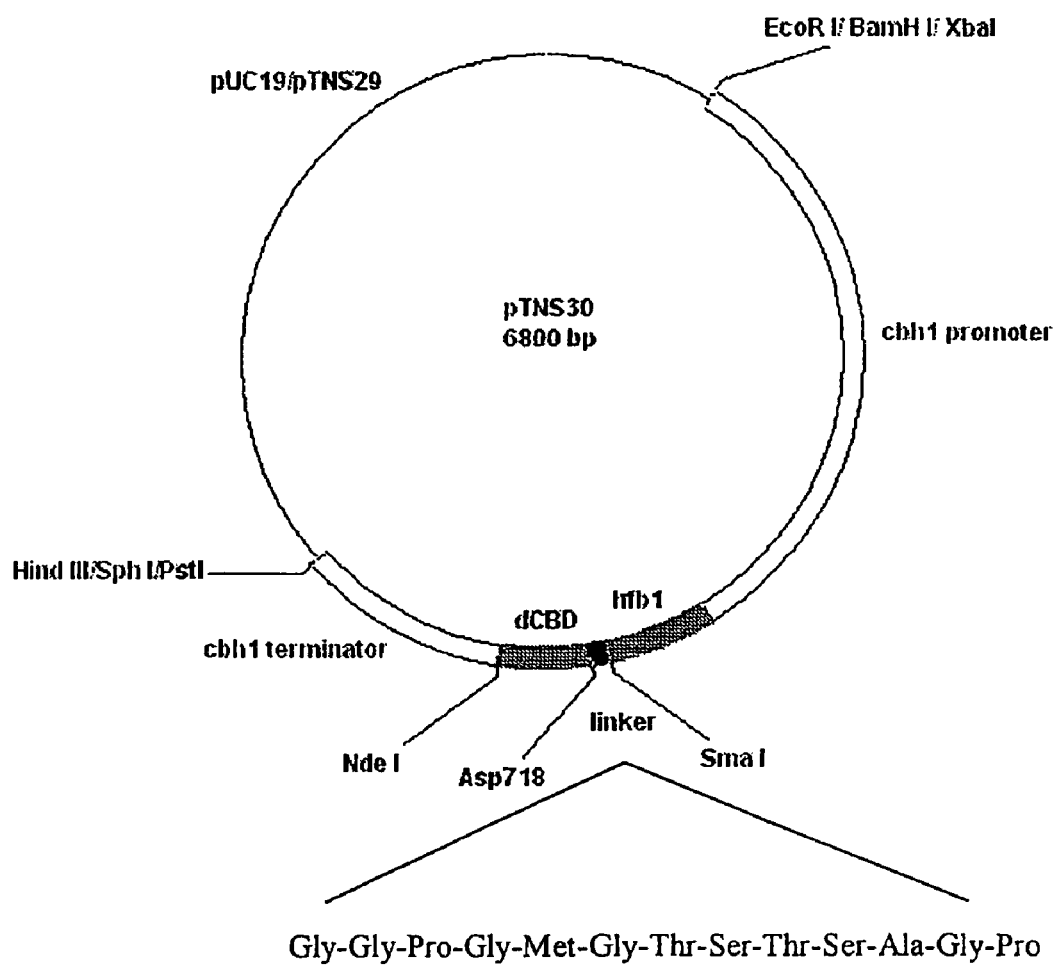
FIG. 20 shows the map of the plasmid pTNS30. The linker sequence is SEQ ID NO: 41.

In the next step, a double cellose binding domain (dCBD) was amplified with PCR using pTNS11 as a template. pTNS11 carries the coding sequence for a fusion protein containing 1*T. reesei* CBEHI CBD (41 N-terminal residues of CBHII) and CBHI CBD linked together via CBHI linker region (CBHI linker and CBD are the last 57 residues in CBHI). This DNA sequence originates from an *E. coli* expression vector B599 which is essentially the same as the one described by Linder et al. (J. Biol. Chem. (1996) 271:21268-21272). TGA ATT CGGTACCCA GGC TTG CTC AAG CGT C (SEQ ID NO:28) was used as a 5' primer in the PCR and TGA ATT CCATATGTC ACA GGC ACT GAG AGT AGT A (SEQ ID NO:29) as a 3' primer. The underlined sequences in the 5' and 3' primers are Asp718 and NdeI sites, respectively. The amplified fragment was digested with Asp718 and NdeI and ligated to pTNS29 digested with Asp718 and NdeI resulting in pTNS30.

pTNS30 (FIG. 20) expression vector thus carries the coding region for a fusion protein consisting of HFBI and double CBD linked in frame via the Methionine linker peptide (PGASTSTGMGPGG) (SEQ ID NO: 41). Expression of the fusion protein is regulated by the cbh1 transcriptional control sequences. The expression cassette may be released from the plasmid with EcoRI and SphI.

Example 27

Construction of Vectors for Expression of HFBI-Single Chain Antibody Fusion Proteins Under the cbh1 Promoter of *T. reesei*

Figure 21:
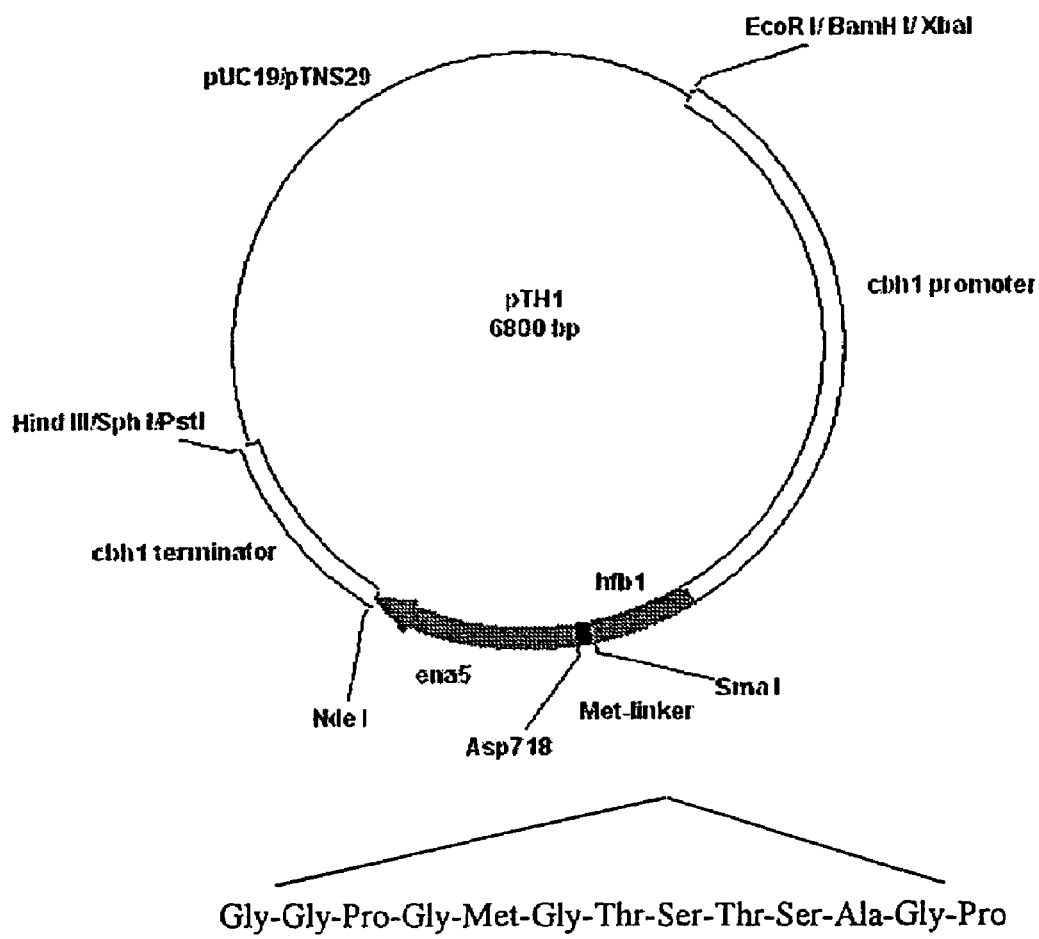
FIG. 21 shows the map of the plasmid pTH1. The linker sequence is SEQ ID NO: 41.

An expression vector was constructed for production of a fusion protein consisting of 1*T. reesei* HFBI protein in the N-terminus and in the C-terminus a single chain antibody recognizing a small molecular weight derivative of diarylalkyltriazole (ENA5ScFv). Production of the fusion protein is under the cbh1 regulatory sequences. For construction of HFBI-ENA5ScFv fusion protein, pENA5ScFv was digested with NcoI and XbaI. The fragment containing the ena5scfv gene and the histidine tail (6xHis) was blut-end cloned to pTNS29 resulting in pTH1 (FIG. 21). pENA5ScFv vector carries the coding region for ENA5 single chain antibody consisting of the variable domains of the heavy and light chains connected via a glycine serine linker and a 6x histidine tag at the C-terminal end. Transcription and secretion of the single chain antibody are under control of the tac promoter and pelB signal sequence, respectively (Takkinen et al., 1991). pTNS29 vector carries the hfb1 coding region of *T. reesei* followed by a linker sequence (ProGlyAlaSer-ThrSerThrGlyMetGlyProGlyGly) (SEQ ID NO: 41) under the control of cbh1 promoter and terminator sequences.

Figure 22:
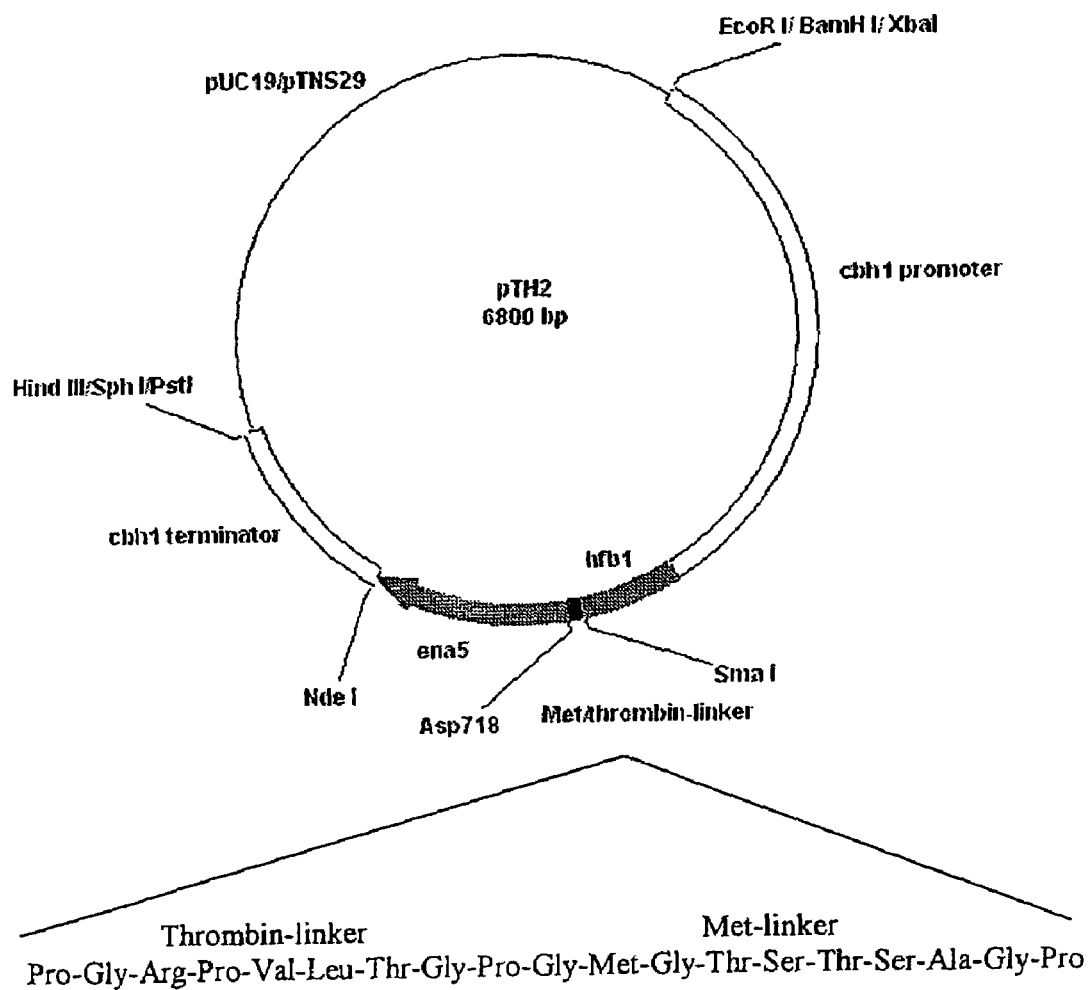
FIG. 22 shows the map of the plasmid pTH2. The linker sequence is SEQ ID NO: 40.

For construction of HFBI-ENA5ScFv fusion protein with thrombin cleavage site in the linker peptide, ena5scfv coding region (from Ala-23 to the STOP codon) and a peptide linker containing the thrombin cleavage site (Gly Thr Leu Val Pro Arg Gly Pro Ala Gla Glu Val Asn Leu Val) preceeding it was amplified with PCR using pENA5ScFv as a template and as a 5' primer GAA TTC GGTACC CTC GTC CCT CGC GGT CCC GCC GAA GTG AAC CTG GTG (SEQ ID NO:30) and as a 3' primer TGA ATT CCATATGCT AAC CCC GTT TCA TCT CCA G (SEQ ID NO:31). The sequence in bold in the 5' primer encodes the first 6 N-terminal residues of ENA5SCFV. The sequence in italics is a thrombin cleavage site and underlined GGT ACC is an Asp718 site. The sequence in bold in the 3' primer encodes the 6 C-terminal residues of ENA5ScFv and the underlined CA TATG is a NdeI site. The 790 bp PCR fragment was purified from agarose gel and ligated to pTNS29 resulting in pTH2 (FIG. 22).

Example 28

Construction of a Vector for Production of Class I Hydrophobin SC3 of *Schizophyllum commune* in *Trichoderma reesei* for ATPS A *T. reesei* stain producing class I hydrophobin SC3 of *S. commune* was constructed. For that purpose an expression vector carrying the SC3 cDNA under the control of hfb2 promoter and hfb1 terminator of *T. reesei* was constructed.

Figure 23:
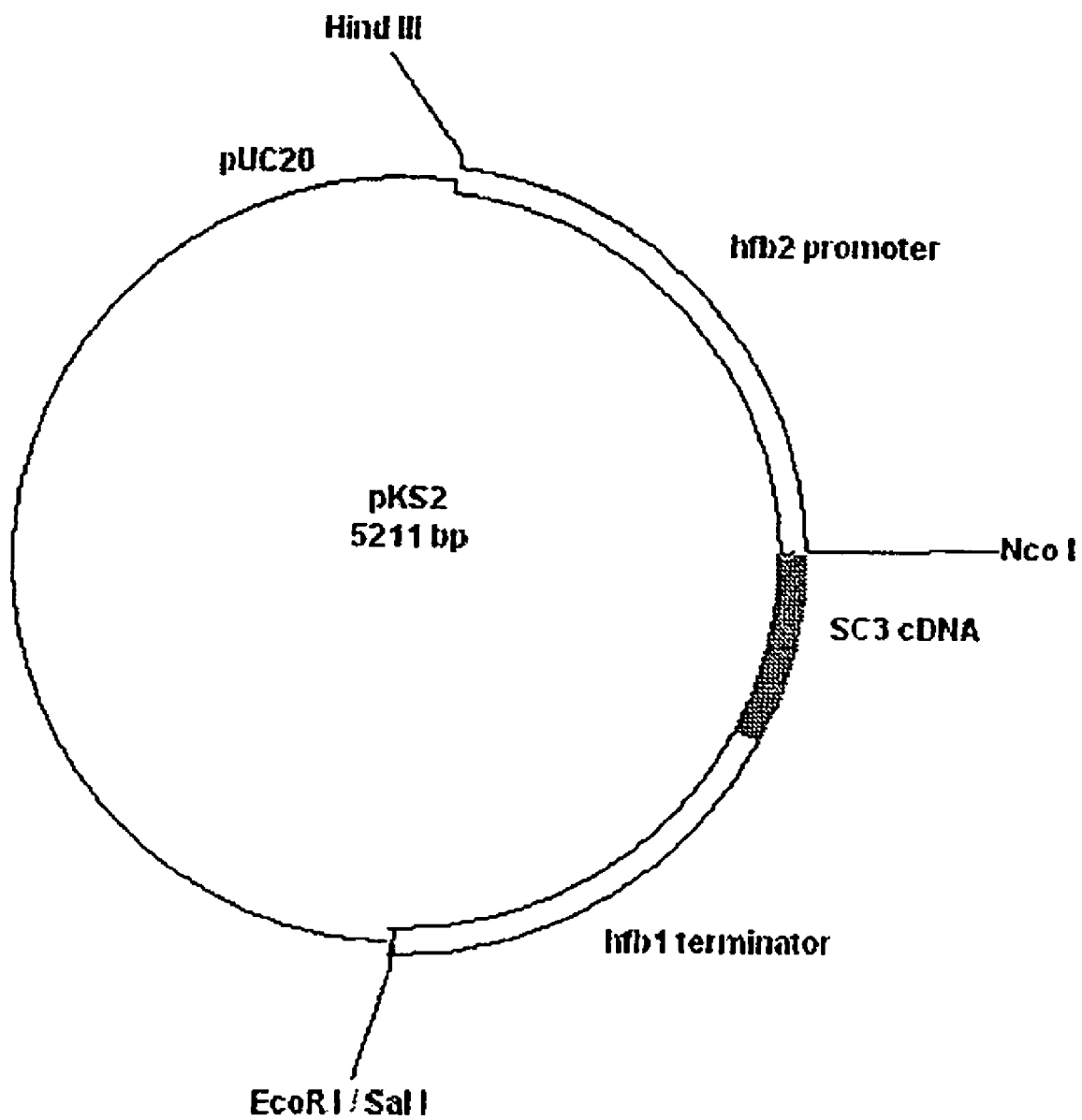
FIG. 23 shows the map of the plasmid pKS2.

The hfb1 terminator (SEQ ID NO:32) was amplified with PCR using as a template pEA10 (Nakari-Setälä et al. 1996) and as a 5' primer GACCTC GAT GCC CGC CCG GGG TCA AG (SEQ ID NO:33) and as a 3' primer GTCGAC ATT TCA TTT TAC CCC CCT CG (SEQ ID NO:34). The underlined sequences in the 5' and 3' primers are SacI and SalI sites, respectively. The PCR fragment was cut with SacI and SalI so that the SacI site was blunted with Klenow. The fragment was cloned into cSC3/pUC20 (described in Example 25) vector digested with SalI and BamHI where the BamHI was blunted with Klenow. In the next step, the hfb2 promoter (SEQ ID NO:35) was amplified with PCR using as a template pTNS8 (Nakari-Setälä et al. 1997) and using as a 5' primer AAGCTT GCA TGC CTG CAT CC (SEQ ID NO:36) and as a 3' primer CCATGG TGA AAG GTG GTG ATG GTT GG (SEQ ID NO:37). The underlined sequences in the 5' and 3' primers are HindIII and NcoI sites, respectively. The PCR fragment was digested with HindIII and NcoI and cloned in front of the SC3 cDNA in the plasmid obtained in the previous step and cut with the same restriction enzymes. The resulting plasmid is pKS2 (FIG. 23).

Example 29

Construction of *T. reesei* Strains Producing EGIcore-HFBII, EGIcore-SC3, HFBI-dCBD and IBI-Single Chain Antibody Fusion Proteins, and SC3 Hydrophobin

*Trichoderma reesei* strains VTT-D-74075 (QM9414), VTT-D-86271 (Rut-C30) and VTT-D-99676 (Rut-C30 Δhfb2) were co-transformed essentially as described (Penttilä et al., 1987) using 3-13 µg of the plasmids pTNS32, pTH1, pTH2, pTH4, pTNS30 and pKS2 and as the selection plasmids 1-3 µg pToC202 or pARO21. pToC202 carrying the amdS gene (Hynes et al., 1983; Tilburn et al., 1983) of *A. nidulans* and pARO21 carrying the *E. coli* hph gene have been described in Example 3. The Amd+ and Hyg+ transformants obtained were streaked three times onto plates containing acetamide and hygromycin, respectively (Penttilä et al., 1987). Thereafter spore suspensions were made from transformants grown on Potato Dextrose agar Difco).

The production of the fusion proteins EGIcore-HFBII, EGIcore-SC3, HFBI-dCBD and HFBI-ENA5ScFv and the SC3 hydrophobin was tested by slot blotting or Western analysis with EGI, SC3, CBD and HFBI specific antibodies from shake flask or microtiter plate cultivations carried out in minimal medium supplemented with either lactose or Solka flock cellulose. The spore suspensions of the fusion protein producing clones were purified to single spore cultures on selection plates (containing either acetamide or hygromycin). To determine the best producers, production of the fusion proteins was analyzed again from these purified clones as described above.

*T. reesei* strains selected for further cultivations are X46A (pTNS32, host QM9414), VTT-D-00793 (pTH4, host Rut-C30 Δhfb2), VTT-D-99727 (pTNS30, host Rut-C30 Δhfb2), VTT-D-00791 (pTH1, host Rut-C30) and VTT-D-00792 (pKS2, host Rut-C30 Δhfb2). These strains were cultivated as described in Example 4 and the culture supernatants were subjected to ATPS.

Example 30

Recovery of the Protein Product From the Enriched Detergent Phase After ATPS by Isobutanol or Other Solvents After phase separation has occurred and the hydrophobin or the hydrophobin fusion protein is enriched in the detergent phase (the enriched phase), the protein can be recovered to an aqueous buffer by addition of isobutanol or other solvent. For example a series, of identical extractions of 0.05 g/l HFBI in 50 mM acetate buffer was made with 2% Berol 532. To separate tubes 10% final concentration of either isobutanol, n-amyl alcohol, octanol, or octane was added. and the fraction of hydrophobin recovered to the aqueous phase was analyzed. It was found that 100% was recovered with isobutanol, 89% with n-amyl alcohol, 81% with octanol and 70% with octane. Fractions were analyzed by HPLC as described in Example 38.

Example 31

Separation of EGIcore-HFBII Fusion Protein in ATPS

*T. reesei* strain X46A was grown in shake flasks on 3% lactose medium as described in Example 4. C12-18EO5 detergent was added to a final concentration of 5% to the culture supernatant. After mixing the system was allowed to settle and the enriched detergent phase was subjected to further extraction with an equal volume of isobutanol. After buffer exchange on Biogel P-6 (Bio-Rad, USA) gel filtration media, the extracted protein was analysed by ion exchange chromatography using a Mono Q (Amersham Pharmacia, Sweden) column equilibrated with 15 mM acetate and eluted using a linear gradient of NaCl. Separation of the EGIcore-HFBII fusion protein to the detergent phase was verified by analyzing the eluted peak fraction from the Mono Q chromatography run by its activity on 4-methylumbelliferyl cellobioside as well as its re-extraction by ATPS.

Example 32

Separation of EGIcore-SC3 Fusion Protein in ATPS

Culture filtrate of *T. reesei* strain VTT-D-00793 producing EGIcore-SC3 fusion protein was subjected to APTS by adding 5% final concentration of C12-18EO5. After the settling, the phases were separated and the fusion protein enriched detergent phase was further treated with an equal volume of isobutanol which removes the detergent to the isobutanol and leaves the protein in the aqueous phase. The resulting fusion protein enriched aqueous phase was then desalted on Biogel P-6 (Biorad, USA). Separation of fusion protein to the detergent phase was verified by analyzing the enzymatic activity of the EGIcore fusion partner on 4-methylumbelliferyl cellobioside in that phase.

Example 33

Separation of HFBI-dCBD Fusion Protein in ATPS

Figure 24:
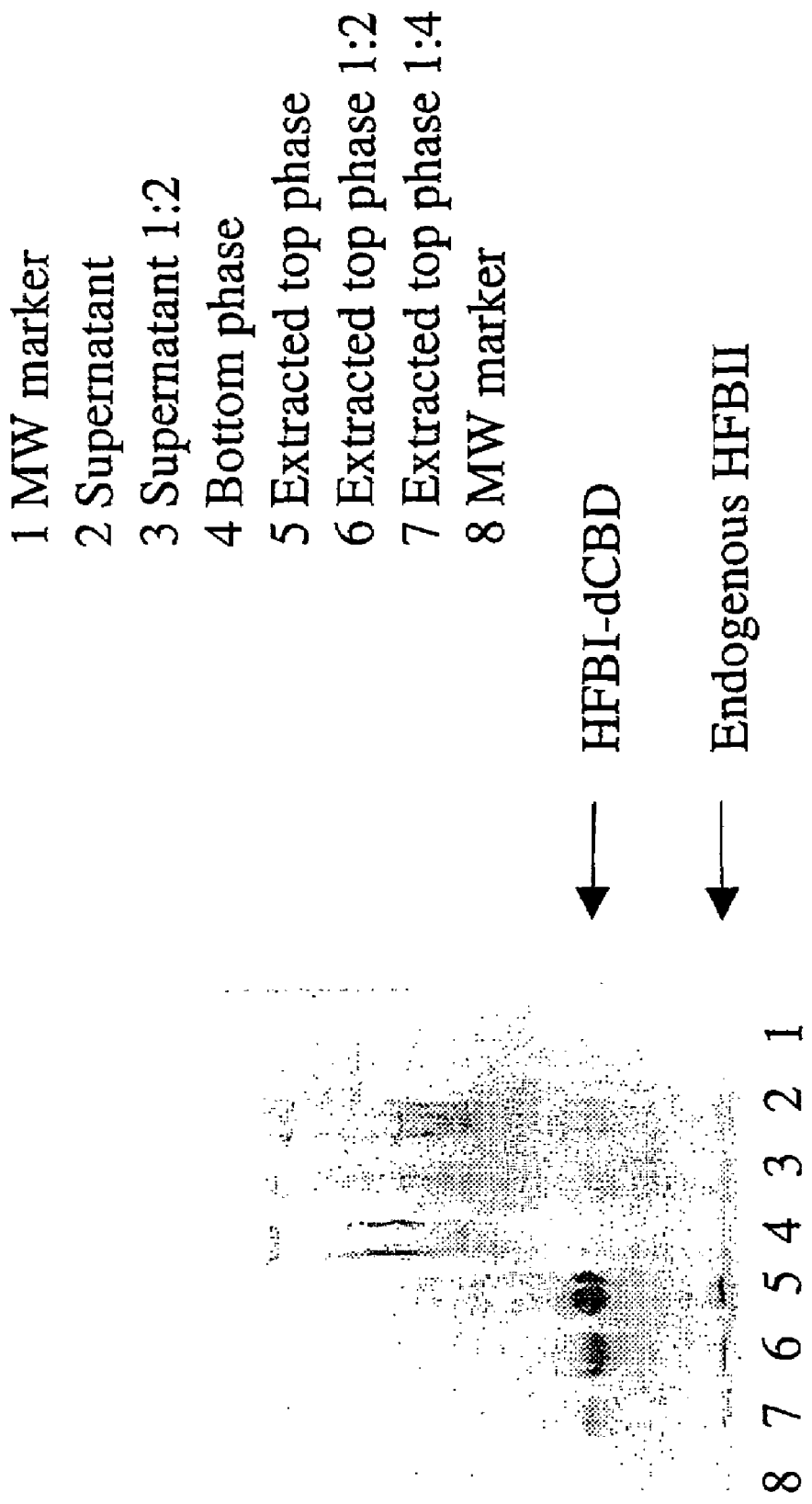
FIG. 24 SDS gel showing the purification of HFBI-dCBD in a Berol 532 ATPS system.

*T. reesei* strain VTT-D-99727 producing HFBI-dCBD fusion protein was grown on lactose-containing medium as described in Example 4. Berol 532 was added to a final concentration of 2% to 500 ml of culture supernatant. The mixture was allowed to settle and the phases separated in a separation funnel. The enriched top phase (10 ml) was extracted with an equal volume of isobutanol and 50 mM acetate buffer pH5. The fusion protein was selectively enriched to the buffer in the separation as shown by SDS gel electrophoresis (FIG. 24).

Example 34

Recovery of the HFBI-dCBD Fusion Partners After Chemical Cleavage

HFBI-dCBD protein produced by the strain VTT-D-99727 has a methionine (PGASTSTGMGPGG) (SEQ ID NO: 41) designed in the linker region between the BFBI and the dCBD, which would enable the recovery of the native HFBI and dCBD after chemical cleavage with CNBr.

The HFBI-dCBD fusion protein was purified as described in Example 33. The resulting water phase (~108 ml) still contained a small amount of CBHI and free hydrophobin in addition to the HFBI-dCBD fusion (FIG. 24). Further purification of the sample was performed by chromatography. The sample was desalted on a Biogel P-6 column equilibrated with 50 mM sodium acetate buffer pH 5.5, diluted 1+3 with water and applied on a CM-Sepharose FF column equilibrated with 10 mM sodium acetate buffer pH 5.5. The CBHI protein was found in the flow through and the purified HFBI-dCBD protein was eluted with 0.2M NaCl.

A sample of purified HFBI-dCBD protein was evaporated in speed-vac almost to dryness. CNBr cleavage was performed by adding a solution of CNBr in 0.1 M HCl (5 mg/ml) to the evaporated sample in 5 times weight excess. The reaction was allowed to continue for 24 h at room temperature (in dark). A 10 times volume of water was added and the sample was evaporated in speed-vac almost to dryness. The evaporated sample was diluted in 50 mM Tris-HCl pH 7 and the cleavage was confirmed by HPLC analysis as described in Example 37.

The treatment was further optimised by using different concentrations of HCl and incubation times. The final CNBr treated sample was subjected to ATPS as described in Example 33. HFBI was found in the top-phase and the dCBD in the bottom phase, thus leading to a separation of both fusion partners.

Example 35

Separation of HFBI-Single Chain Antibody Fusion Protein in ATPS

Figure 25:
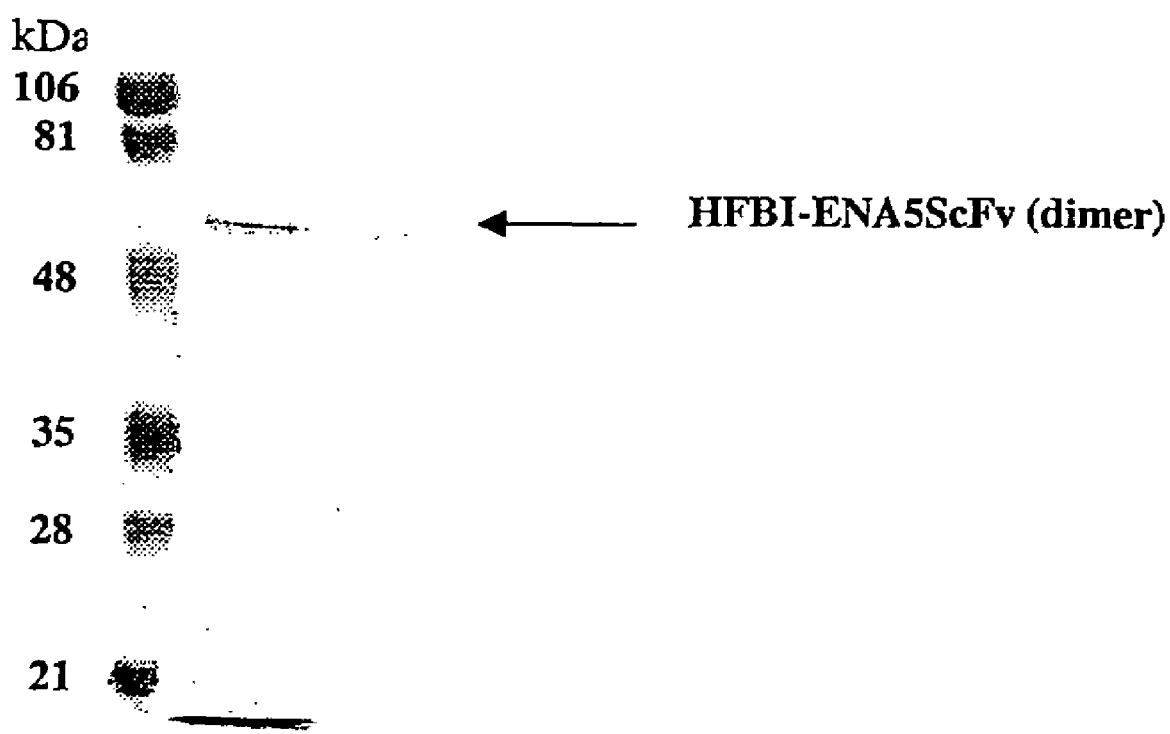
FIG. 25 Western analysis of the partitioning of BBI-ENA5ScFv fusion protein in two-phase separation using 4% of the detergent C12-C18EO5. Lanes from left: (1) Molecular weight marker, (2) Top (enriched) phase of the strain VTT-D-00791, (3) Bottom (depleted) phase of the strain VTT-D-00791.

Strain VTT-D-00791 was cultivated for 7 days on medium containing 10 g/l potassium phtalate, 15 g/l $KH_2PO_4$, 5 g/L $4)_2SO_4$ and 3% lactose and 0.2% peptone. 30 ml of culture medium was subjected to ATPS using 4% C12-18-EO5 detergent as described in Example 5. After removal of the bottom phase, the detergent phase was extracted by isobutanol. Proteins from the water phase after detergent extraction and the bottom phase of the isobutanol extracted detergent phase were precipitated with trichloroacetic acid (final concentration 10%), resuspended in SDS-PAGE sample buffer (taking into account the concentration factor of the isobutanol extracted detergent phase) and analysed by Western blotting using HFBI specific antibodies. The fusion protein runs as a dimer (approximately 70 kDa) in SDS-PAGE under the conditions used as seen in FIG. 25. The water phase sample still contained a small amount of fusion protein. Nevertheless, separation of the fusion protein can be obtained by ATPS.

Example 36

Separation of SC3 Hydrophobin in ATPS

Figure 26:
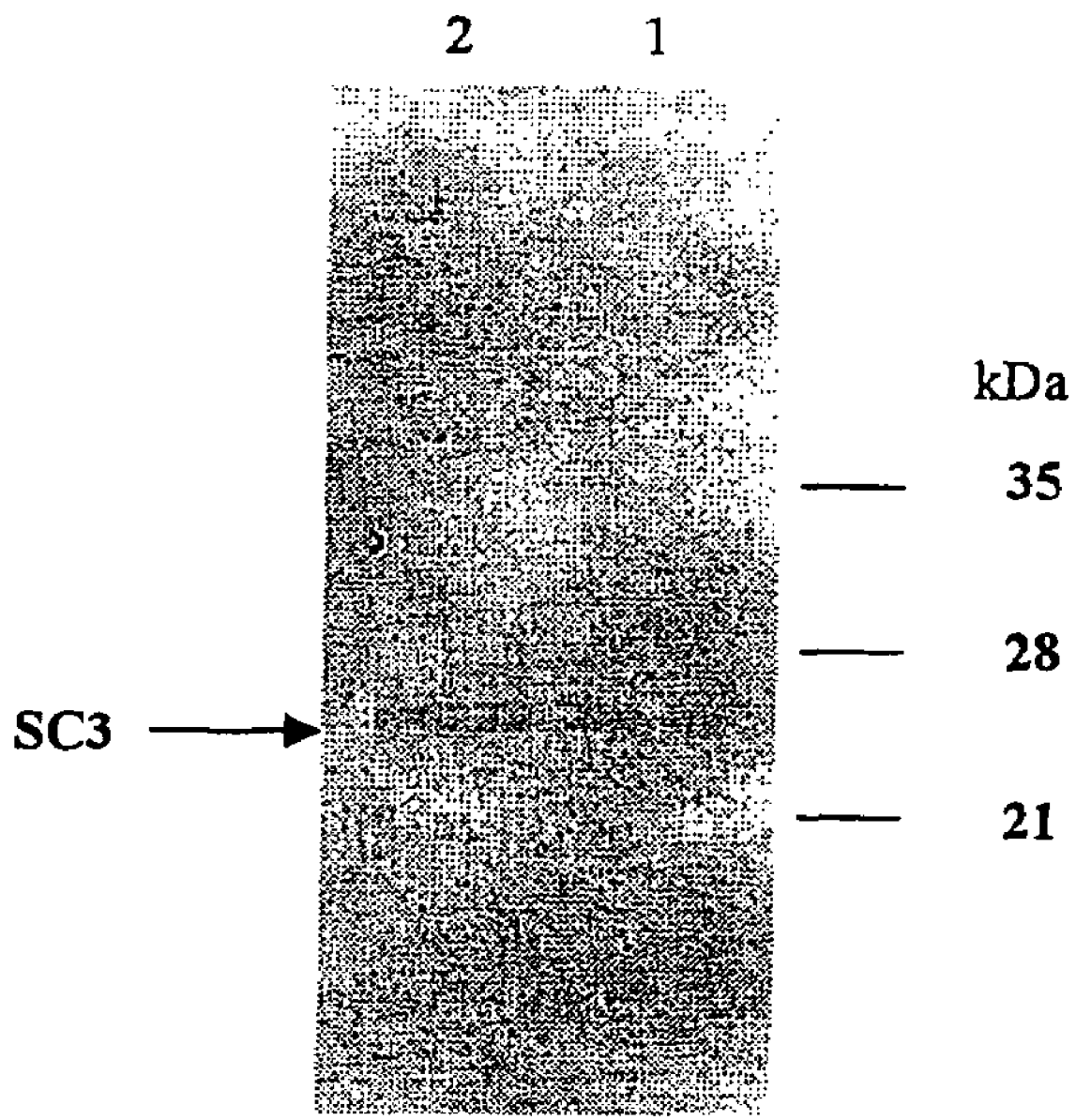
FIG. 26 Western analysis of the partitioning of SC3 hydrophobin using SC3 specific antibodies. Lane 1, Bottom phase of the strain VTT-D-00792, Lane 2, Top phase of the strain VTT-D-00792.

SC3 hydrophobin producing strain VTT-D-00792 was cultivated in shake flasks on lactose-containing medium as described in Example 4. Soluble secreted proteins produced by the fungus were precipitated with trichloroacetic acid. Precipitated proteins were solubilized in trifluoroacetic acid to dissociate the SC3 aggregates whereafter the acid was evaporated with a stream of air. The treated proteins were solubilized in 2 ml water containing 2.5% of the detergent C12-18EO5. Phase separation was carried out as described in Example 5. Samples were taken from the lighter and heavier phase and analysed by Western blotting using SC3 specific antibodies. On the basis of this analysis, SC3 hydrophobin partitions to the detergent phase (FIG. 26).

Example 37

Separation of Nisin in ATPS 1 mg of pure nisin (Sigma) (equals to 1000 IU) in 50 mM sodium acetate buffer pH 5 was subjected to ATPS using 2% of the detergent C12-18EO5 at 30° C., and the phases were allowed to settle. After removal of the bottom phase, the detergent phase was extracted by isobutanol which removes the detergent to the isobutanol and leaves nisin in the aqueous phase. Separation of nisin to the enriched aqueous phase was assayed testing nisin bioactivity as described by Qiao et al. 1996. Comparison of the halos on the assay plate produced by the enriched phase and the nisin controls indicated that nisin had separated to the detergent phase with a concentration factor of approximately 5.

Example 38

Preparative Purification of HFBI and HFBII in ATPS

Figure 27:
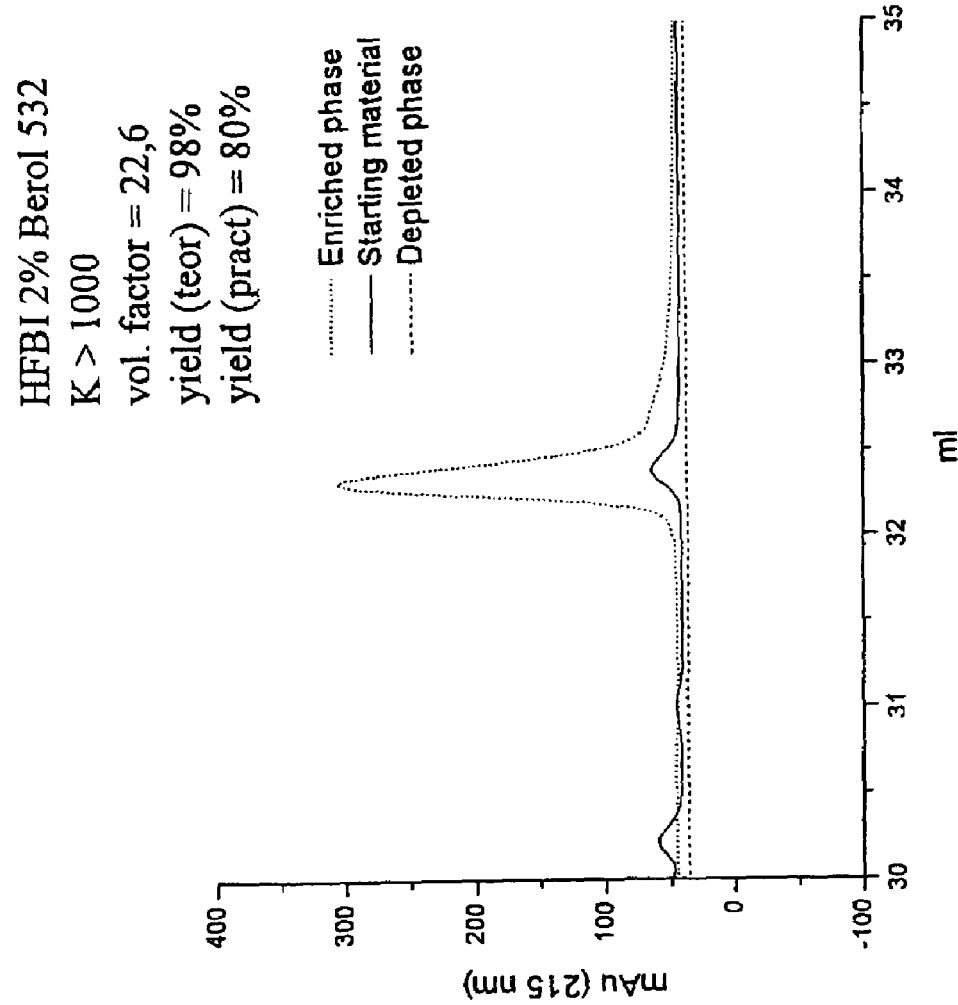
FIG. 27 HPLC analysis for monitoring of the partitioning of HFBI in 2% Berol 532.
Figure 28:
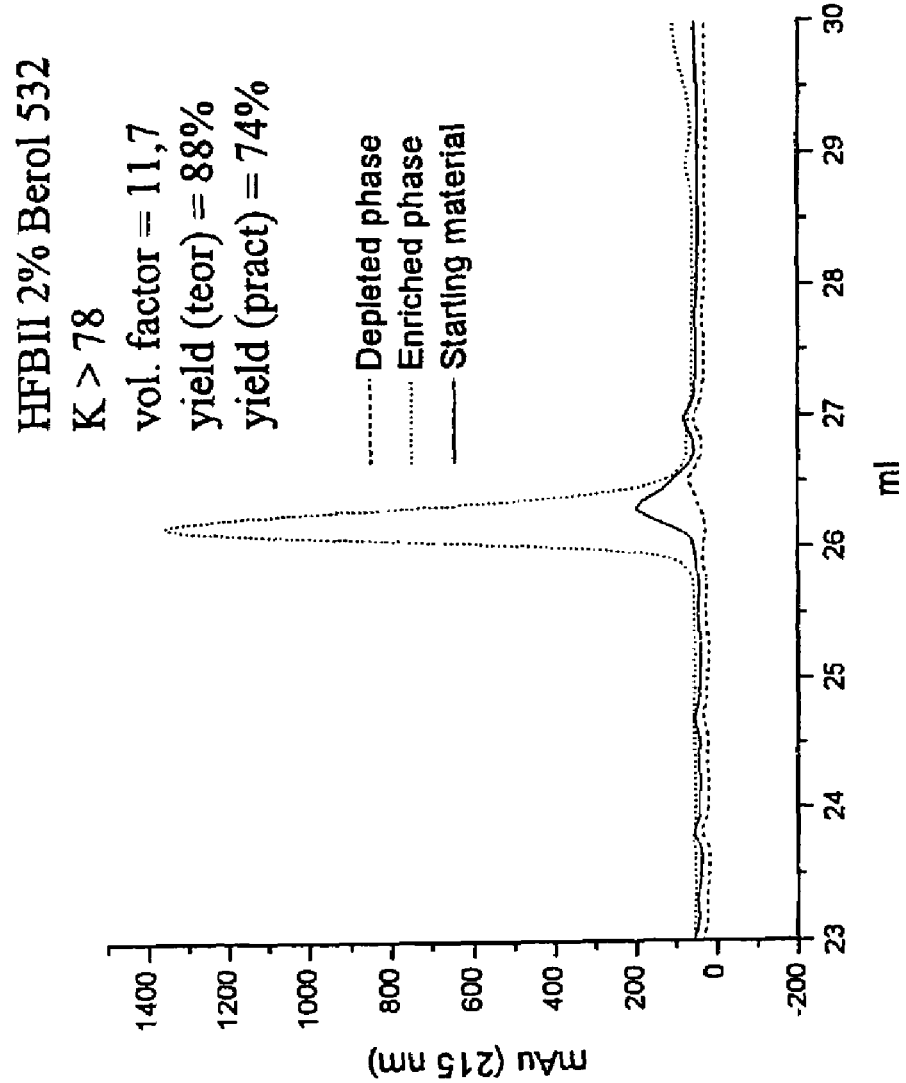
FIG. 28 HPLC analysis for monitoring of the partitioning of HFBII in 2% Berol 532.

For preparative purposes, HFBI and HFBII were extracted from 0.5 l of culture supernatants from cultivations carried out on media containing glucose or cellulose as described in Example 4.2% (w/w) detergent was added to the culture supernatant which was mixed and then allowed to settle in a separation funnel at 20° C. if C11EO2 (Berol 532) was used and 30° C. if C12-18EO5 (Henkel) was used. The detergent phase (enriched phase) was collected and mixed with an equal volume of isobutanol. When C11EO2 was used an equal volume of 50 mM acetate buffer was also added. The remaining culture supernatant is the depleted phase. To follow the purification, analytical HPLC was run on samples from each step (FIGS. 27 and 28). On the basis of HPLC analysis, both HFBI and HFBII partitioned well to both of the detergents. When C11EO2 was used, K values of >1000 and >78 were obtained for HFBI and HFBII, respectively.

Water phase after isobutanol extraction was collected and further purified on a Vydac 1×20 cm semipreparative C4 column (Vydac, USA) equilibriated with 0.1% trifluoro acetic acid in water and eluting with a linear gradient of 0.1% trifluoro acetic acid in acetonitrile. The proteins were then lyophilized. In analytical runs a 4.6 mm×20 cm Vydac C4 column was used.

Example 39

Screening for Separation Conditions using Purified HFBI and HFBII

HFBI and HFBII which were purified from culture supernatants in ATPS, further purified by preparative HPLC and lyophilized as described in Example 38 were dissolved in water to a concentration of 0.5 mg/ml. The stock solutions were then diluted with the buffer appropriate for the experiment. 50 mM acetate buffer pH5, 50 mM glycine pH 3, 50 mM HEPES pH 7 was used for pH screening and NaCl or $4)_2SO_4$ in acetate buffer was used for ionic strength experiments. The surfactant was weighed with the appropriate amount of hydrophobin solution and incubated in 0, 20, 30, 40° C. and the amount of hydrophobin in the depleted phase determined. Partitioning coefficients were calculated from the change in concentration and the volume ratios and are presented in the tables below.

Table presenting K-values for the separation of hydrophobins with different surfactants and temperature.

|  | Temperature | Henkel | Berol 532 | Berol 266 | Triton x114 |
|---|---|---|---|---|---|
| HFBI | 0° C. | 0.1 | 368 | NP | NP |
|  | 20° C. | 0.4 | 1961 | NP | NP |
|  | 30° C. | 85 | 2970 | NP | 0.9 |
|  | 40° C. | 148 | 682 | 28 | 69 |
| HFBII | 0° C. | NP | 76 | NP | NP |
|  | 20° C. | 1.0 | 139 | NP | NP |
|  | 30° C. | 67 | 194 | NP | 4.0 |
|  | 40° C. | 44 | 102 | 19 | 44 |

NP = no phase separation

Table presenting the effect of different salt concentrations at 40° C. on K-values

|  | Henkel | Berol 532 | Berol 662 | Triton x114 |
|---|---|---|---|---|
| HFBI 50 mM buffer | 244 | 578 | 13 | 39 |
| +1 M NaCl | 239 | 33 | 198 | 241 |
| +1 M $(NH_4)_2SO_4$ | 0.9 | 3.2 | 176 | 612 |
| HFBII 50 mM buffer | 36 | 80 | 16 | 58 |
| +1 M NaCl | 14 | 87 | 61 | 38 |
| +1 M $(NH_4)_2SO_4$ | 3.1 | 351 | 95 | 35 |

Table presenting the K-values for the partitioning of hydrophobins in Berol 532 at different conditions.

|  | HFBI 0° C. | HFBI 20° C. | HFBII 0° C. | HFBII 20° C. |
|---|---|---|---|---|
| 50 mM acetate pH5 | 298 | 614 | 76 | 127 |
| +1M NaCl | 614 | 3781 | 131 | 199 |
| +1M $(NH_4)_2SO_4$ | 931 | 44 | 203 | 139 |
| pH3 | 614 | 1881 | 73 | 160 |
| pH7 | 361 | 614 | 54 | 126 |

Example 40

Purification of a New Putative *T. reesei* Hydrophobin on the Basis of its Separation in ATPS, and Cloning of the Corresponding Gene

*T. reesei* strain VTT-D-99726 (QM9414 Δhfb2) was cultivated on lactose-based medium in 15 fermentor as described in Example 4. After cultivation, 1 l of the culture filtrate was subjected to ATPS with 5% polyoxyethylene detergent C12-18EO5. After phase separation at 30° C., detergent phase was separated from the depleted aqueous phase and analysed by SDS-PAGE. The analysed sample contained a protein which was about 7.5 kDa. In addition, some larger proteins were present. These were removed by hydrophobic interaction chromatography on a Phenyl-Sepharose FF column equilibriated with 50 mM sodium acetate—1 M $(NH_4)_2SO_4$ buffer. The proteins were eluted with descending $(NH_4)_2SO_4$ salt gradient. Fractions containing the ca. 7.5 kDa protein were pooled and concentrated, and analysed by mass spectrometry. This revealed that the purified protein was degraded to three peptides (2486, 2586 and 2709 Da), which were held together by disulphide linkages. The N-terminal amino acid sequence from the 2486 Da peptide was ANAFCPEGLLYTNPLCCDLL (SEQ ID NO: 46), which on the basis of position of cysteines and on sequence comparison to known hydrophobins is typical to a hydrophobin.

Degenerated primers were designed on the basis of this amino acid sequence as well as on the basis of the sequence obtained from the 2586 Da peptide. These primers were used in RT-PCR (RobusT RT-PCR Kit, Finnzymes) with RNA isolated from the same cultivation from where the protein was purified. The 140 bp fragment obtained from the RT-PCR reaction was sequenced. The obtained sequence contained a part that was coding for the 2486 Da peptide used to design the PCR primer confirming that the PCR product corresponds to the purified protein.

Example 41

Purification of EGIcore-HFBI in ATPS in Pilot Scale

The strain VTT-D-99702 producing EGIcore-HFBI fusion under the cbh1 promoter was cultivated in pilot scale fermentor in 1200 L on minimal medium containing 4% lactose, 0.4% peptone and 0.1% Yeast Extract for 4 days. Cultivation temperatures were 28° C. or alternatively the temperature was changed during the cultivation from 27° C. to 22° C. in a step-wise manner. Production level of the fusion protein was a few grams per liter. After the end of the cultivation, the mycelium was separated by means of a rotating vacuum drum filter using Celite 535 diatomaceous earth as filter aid.

In separation 1, 1100 L of the supernatant was transferred into the meanwhile cleaned bioreactor, adjusted to the separation temperature of 24.7° C. and mixed with salt and detergent to give 0.15 M ammonium dihydrogen phosphate and 4.1% of detergent C12-18EO5. The phases were left to separate by gravity settling and the heavier phase removed through the bottom valve. A parallel experiment in 10 ml volume was carried out to investigate the effect of scale up on the separation of the fusion protein. The partition coefficient and the concentration factor were equal for the 10 ml and 1200 L separation within the measurement error. The separated detergent phase was re-extracted using the detergent phase from the first extraction by replacing half of the volume of the bottom phase by tap water. The salt concentration was adjusted to 0.25 M ammonium dihydrogen phosphate at 30° C. K and Y values of the separations are presented in the below Table.

Alternatively in separation 2, 10 ml of drum filtrated culture medium samples were subjected to ATPS at 25° C. using 4.1% C12-18EO5 detergent and 1.15 M $(NH_4)H_2PO_4$. K and Y values after one separation step are presented in the Table below.

Table presenting extraction experiments of culture supernatants from different pilot scale cultivations

| Separation | Cultivation temperature | Concentration factor | K | Y [%] |
|---|---|---|---|---|
| Separation 1 | 27° C. → 22° C. | 3.4 | 3.8 | 59 |
| Re-extraction |  |  | 8 | 70 |
| Separation 2 | 29° C. | 2.8 | 8.3 | 81 |

Example 42

Separation of EGI, EGIcore-HFBI Fusion Protein and HFBI Hydrophobin in Robust Micelle/Polymer Systems Separations were performed with purified samples. HFBI was purified by two-phase separation and HPLC as described in Example 38. EGIcore-HFBI was purified by two-phase extraction as described in Example 5 followed by desalting on a Biogel P-6 column equilibrated with 20 mM sodium acetate puffer pH 6 containing 150 mM NaCl. The purified proteins were subjected to ATPS using different micelle/polymer systems.

The table below presents partitioning coefficients of pure EGI, BFBI and EGIcore-HFBI at constant tie-line length, in the different systems, Triton X-114/water system (4.1% wt.)

at 31.5° C., Triton X-100/Reppal/water system (8.1% wt./ 8.2% wt.) and Triton X-114/Reppal/water system (5.0% wt./4.0% wt.) at 21° C. The standard deviation is shown within the brackets. The systems were buffered with 25 mM sodium acetate, pH 4.0. K>1 is equivalent to a preferred protein partitioning to the micelle rich phase.

|  | EGI $K_{EGI}$ | HFBI $K_{HFB}$ | $K_{EGIHFB}$ | EGICORE-HFBI Yield (%) top phase |
|---|---|---|---|---|
| TRITON X-114 | 0.6 (0.1) | 21.5 (1.5) | 8.4 (1.0) | 85 |
| TRITON X-100/ REPPAL | 0.9 (0.1) | — | 1.7 (0.1) | 56 |
| Triton X-114/ Reppal | 0.7 (0.1) | 11.0 (1.1) | 15.4 (2.9) | 91 |

REFERENCES

Albertsson, P. A. (1986). Partition of Cell Particles and Macromolecules, John Wiley & Sons, New York.

Arntz, C. and Tudzynski, P. (1997). Identification of genes induced in alkaloid-producing cultures of *Claviceps* sp. Curr. Genet. 31:357-360.

Bender, W. and Koglin, B. (1986). Mechanische Tremung von Bioprodukten. Chem.-Ing.-Tech., 58:565-577.

Berggren K., Veide A., Nygren P.-A. and Tjerneld F. (1999). Genetic engineering of protein-peptide fusions for control in thermoseparating aqueous two-phase systems. Biotechnol. Bioeng. 62:135-144.

Bhikhabhai, R., Johansson, G. and Petterson, G. (1984). Isolation of cellulolytic enzymes from *Trichoderma reesei* QM 9414. J. Appl. Biochem. 6:336-345.

Bordier C. (1981). Phase Separation of Integral Membrane Proteins in Triton X-114 Solution. J. Biol. Chem. 25:1604-1607.

Carpenter, C. E., Mueller, R. J., Kazmierczak, P., Zhang, L., Villalon, D. K. and van Alfen, N. K. (1992). Mol. Plant-Microbe Interact. 4:55-61.

Gietz, D., St. Jean, A., Woods, R. A. and Schiestl, R. H. (1992). Improved method for high efficiency transformation of intact yeast cells. Nucl. Acid. Res. 20:1425.

Hassinen C., Köhler K., Veide A. (1994). Polyethylene glycol-potassium phosphate aqueous two-phase systems: A study using model proteins. Biotechnol. Bioeng. 44:626-635

Heusch, R. and Kopp, F. (1988). Structures in aqueous solutions of nonionic tensides. Progress in Colloid & Polymer Science, 77:77-85.

Hustedt, H., Kroner, K. and Kula, M R. (1985). Applications of Phase Partitioning in Biotechnology. In: Walter, H., Brooks, D. E. and Fisher, D. (eds.), Partitioning in Aqueous Two-Phase Systems Theory, Methods, Uses and Applications to Biotechnology, pp. 529-587.

Hynes, M. J., Corrick, C. M. and King, J. A. (1983). Isolation of genomic clones containing the amdS gene of *Aspergillus nidulans* and their use in the analysis of structural and regulatory mutations. Mol. Cell. Biol. 3:1430-1439.

Johansson, H.-O., Karlström, G., Tjerneld, F. and Haynes, A. C. (1998). Journal of Chromatography B, 711:3-17.

Kershaw, M. J. and Talbot, N. J. (1998). Hydrophobins and repellents: proteins with fundamental roles in fungal morphogenesis. Fungal Gen. Biol. 23:18-33.

Kula M-R. (1979). Extraction and Purification of Enzymes Using Aqueous Two-Phase Systems. In: Wingard L; Goldstein, L (eds.), Applied Biochemistry and Bioengineering. New York, Academic Press, pp. 71-95.

Kula, M-R., Kroner, K. H., Hustedt, H. and Schüke, H. (1981). Technical aspects of extractive enzyme purification. Ann. N.Y. Acad. Sci., 369:341-354.

Kula, M-R., Kroner, K. H. and Hustedt, H. (1982). Purification of enzymes by liquid-liquid extraction. In: Fiechter, A. (ed.), Advances in Biochemical Engineering, Springer Verlag, Berlin, pp. 74-118.

Kula, M-R. (1985). Liquid-Liquid Extraction of Biopolymers. In: Humphrey A; Cooney C L (eds.), Comprehensive Biotechnology, Vol. 2. Pergamon Press, New York, pp. 451-471.

Kula, M-R. (1990). Bioseparation, 1:181-189.

Köhler, K., Ljungquist, C., Kondo, A., Veide, A. and Nilsson B. (1991), Engineering proteins to enhance their partition coefficient in aqueous two-phase systems. Bio/Technology 9:642-646.

Linder, M., Salovuori, I., Ruohonen, L. and Teeri, T. T. (1996). Characterization of a double cellulose-binding domain. J. Biol. Chem. 271:21268-21272.

Lora, J. M., de la Cruz, J., Benitez, T., Llobell, A. and Pintor-Toro, J. A. (1994). Mol. Gen. Genet. 242:461-466.

Lora, J. M., Pintor-Toro, J. A., Benitez, T. and Romero, L. C. (1995). Mol. Microbiol. 18:377-382.

Mach et al., (1994) Curr. Genet. 6:567-570.

Minuth, T., Thömmes, J. and Kula, M-R. (1995). Extraction of cholesterol oxidase from *Nocardia rhodochrous* using a nonionic surfactant-based aqueous two-phase system. J. Biotechnol. 38:151-164.

Minuth, T., Thömmes, J. and Kula, M-R. (1996). A closed concept for purification of the membrane-bound Cholesterol-Oxidase from *Nocardia rhodochrous* by surfactant-based cloud-point extraction, organic solvent extraction and anion-exchange chromatography. Biotechnol. Appl. Biochem. 23:107-116.

Nakari, T., Onnela, M.-L., Ilmén, M., Nevalainen, K. M. H. and Penttillä, M. (1994) Fungal promoters active in the presence of glucose. International Patent Appl. WO 94/04673.

Nakari-Setälä et al. (1996). Eur. J. Biochem. 235:248-255.

Nevalainen, K. M. H., Penttilä, M. E., Harkki, A., Teeri, T. T. and Knowles, J. (1991) The Molecular Biology of *Trichoderma* and Its Application to the Expression of Both Homologous and Heterologous Genes. In Molecular Industrial Mycology. Leong, S. A. and Berka, eds., R. Marcel Dekker. New York, p. 129-148.

Pack, P., Kujau, M., Schroeckh, V., Knupfer, U., Wenderoth, R., Riesenberg, D. and Pluckthun, A. (1993). Improved bivalent miniantibodies, with identical avidity as whole antibodies, produced by high cell density fermentation of *Escherichia coli*. Biotechnology 11:1271-1277.

Penttilä, M., Nevalainen, H., Rättö, M., Salminen, E. and Knowles, J. (1987). A versatile transformation system for the cellulolytic filamentous fungus *Trichoderma reesei*. Gene 61:155-164.

Pere, J., Siika-aho, M., Buchert, J. and Viikari. L. (1995). Effect of purified *Trichoderma reesei* cellulases on the fiber properties of kraft pulp. Tappi Journal 78:71-78.

Qiao, M., Ye, S., Koponen, O., Ra, R., Usabiaga, M., Inmonen, T., Saris, P. E. J. (1996) Regulation of the nisin operons in *Lactococcus* lactis N8. J. Appl. Biochem. 80:626-634.

Russo, P. S., Blum, F. D., Ispen, J. D., Abul-Hajj, Y. J. and Miller, W. G. (1992). Can. J. Bot. 60: 1414-1422.

Schreuder, M. P. et al. (1996). Trends Biotechnol. 14:115-120.

Sherman, F., Fink, G. R. and Hicks, J. B. (1983). Methods in Yeast Genetics. A Laboratory Manual. Cold Spring Harbor Laboratory, Cold Spring Harbor, N.Y.

Suominen, P., Mäntylä, A., Saarelainen, R., Paloheimo, M., Fagerström, R., Parkkinen, E. and Nevalainen, H. (1992). Genetic engineering of Trichoderma reesei to produce suitable e enzyme combinations for applications in the pulp and paper industry. In: Kuwahara. M. and Shimada, M. (eds.) Biotechnology in Pulp and Paper Industry p. 439-445. (Proc. 5th Int. Conf. Biotechn. Pulp Pap. Ind., Kyoto, Japan, 1992)

Ståhl, S. and Uhlén, M. (1997). Trends Biotechnol. 15:185-192.

Takkinen, K., Laukkanen, M.-L., Sizmann, D., Alfthan, K., Immonen, T., Vanne, L., Kaartinen, M., Knowles, J. K. C. and Teeri, T. T. (1991). An active single-chain antibody containing a cellulase linker domain is secreted by Escherichia coli. Protein Eng. 4:837-841.

Temple, B., Horgen, P. A., Bernier, L. and Hintz, W. E. (1997). Cerato-ulmin, a hydrophobin secreted by the causal agents of Dutch Elm Disease, is a parasitic fitness factor. Fungal Gen. Biol. 22:39-51.

Terstappen, G. C., Geerts, A. J., Kula, M.-R., 1992 "The use of detergent based aqueous two-phase systems for the isolation of extracellular proteins: Purification of a lipase from Pseudomonas cepacia", Biotechnol. Appl. Biochem. 16, 228-235

Terstappen, G. C., Ramelmeier, R. A. and Kula M.-R., 1993, Protein partitioning in detergent-based aqueous two-phase systems, J. Biotechnol. 28: 263-275

Thomas, B. J. and Rothstein, R. (1989). Elevated recombination rates in transcriptionally active DNA. Cell 56: 619-630.

van Tilbeurgh H. and Caeyssens M. (1985). Detection and differentiation of cellulase components using low molecular mass fluorogenic substrates. FEBS letters 187:283-288.

van Tilbeurgh H., Caeyssens M. and de Brayne C. K. (1982). The use of 4-methylumbelliferyl and other chromophoric glycosides in the study of cellulolytic enzymes. FEBS letters 194:152-156.

Tilburn, J., Scazzocchio, C., Taylor, G. G., Zabicky-Zissman, J. H., Lockington, R. A. and Davies, R. W. (1983). Transformation by integration in Aspergillus nidulans. Gene 26:205-221.

Tjerneld, F., Berner, S., Cajarville, A. and Johansson, G. (1986). New aqueous two-phase system based on hydroxypropyl starch useful in enzyme purification. Enz. Microb. Technol. 8:417-423.

Veide, A., Lindbäck, T. and Enfors, S. (1984). Continuous extraction of β-D-galactosidase from Escherichia coli in an aqueous two-phase system: effects of biomass concentration on partitioning and mass transfer. Enz. Microb. Technol. 6:325-330.

Walter, H., Brooks, D. E. and Fisher, D. (1985). Partitioning in Aqueous Two-Phase Systems, Academic Press, Inc., Orlando.

Watari, J., Nomura, M., Sahara, H. and Koshino, S. (1994). Construction of flocculent brewer's yeast by chromosomal integration of the yeast flocculation gene FLO1. J. Inst. Brew. 100:73-77.

Wessels, J. G. H. (1994). Developmental regulation of fungal cell wall formation. Annu. Rev. Phytopathol. 32:413-437.

Wösten, H. A. B., Schuren, F. H. J. and Wessels, J. G. H. (1994a). The fungal hydrophobin Sc3p self-assembles at the surface of aerial hyphae as a protein membrane constituting the hydrophobic rodlet layer. Eur. J. Cell Biol. 63:122-129.

Wösten, H. A. B., Schuren, F. H. J. and Wessels, J. G. H. (1994b). Interfacial self-assembly of a hydrophobin into an amphipathic protein membrane mediates fungal attachment to hydrophobic surfaces. EMBO J. 13:5848-5854.

Wösten, H. A. B., Bohlmann, R., Eckerskorn, C., Lottspeich, F., Bölker, M. and Kahmann R. (1996) EMBO J. 15:4274-4281.

Wösten, H. A. B. and Wessels, J. G. H. (1997). Hydrophobins, from molecular structure to multiple functions in fungal development. Mycoscience 38:363-374.

---

The invention claimed is:

1. A recombinant microorganism selected from the group consisting of bacteria, yeasts or filamentous fungi, producing a fusion protein comprising a hydrophobin or a hydrophobin-like protein fused to a protein of interest an enzyme of interest or part of an enzyme of interest which has enzymatic activity, wherein said hydrophobin or hydrophobin-like protein has an ability to partition in aqueous two-phase systems (ATPS) and to carry said protein of interest enzyme of interest or part of an enzyme of interest which has enzymatic activity into one phase of said ATPS.

2. The recombinant microorganism according to claim 1, wherein the organism has been genetically modified to be capable of producing said fusion protein.

3. The recombinant microorganism according to claim 1, wherein the hydrophobin is a *Trichoderma* hydrophobin.

4. The recombinant microorganism according to claim 3, wherein the *Trichoderma* hydrophobin is hydrophobin I (HFBI), hydrophobin II (HFBII) or spore-related hydrophobin I (SRHI).

5. The recombinant microorganism according to claim 1, wherein the hydrophobins or hydrophobin-like proteins form aggregates.

6. The recombinant microorganism according to claim 1, wherein the enzyme of interest is a cell-bound enzyme or a part of said cell-bound enzyme found in extra- or intracellular locations, including cell wall bound molecules.

7. The recombinant microorganism according to claim 1, wherein the enzyme of interest is an extracellular enzyme or a part of said extracellular enzyme.

8. The recombinant microorganism according to claim 1, which is *E. coli*.

9. The recombinant microorganism according to claim 8, which is *E. coli* strain RV308.

10. The recombinant microorganism according to claim 1, which is *S. cerevisiae*.

11. The recombinant microorganism according to claim 10, which is *S. cerevisiae* strain VTT-C-99315.

12. The recombinant microorganism according to claim 1, which is *T. reesi*.

13. The recombinant microorganism according to claim 12, which is *T. reesei* strain Δhfb2.

14. A recombinant microorganism selected from the group consisting of bacteria, yeasts or filamentous fungi, producing a fusion protein comprising a hydrophobin or a hydrophobin-like protein fused to an extracellular enzyme of *Trichoderma* or a part of said extracellular enzyme which has enzymatic activity, selected from the group consisting of cellulases, hemicellulases and proteases, wherein said hydrophobin or hydrophobin-like protein has an ability to partition in aqueous two-phase systems (ATPS) and to carry said protein of interest extracellular enzyme or part of said extracellular enzyme which has enzymatic activity into one phase of said ATPS.

15. A recombinant microorganism selected from the group consisting of bacteria, yeasts or filamentous fungi, producing a fusion protein comprising a hydrophobin or a hydrophobin-like protein fused to an antibody protein or a part of said antibody protein which binds to antigen, wherein said hydrophobin or hydrophobin-like protein has an ability to partition in aqueous two-phase systems (ATPS) and to carry said protein of interest antibody protein or part of said antibody protein which binds to antigen into one phase of said ATPS.

16. The recombinant microorganism according to claim 1, 14 or 15, wherein the recombinant microorganism is a yeast.

17. The recombinant microorganism according to claim 1, 14, or 15, wherein the recombinant microorganism is a filamentous fungi.

18. The recombinant microorganism according to claims 1, 14, or 15, wherein the recombinant microorganism is a bacteria.

* * * * *